(12) United States Patent
Kawakami et al.

(10) Patent No.: US 9,899,603 B2
(45) Date of Patent: *Feb. 20, 2018

(54) ORGANIC COMPOUND, LIGHT-EMITTING ELEMENT, LIGHT-EMITTING DEVICE, ELECTRONIC APPLIANCE, AND LIGHTING DEVICE

(71) Applicant: Semiconductor Energy Laboratory Co., Ltd., Kanagawa-ken (JP)

(72) Inventors: Sachiko Kawakami, Kanagawa (JP); Naoaki Hashimoto, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/446,528

(22) Filed: Mar. 1, 2017

(65) Prior Publication Data

US 2017/0229648 A1 Aug. 10, 2017

Related U.S. Application Data

(63) Continuation of application No. 14/809,427, filed on Jul. 27, 2015, now Pat. No. 9,586,924, which is a continuation of application No. 14/338,897, filed on Jul. 23, 2014, now Pat. No. 9,093,649.

(30) Foreign Application Priority Data

Jul. 26, 2013 (JP) ................. 2013-155318

(51) Int. Cl.
*H01L 51/00* (2006.01)
*C07D 307/77* (2006.01)
*C09K 11/06* (2006.01)
*H01L 51/50* (2006.01)

(52) U.S. Cl.
CPC .......... *H01L 51/006* (2013.01); *C07D 307/77* (2013.01); *C09K 11/06* (2013.01); *H01L 51/0061* (2013.01); *C09K 2211/1011* (2013.01); *C09K 2211/1022* (2013.01); *C09K 2211/1088* (2013.01); *H01L 51/0054* (2013.01); *H01L 51/0073* (2013.01); *H01L 51/5012* (2013.01)

(58) Field of Classification Search
CPC .................................................. H01L 51/006
USPC ........................................................ 549/457
See application file for complete search history.

(56) References Cited

U.S. PATENT DOCUMENTS

| | | |
|---|---|---|
| 7,326,476 B2 | 2/2008 | Sotoyama |
| 8,604,224 B2 | 12/2013 | Suzuki et al. |
| 8,629,430 B2 | 1/2014 | Kawamura et al. |
| 8,866,135 B2 | 10/2014 | Kawamura et al. |
| 9,147,847 B2 | 9/2015 | Kawamura et al. |
| 9,373,792 B2 | 6/2016 | Kawamura et al. |
| 2005/0079385 A1 | 4/2005 | Nomura et al. |
| 2010/0314615 A1 | 12/2010 | Mizuki et al. |
| 2011/0156016 A1 | 6/2011 | Kawamura et al. |
| 2011/0248246 A1 | 10/2011 | Ogita et al. |
| 2012/0112169 A1 | 5/2012 | Mizuki et al. |
| 2012/0138914 A1 | 6/2012 | Kawamura et al. |
| 2012/0165556 A1 | 6/2012 | Suzuki et al. |
| 2014/0124764 A1 | 5/2014 | Kitano et al. |
| 2015/0005512 A1 | 1/2015 | Kawamura et al. |

FOREIGN PATENT DOCUMENTS

| | | |
|---|---|---|
| CN | 102219774 A | 10/2011 |
| CN | 102448945 A | 5/2012 |
| EP | 2 436 679 A1 | 4/2012 |
| JP | 2005-075868 A | 3/2005 |
| JP | 2011-173973 A | 9/2011 |
| JP | 2011-231108 A | 11/2011 |
| JP | 2012-149045 A | 8/2012 |
| JP | 2013-087090 A | 5/2013 |
| JP | 2013-107853 A | 6/2013 |
| JP | 2013-209397 A | 10/2013 |
| KR | 2011-0113593 A | 10/2011 |
| KR | 2012-0038402 A | 4/2012 |
| KR | 2013-0096647 A | 8/2013 |
| TW | 201105679 | 2/2011 |
| WO | WO 2009/084512 A1 | 7/2009 |
| WO | WO 2010/013675 A1 | 2/2010 |
| WO | WO 2010/013676 A1 | 2/2010 |
| WO | WO 2010/122810 A1 | 10/2010 |
| WO | WO 2010/137285 A1 | 12/2010 |
| WO | WO 2012/090970 A1 | 7/2012 |

OTHER PUBLICATIONS

International Search Report re Application No. PCT/IB2014/063173, dated Dec. 9, 2014.
Written Opinion re Application No. PCT/IB2014/063173, dated Dec. 9, 2014.
Illustration 1: Effective Filing Date (under AIA), p. 15.
Chinese Office Action re Application No. CN 201480042018.6, dated Dec. 27, 2016.

*Primary Examiner* — Taofiq A Solola
(74) *Attorney, Agent, or Firm* — Husch Blackwell LLP

(57) ABSTRACT

An organic compound that emits blue light with high color purity and has a long lifetime is provided as a novel substance. The organic compound is a fluorescent organic compound having a structure in which benzonaphthofuranylamine is bonded to the 1-position and the 6-position of a pyrene skeleton.

14 Claims, 27 Drawing Sheets

ORGANIC COMPOUND, LIGHT-EMITTING ELEMENT, LIGHT-EMITTING DEVICE, ELECTRONIC APPLIANCE, AND LIGHTING DEVICE

This application is a continuation of copending U.S. application Ser. No. 14/809,427, filed on Jul. 27, 2015 which is a continuation of U.S. application Ser. No. 14/338,897, filed on Jul. 23, 2014 (now U.S. Pat. No. 9,093,649 issued Jul. 28, 2015), which are all incorporated herein by reference.

TECHNICAL FIELD

One embodiment of the present invention relates to a novel organic compound emitting fluorescence. One embodiment of the present invention relates to a light-emitting element, a light-emitting device, an electronic appliance, and a lighting device each of which uses the novel organic compound emitting fluorescence.

BACKGROUND ART

Light-emitting elements utilizing electroluminescence (EL) are highly anticipated as next-generation display technology. In recent years, research and development has been extensively conducted on such light-emitting elements. In a basic structure of the light-emitting element, a layer containing a light-emitting substance is provided between a pair of electrodes. By applying voltage to the element, light emission can be obtained from the light-emitting substance in an excited state.

The light-emitting element is a self-luminous element and thus has advantages over a liquid crystal display element, such as high visibility of the pixels and no need for backlight, and is considered to be suitable as a flat panel display element. Another major advantage of the light-emitting element is that it can be fabricated to be thin and lightweight. Besides, very high response speed is also a feature of the light-emitting element.

Furthermore, the light-emitting element can be formed in a film form, and thus makes it possible to provide planar light emission easily. Thus, a large-area element utilizing planar light emission can be formed. This is a feature that is difficult to obtain with point light sources typified by an incandescent lamp and an LED or linear light sources typified by a fluorescent lamp. Thus, the light-emitting element also has great potential as a planar light source that can be used for a lighting device and the like.

Light-emitting elements are broadly classified according to whether they use an organic compound or an inorganic compound as a light-emitting substance. In the case where an organic compound is used as a light-emitting substance, by applying voltage to a light-emitting element, electrons and holes are injected from a pair of electrodes into a layer including the light-emitting organic compound, whereby current flows. Then electrons and holes (i.e., carriers) are recombined, so that the light-emitting organic compound is excited. The light-emitting organic compound returns to a ground state from the excited state, thereby emitting light. Note that an excited state of an organic compound can be of two types: a singlet excited state and a triplet excited state, and luminescence from the singlet excited state (S*) is referred to as fluorescence, and luminescence from the triplet excited state (T*) is referred to as phosphorescence. Note that in fabrication of a light-emitting element, characteristics of the light-emitting element are greatly affected by such light-emitting substances.

A method has been disclosed in which a novel fluorescent material with high emission efficiency is used for a light-emitting layer included in a light-emitting element to provide a highly efficient light-emitting element (see, for example, Patent Document 1).

REFERENCE

Patent Document 1: Japanese Published Patent Application No. 2005-75868

DISCLOSURE OF INVENTION

Although novel fluorescent materials with good characteristics have been developed as disclosed in Patent Document 1, development of novel materials with better characteristics is demanded.

In view of the above, one embodiment of the present invention provides a fluorescent organic compound that emits light with high color purity and has a long lifetime as a novel substance. One embodiment of the present invention also provides a light-emitting element that emits blue light with high color purity and has a long lifetime, a light-emitting device, an electronic appliance, or a lighting device.

One embodiment of the present invention is a blue fluorescent organic compound that has a structure in which benzonaphthofuranylamine is bonded to each of the 1-position and the 6-position of a pyrene skeleton. Thus, one embodiment of the present invention is an organic compound represented by General Formula (G1).

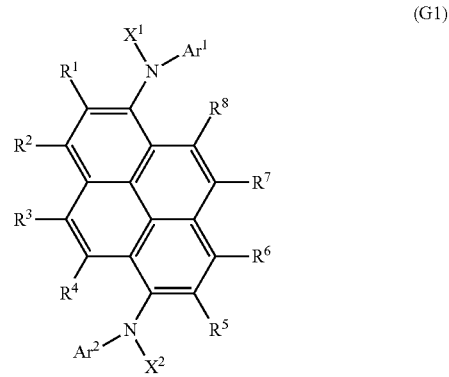

(G1)

In the formula, $Ar^1$ and $Ar^2$ separately represent a substituted or unsubstituted aryl group having 6 to 13 carbon atoms forming a ring; $R^1$ to $R^8$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms; and $X^1$ and $X^2$ separately represent a substituted or unsubstituted benzo[b]naphtho[1,2-d]furanyl group.

It is preferable that each nitrogen atom in General Formula (G1) having the above-described structure be bonded to the 6-position or the 8-position of the benzo[b]naphtho[1,2-d]furanyl group.

Another embodiment of the present invention is an organic compound represented by General Formula (G2).

(G2)

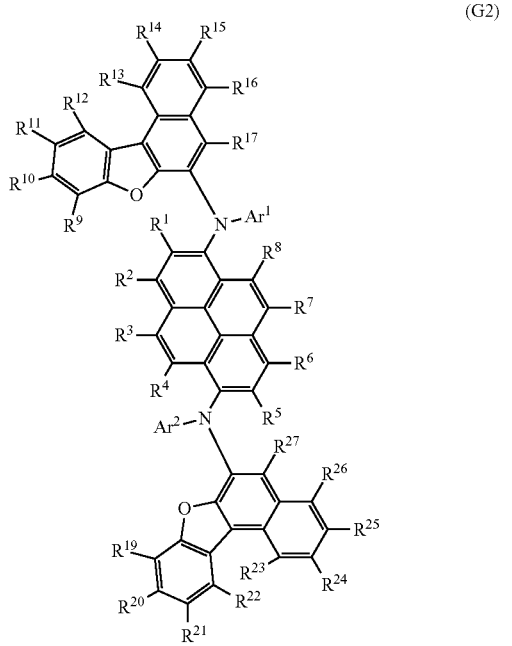

In the formula, $Ar^1$ and $Ar^2$ separately represent a substituted or unsubstituted aryl group having 6 to 13 carbon atoms forming a ring; and $R^1$ to $R^{17}$ and $R^{19}$ to $R^{27}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is an organic compound represented by General Formula (G3).

(G3)

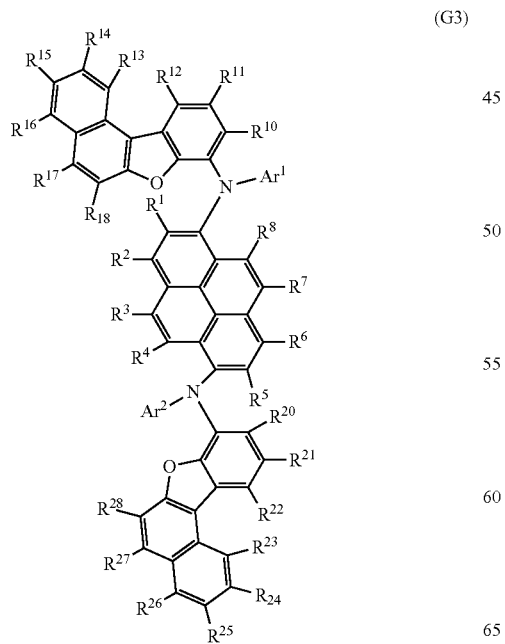

In the formula, $Ar^1$ and $Ar^2$ separately represent a substituted or unsubstituted aryl group having 6 to 13 carbon atoms forming a ring; and $R^1$ to $R^8$, $R^{10}$ to $R^{18}$, and $R^{20}$ to $R^{28}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is an organic compound represented by General Formula (G4).

(G4)

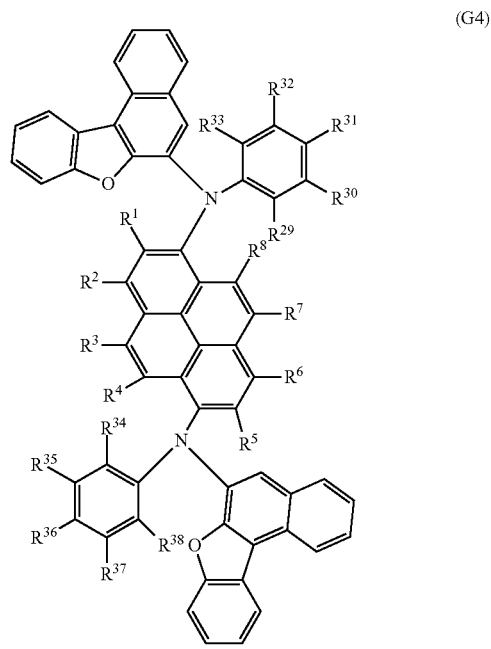

In the formula, $R^1$ to $R^8$ and $R^{29}$ to $R^{38}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is an organic compound represented by General Formula (G5).

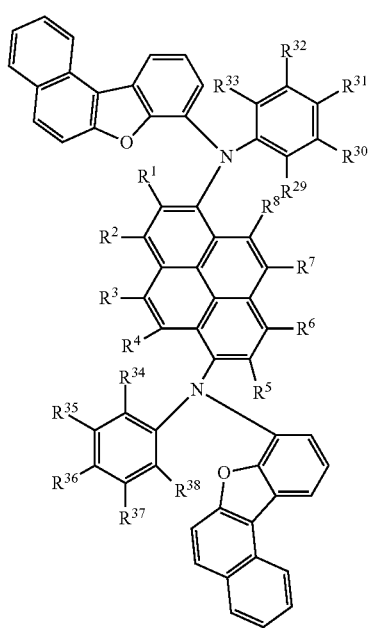

(G5)

In the formula, $R^1$ to $R^8$ and $R^{29}$ to $R^{38}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Another embodiment of the present invention is an organic compound represented by Structural Formula (100).

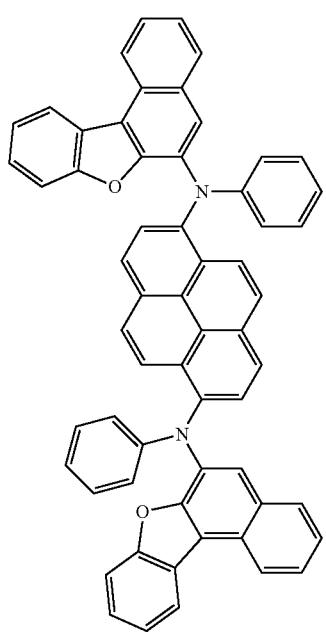

(100)

Another embodiment of the present invention is an organic compound represented by Structural Formula (101).

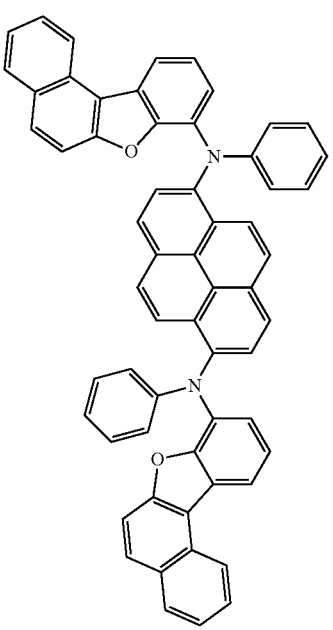

(101)

Another embodiment of the present invention is a method for synthesizing each of the organic compounds represented by General Formulae (G1) to (G5) and 8-halogenated benzo[b]naphtho[1,2-d]furan, a novel organic compound synthesized using any of the organic compounds represented by General Formulae (G1) to (G5). Note that halogen in 8-halogenated benzo[b]naphtho[1,2-d]furan is preferably chlorine, bromine, or iodine.

Another embodiment of the present invention is a light-emitting element containing any of the organic compounds represented by General Formulae (G1) to (G5) and a light-emitting device including the light-emitting element.

Note that other embodiments of the present invention are not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

According to one embodiment of the present invention, a fluorescent organic compound that emits blue light (emission peak wavelength: around 450 nm) with high color purity, has high efficiency, and has a long lifetime can be provided as a novel substance. The use of the organic compound of one embodiment of the present invention can provide a light-emitting element that emits blue light with high color purity, a light-emitting device, an electronic appliance, or a lighting device. A light-emitting element, a light-emitting device, an electronic appliance, or a lighting device that has low power consumption and has a long lifetime can also be provided.

BEST MODE FOR CARRYING OUT THE INVENTION

Figure 1:
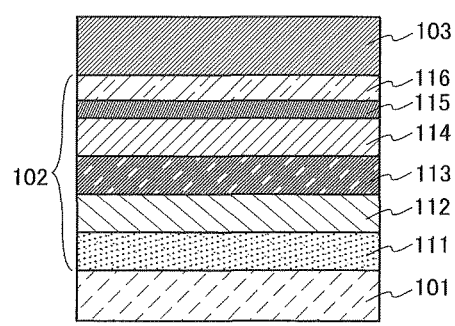
FIG. 1 illustrates a structure of a light-emitting element.

Hereinafter, embodiments of the present invention are described with reference to the drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, novel organic compounds of embodiments of the present invention are described.

The organic compound of one embodiment of the present invention is a fluorescent organic compound that emits blue light and has a structure in which benzonaphthofuranylamine is bonded to each of the 1-position and the 6-position of a pyrene skeleton. Note that one mode of the organic compound described in this embodiment is an organic compound represented by General Formula (G1).

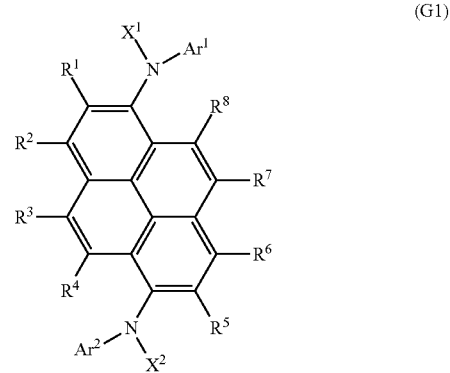

(G1)

In General Formula (G1), $Ar^1$ and $Ar^2$ separately represent a substituted or unsubstituted aryl group having 6 to 13 carbon atoms forming a ring; $R^1$ to $R^8$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms; and $X^1$ and $X^2$ separately represent a substituted or unsubstituted benzo[b]naphtho[1,2-d]furanyl group.

The organic compound represented by General Formula (G1) is preferably an organic compound represented by General Formula (G2).

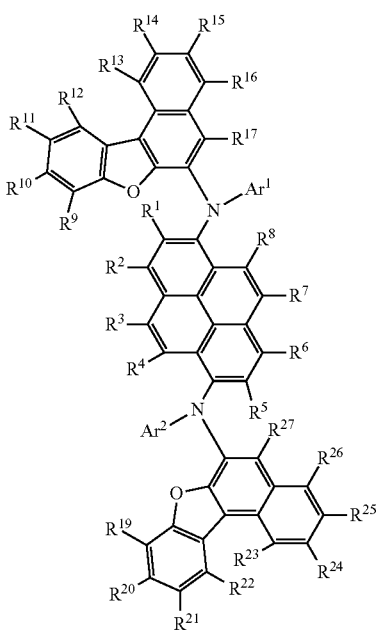

(G2)

In General Formula (G2), $Ar^1$ and $Ar^2$ separately represent a substituted or unsubstituted aryl group having 6 to 13 carbon atoms forming a ring; and $R^1$ to $R^{17}$ and $R^{19}$ to $R^{27}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

The organic compound represented by General Formula (G1) is preferably an organic compound represented by General Formula (G3). Note that the organic compound represented by General Formula (G3) is preferable because its emission wavelength can be shorter.

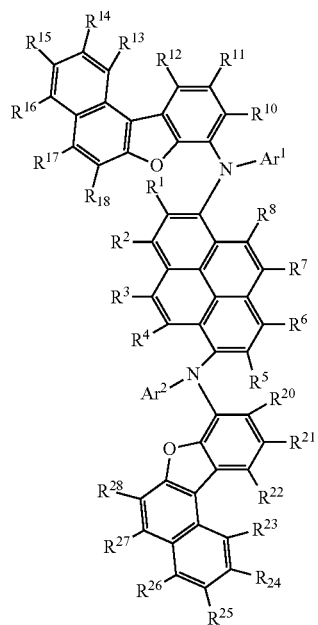

(G3)

In General Formula (G3), $Ar^1$ and $Ar^2$ separately represent a substituted or unsubstituted aryl group having 6 to 13 carbon atoms forming a ring; and $R^1$ to $R^8$, $R^{10}$ to $R^{18}$, and $R^{20}$ to $R^{28}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms. In a substance represented by General Formula (G3), each of $R^{18}$ and $R^{28}$ is preferably a substituted or unsubstituted phenyl group, in which case the emission wavelength of the substance can be short. The substance in which $R^{18}$ and $R^{28}$ are substituted or unsubstituted phenyl groups is preferably used for a light-emitting element, in which case the light-emitting element has an emission spectrum with a narrow half-width, high emission efficiency, and high reliability. In order to prevent distortion of a stereostructure, $R^{18}$ and $R^{28}$ are further preferably unsubstituted phenyl groups. In the case where $R^{18}$ and $R^{28}$ are each a phenyl group having a substituent, the substituent is preferably an alkyl group having 1 to 6 carbon atoms or a phenyl group.

The organic compound represented by General Formula (G2) is preferably an organic compound represented by General Formula (G4).

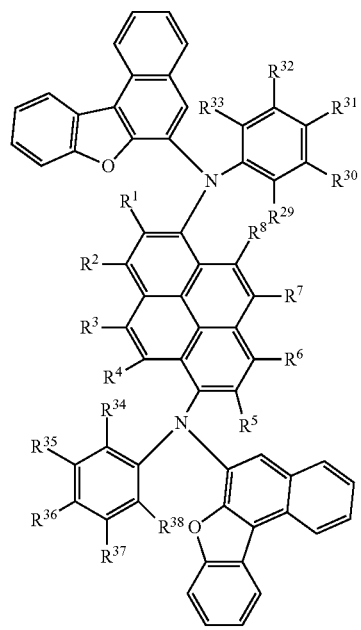

(G4)

In General Formula (G4), $R^1$ to $R^8$ and $R^{29}$ to $R^{38}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

The organic compound represented by General Formula (G3) is preferably an organic compound represented by General Formula (G5). Note that the organic compound represented by General Formula (G5) is preferable because its emission wavelength can be shorter.

(G5)

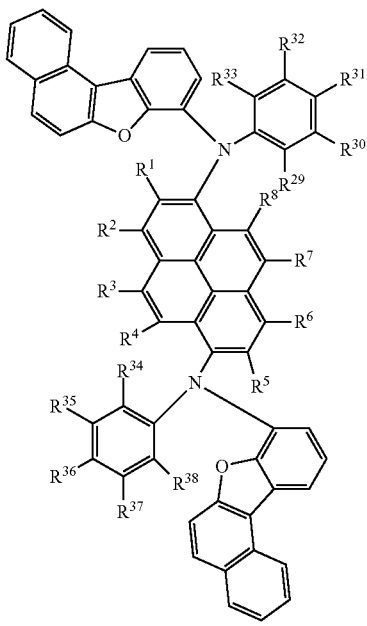

In General Formula (G5), $R^1$ to $R^8$ and $R^{29}$ to $R^{38}$ separately represent hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms.

Specific examples of the substituted or unsubstituted aryl group having 6 to 13 carbon atoms forming a ring in General Formulae (G1) to (G3) and the substituted or unsubstituted aryl group having 6 to 10 carbon atoms in General Formulae (G4) and (G5) include a phenyl group, a 1-naphthyl group, a 2-naphthyl group, an ortho-tolyl group, a meta-tolyl group, a para-tolyl group, an ortho-biphenyl group, a meta-biphenyl group, a para-biphenyl group, a 9,9-dimethyl-9H-fluoren-2-yl group, a 9,9-diphenyl-9H-fluoren-2-yl group, a 9H-fluoren-2-yl group, a para-tert-butylphenyl group, and a mesityl group.

Specific examples of the substituted or unsubstituted alkyl groups having 1 to 6 carbon atoms in General Formulae (G1) to (G5) include a methyl group, an ethyl group, an n-propyl group, an isopropyl group, a n-butyl group, a sec-butyl group, an isobutyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, a neo-hexyl group, a cyclohexyl group, a 3-methylpentyl group, a 2-methylpentyl group, a 2-ethylbutyl group, a 1,2-dimethylbutyl group, and a 2,3-dimethylbutyl group.

Specific examples of the substituted or unsubstituted alkoxy groups having 1 to 6 carbon atoms, the cyano group, the halogen, and the substituted or unsubstituted haloalkyl group having 1 to 6 carbon atoms in General Formulae (G1) to (G5) include a methoxy group, an ethoxy group, an n-propoxy group, an isopropoxy group, an n-butoxy group, a sec-butoxy group, an isobutoxy group, a tert-butoxy group, an n-pentyloxy group, an isopentyloxy group, a sec-pentyloxy group, a tert-pentyloxy group, a neo-pentyloxy group, an n-hexyloxy group, an isohexyloxy group, a sec-hexyloxy group, a tert-hexyloxy group, a neo-hexyloxy group, a cyclohexyloxy group, a 3-methylpentyloxy group, a 2-methylpentyloxy group, a 2-ethylbutoxy group, a 1,2-dimethylbutoxy group, a 2,3-dimethylbutoxy group, a cyano group, fluorine, chlorine, bromine, iodine, and a trifluoromethyl group.

Note that the organic compound of one embodiment of the present invention has the structure in which benzonaphthofuranylamine is bonded to each of the 1-position and the 6-position of the pyrene skeleton. This structure enables effective conjugation length from the pyrene skeleton to benzonaphthofuranylamine to be increased. By increasing the effective conjugation length, the emission peak wavelength can be controlled to be optimal. Thus, an organic compound that emits blue light with high color purity can be obtained in one embodiment of the present invention. Particularly in the case of benzonaphthofuranylamine in which an amine skeleton is bonded to the 8-position of a benzo[b]naphtho[1,2-d]furanyl group, the purity of blue can be increased.

In the case of the structure in which benzonaphthofuranylamine is bonded to each of the 1-position and the 6-position of the pyrene skeleton as in the organic compound of one embodiment of the present invention, amine skeletons are stabilized by benzonaphtho furanyl groups and an increase in the reliability is expected. Thus, in one embodiment of the present invention, an organic compound that has high efficiency and a long lifetime can be obtained.

Next, specific structural formulae of the organic compounds of embodiments of the present invention (General Formulae (G1) to (G5)) are shown (Structural Formulae (100) to (137)). Note that the present invention is not limited thereto.

(100)

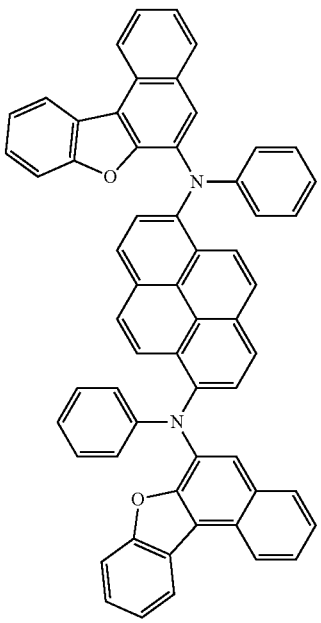

(101)
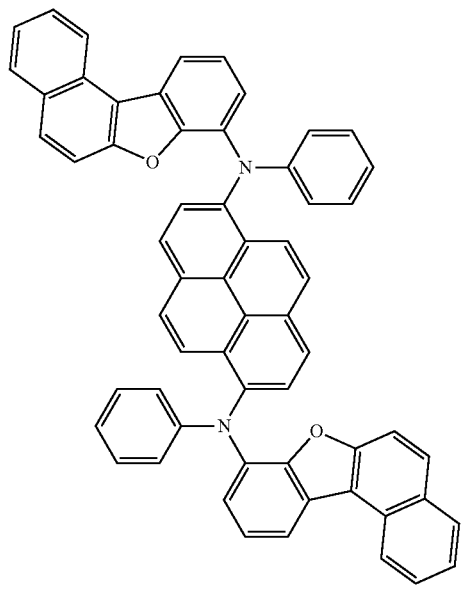
(102)
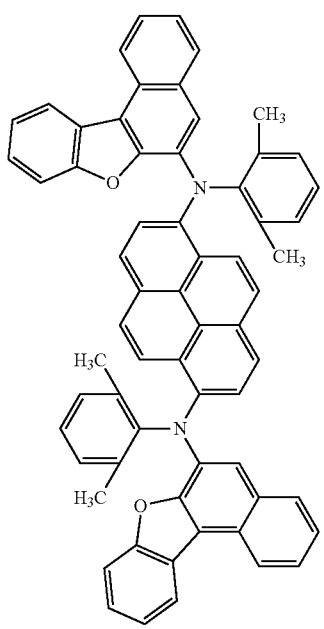
(103)
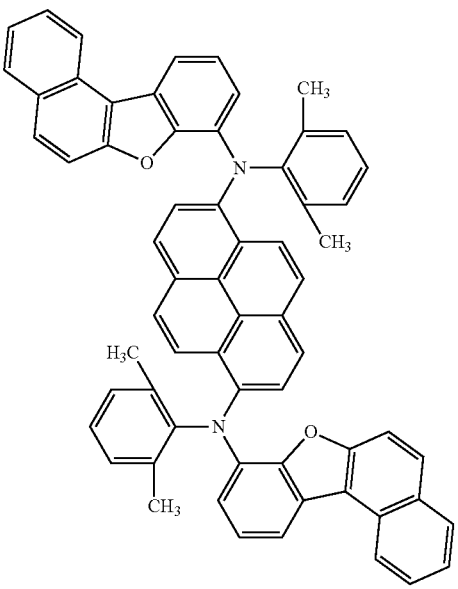
(104)
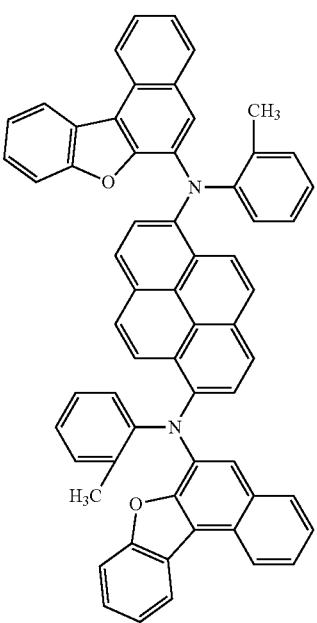

(105)
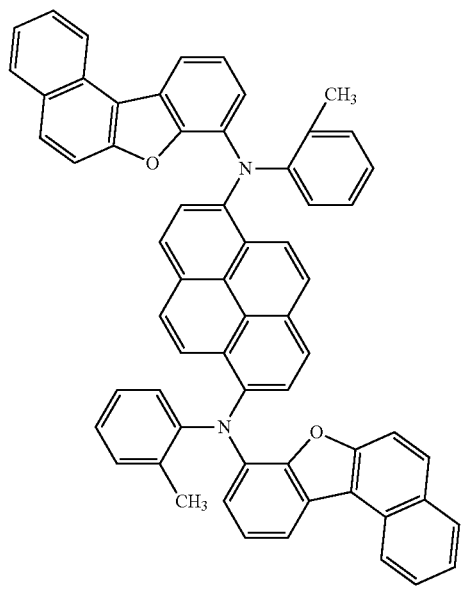
(106)
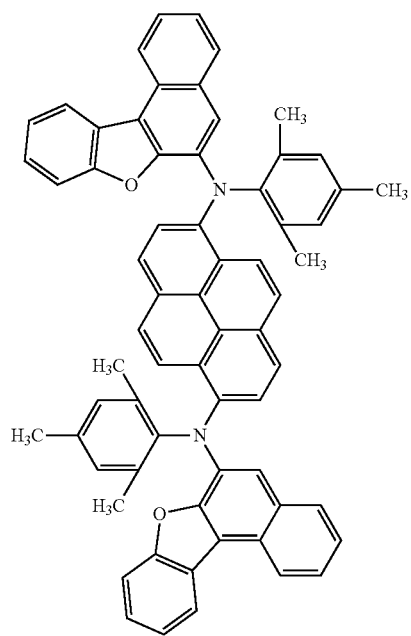
(107)
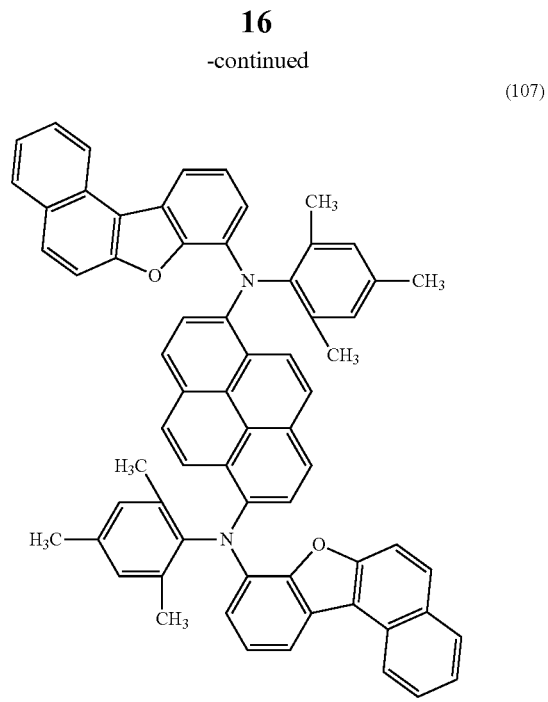
(108)
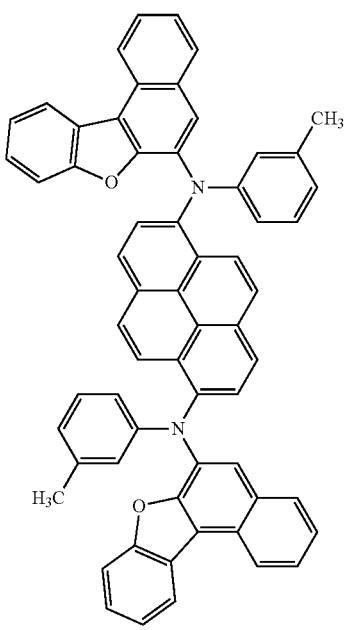

(109)
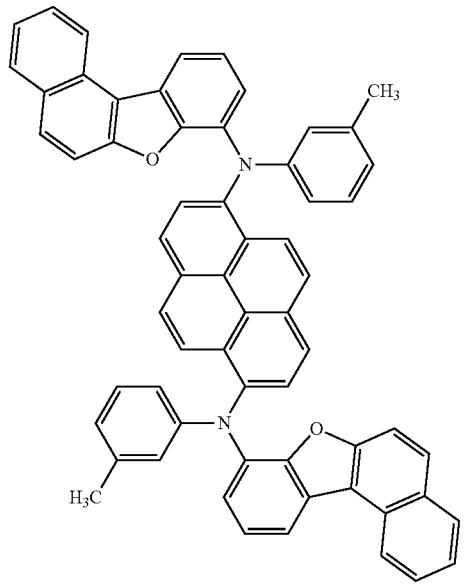
(111)
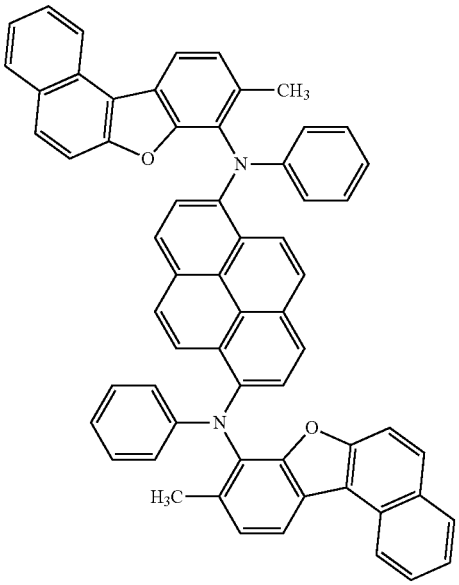
(110)
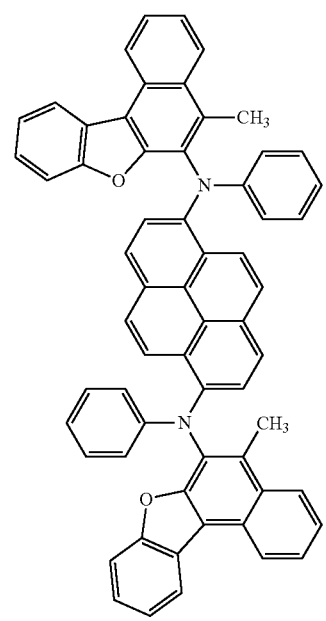
(112)
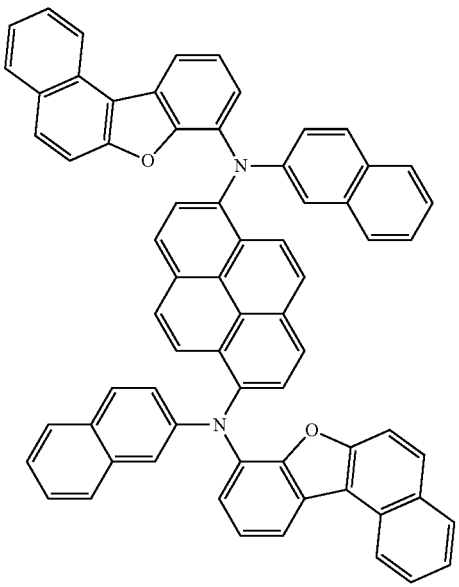

(113)
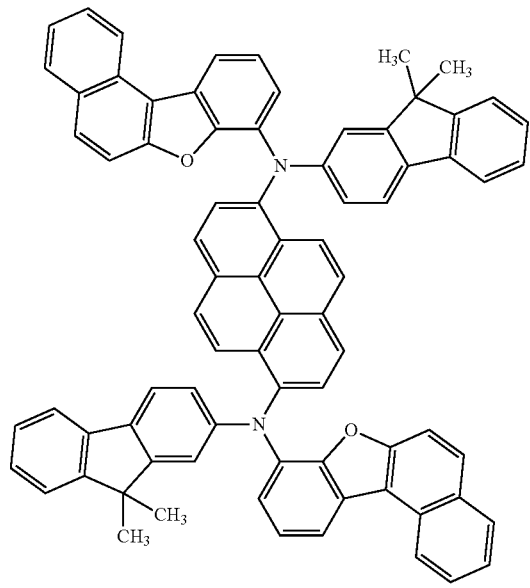
(114)
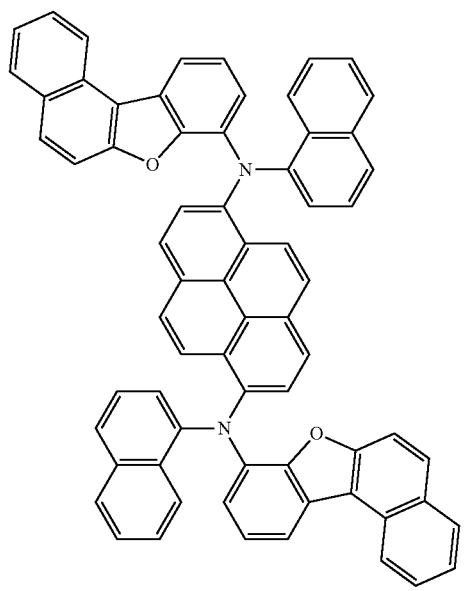
(115)
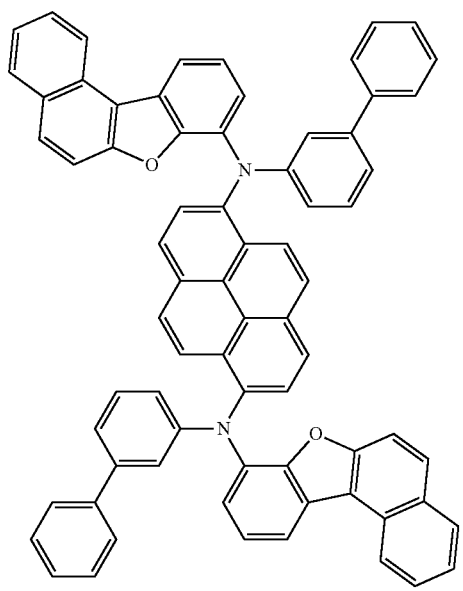
(116)
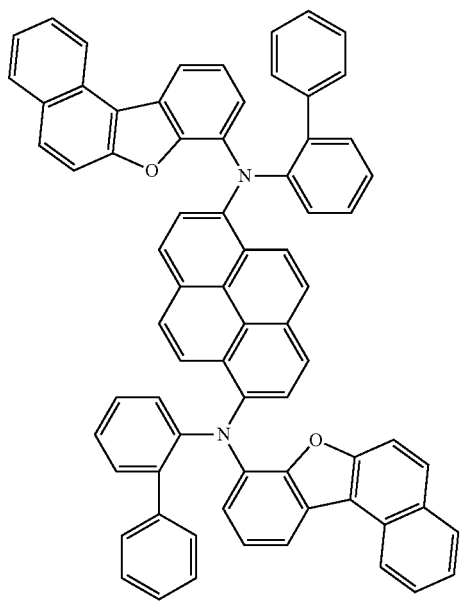

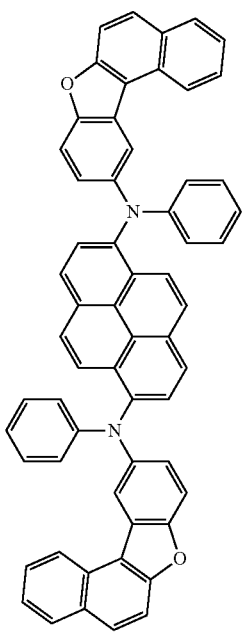
(117)
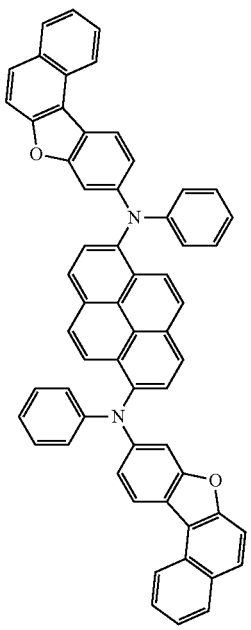
(119)
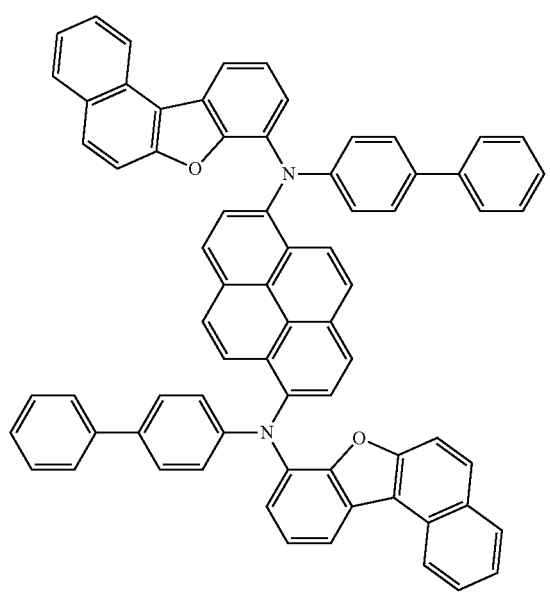
(118)
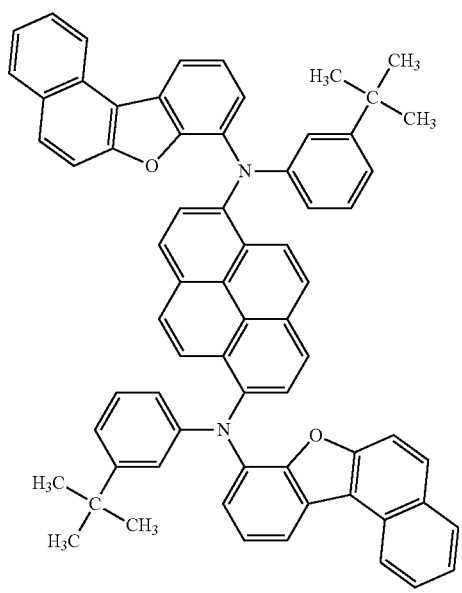
(120)

(121)
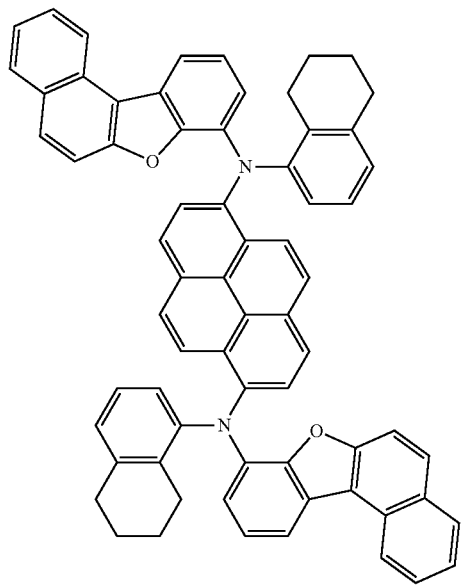
(122)
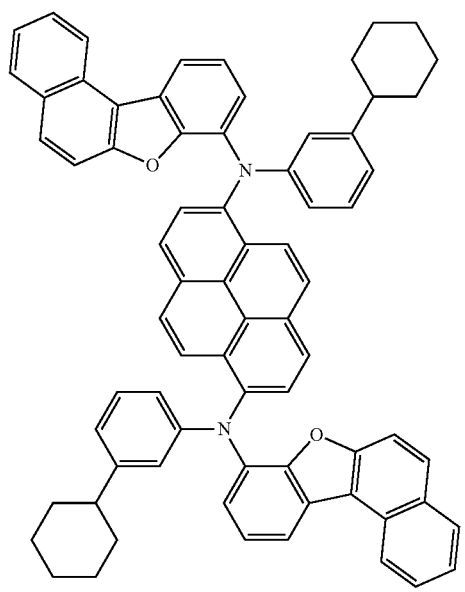
(123)
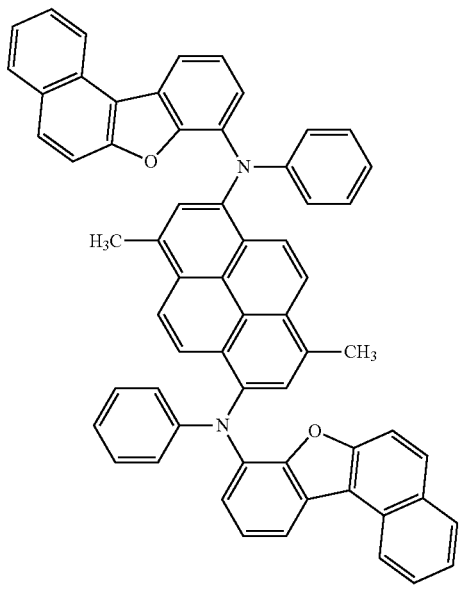
(124)
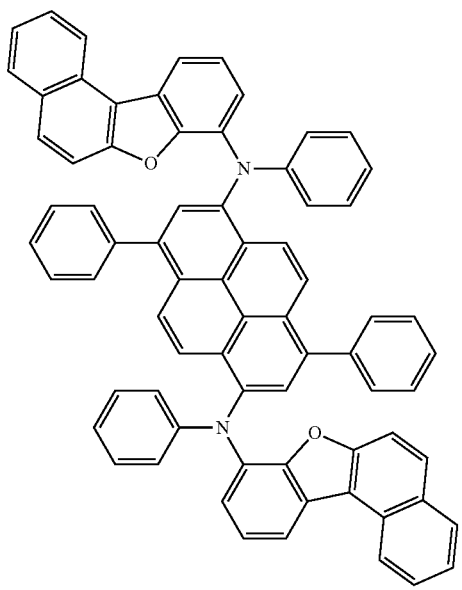

(125)
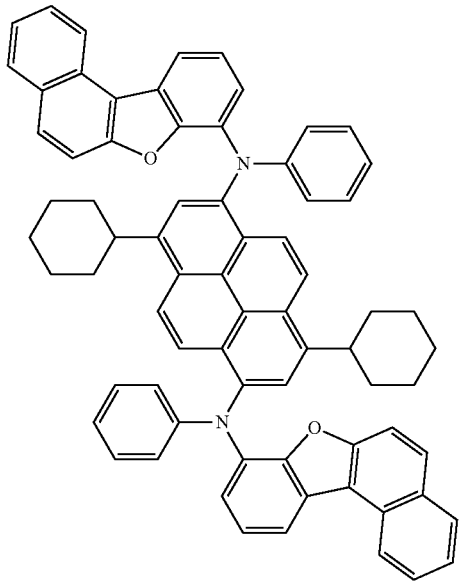
(127)
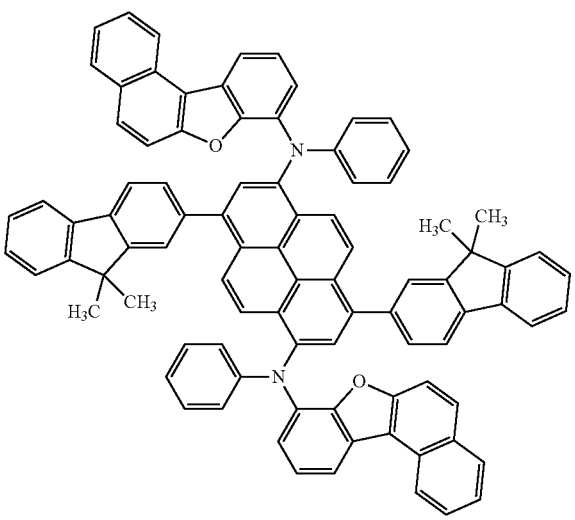
(126)
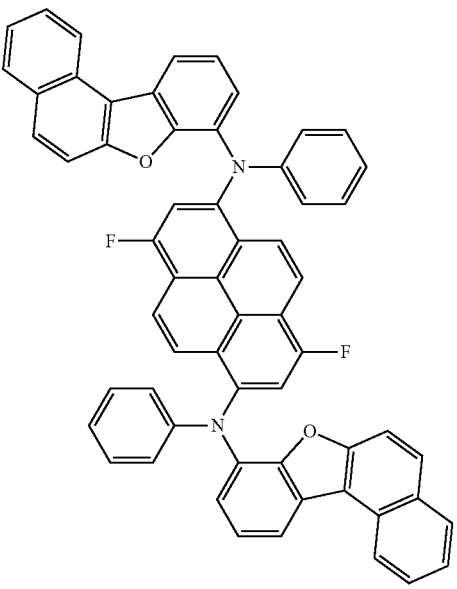
(128)

(129)
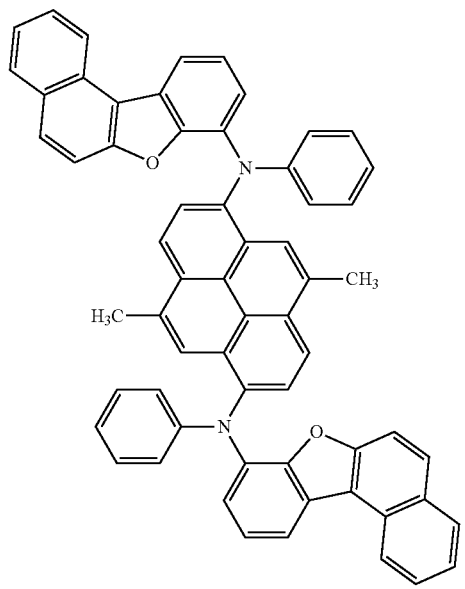
(130)
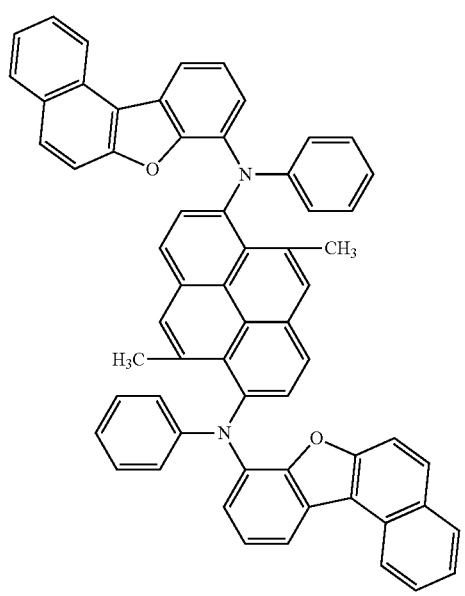
(131)
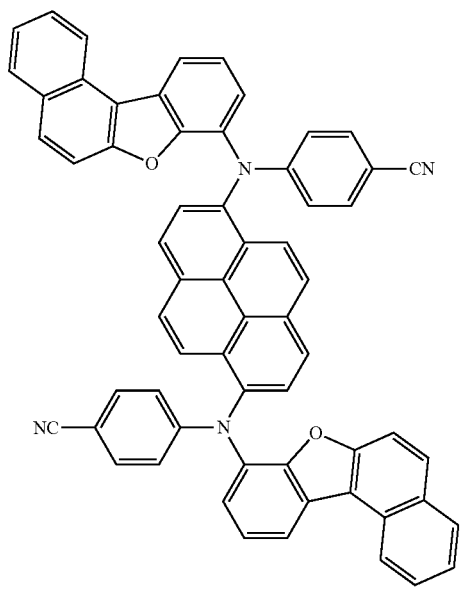
(132)
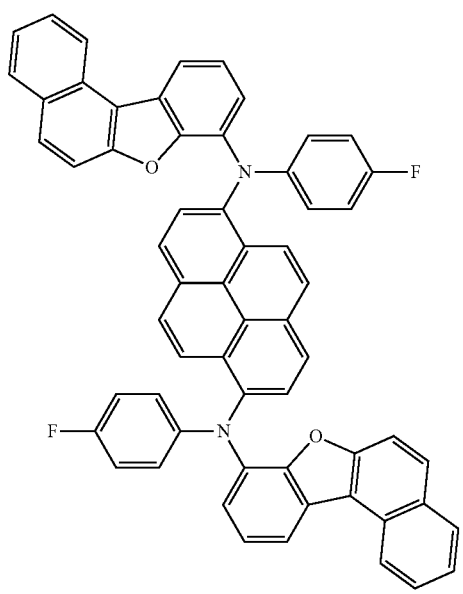

(133)
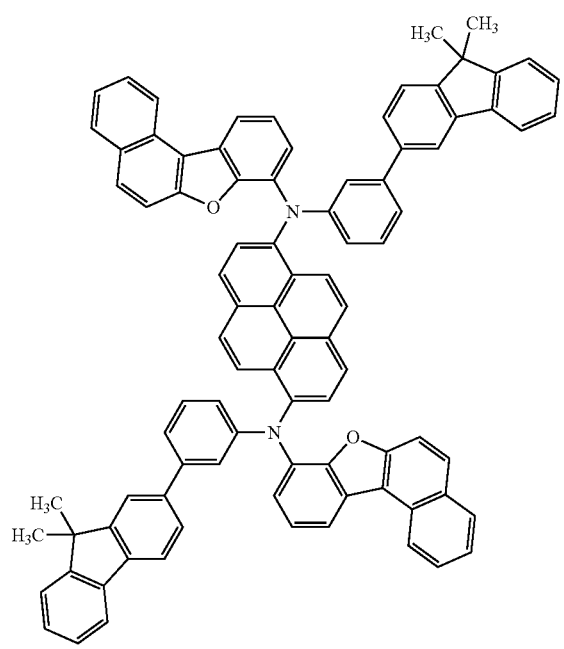
(135)
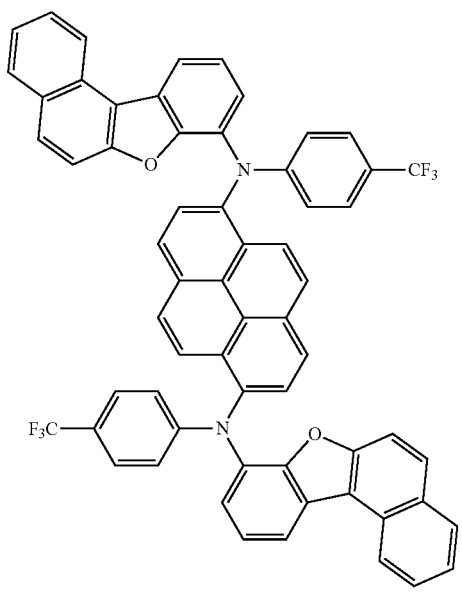
(134)
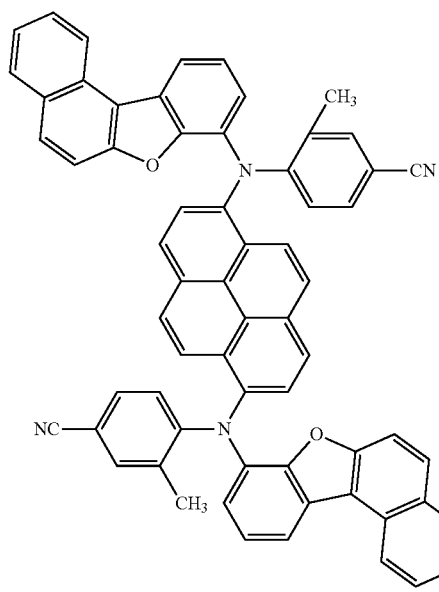
(136)
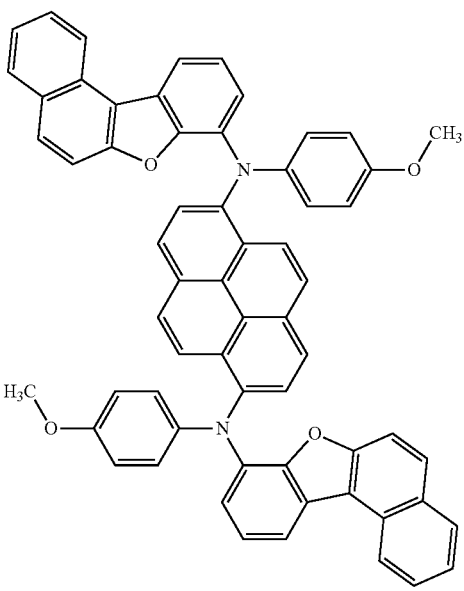

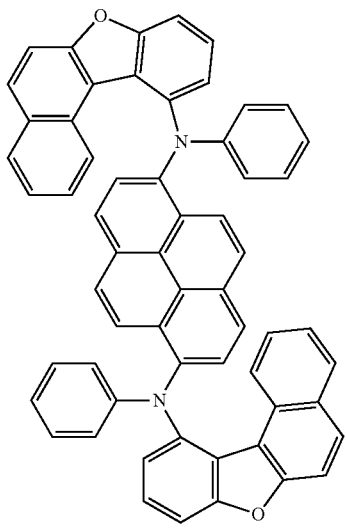

(137)

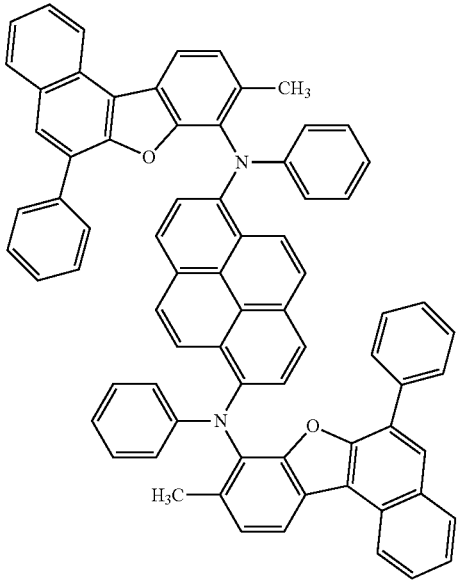

(139)

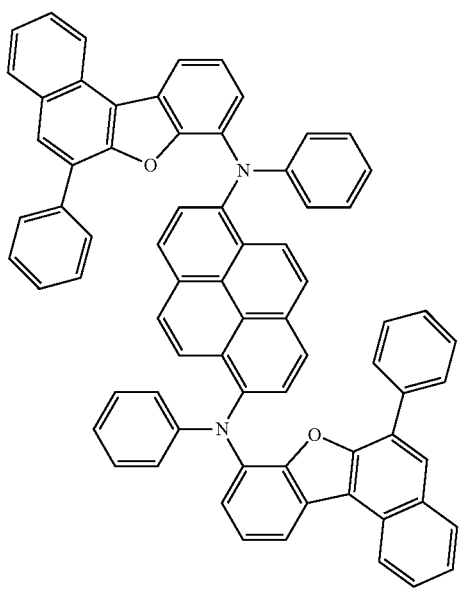

(138)

Note that a variety of reactions can be applied to a method for synthesizing the organic compounds of embodiments of the present invention. For example, synthesis reactions described below enable the synthesis of the organic compound of one embodiment of the present invention represented by General Formula (G1).

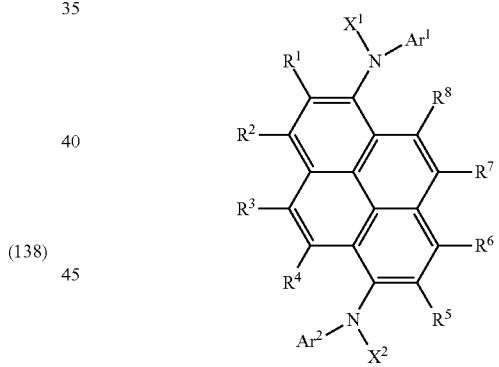

(G1)

An example of a method for synthesizing the organic compound of one embodiment of the present invention represented by General Formula (G1) is described.

<<Method for Synthesizing Organic Compound Represented by General Formula (G1)>>

The organic compound represented by General Formula (G1) can be synthesized by Synthesis Schemes (A-1) and (A-2) shown below. In other words, a pyrene compound (Compound 1), arylamine (Compound 2), and arylamine (Compound 3) are coupled as shown in Synthesis Scheme (A-1) to obtain a pyrene compound (Compound 4), and then the pyrene compound (Compound 4), halogenated aryl (Compound 5), and halogenated aryl (Compound 6) are coupled as shown in Synthesis Scheme (A-2), whereby the organic compound (G1) of one embodiment of the present invention can be obtained.

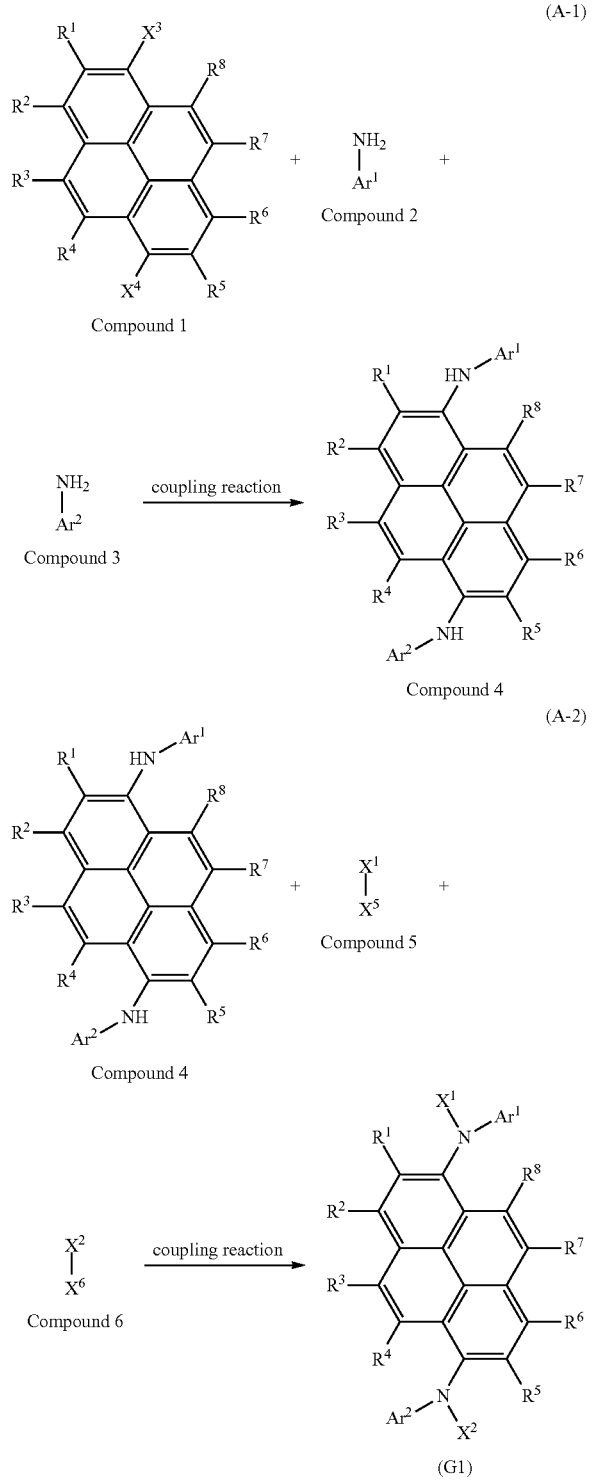

In Synthesis Schemes (A-1) and (A-2), $Ar^1$ and $Ar^2$ separately represent a substituted or unsubstituted aryl group having 6 to 13 carbon atoms forming a ring; $X^3$ to $X^6$ separately represent halogen, a trifluoromethanesulfonate group, a boronic acid group, an organoboron group, a halogenated magnesium group, tin, an organotin group, or the like; $R^1$ to $R^8$ separately represent a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, or a substituted or unsubstituted aryl group having 6 to 10 carbon atoms; and $X^1$ and $X^2$ separately represent a substituted or unsubstituted benzo[b]naphtho[1,2-d]furanyl group. Note that in Synthesis Schemes (A-1) and (A-2), Compound 2 and Compound 3 (i.e., $Ar^1$ and $Ar^2$) are preferably the same and Compound 5 and Compound 6 (i.e., $X^1$ and $X^2$, and $X^5$ and $X^6$) are preferably the same.

In the case where the Buchwald-Hartwig reaction using a palladium catalyst is employed in Synthesis Schemes (A-1) and (A-2), $X^3$ to $X^6$ preferably represent halogen or a triflate group, and the halogen is preferably iodine, bromine, or chlorine. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxybiphenyl can be used. In addition, in the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, or the like can be used as a solvent. Note that reagents that can be used in the reaction are not limited thereto.

The reaction employed in Synthesis Schemes (A-1) and (A-2) is not limited to the Buchwald-Hartwig reaction. The Migita-Kosugi-Stille coupling reaction using an organotin compound, a coupling reaction using a Grignard reagent, the Ullmann reaction using copper or a copper compound, or the like can also be used.

The method for synthesizing the organic compound (G1) of one embodiment of the present invention is not limited to Synthesis Schemes (A-1) and (A-2). The organic compound (G1) of one embodiment of the present invention can also be obtained in such a manner that a benzo[b]naphtho[1,2-d]furan compound and the amine compound (Compound 2 or Compound 3) are coupled to obtain an amine body of the benzo[b]naphtho[1,2-d]furan compound, and then the amine body of the benzo[b]naphtho[1,2-d]furan compound and the pyrene compound (Compound 1) are coupled.

Although the example of the method for synthesizing the organic compound of one embodiment of the present invention is described above, the present invention is not limited to the example and another synthesis method can be used.

The organic compound of one embodiment of the present invention emits blue light with high color purity. Blue light emission having chromaticity near the blue-color chromaticity defined by the national television standards committee (NTSC), i.e., (x, y)=(0.14, 0.08), can be obtained. In addition, the organic compound of one embodiment of the present invention has a long lifetime. Furthermore, the organic compound of one embodiment of the present invention emits fluorescence, and thus can be used as a light-emitting material or a light-emitting substance for a light-emitting element.

Thus, the use of the organic compound of one embodiment of the present invention can achieve a light-emitting element that emits blue light with high color purity and has a long lifetime, a light-emitting device, an electronic appliance, or a lighting device. In addition, the use of the organic compound of one embodiment of the present invention can provide a light-emitting element, a light-emitting device, an electronic appliance, or a lighting device that has high emission efficiency.

Note that the structure described in this embodiment can be combined as appropriate with any of the structures described in the other embodiments.

Embodiment 2

In this embodiment, a light-emitting element in which the organic compound described in Embodiment 1 as one embodiment of the present invention is used for a light-emitting layer is described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113.

When voltage is applied to such a light-emitting element, holes injected from the first electrode 101 side and electrons injected from the second electrode 103 side recombine in the light-emitting layer 113 to raise a light-emitting substance to an excited state. The light-emitting substance in the excited state emits light when it returns to the ground state.

The hole-injection layer 111 included in the EL layer 102 contains a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer (E) 116 contains a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is fabricated is described below.

As the first electrode (anode) 101 and the second electrode (cathode) 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

A substance having a high hole-transport property is preferably used for the hole-injection layer 111, the hole-transport layer 112, and the charge-generation layer (E) 116. Specific examples of the substance having a hole-transport property include aromatic amine compounds such as 4,4'-bis[N-(1-naphthyl)-N-phenylamino]biphenyl (abbreviation: NPB or a-NPD), N,N'-bis(3-methylphenyl)-N,N'-diphenyl-[1,1'biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $10^{-6}$ cm$^2$/Vs or higher. Note that any substance other than the substances listed here may be used as long as the hole-transport property is higher than the electron-transport property.

As the substance having a high hole-transport property, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacryla mide] (abbreviation: PTPDMA), or poly[N,N'-bis(4-butylphenyl)-N,N'-bis(phenyl)benzidine] (abbreviation: Poly-TPD) can also be used.

For the hole-injection layer 111 and the charge-generation layer (E) 116, an acceptor substance is preferably used. Specific examples of the acceptor substance include transition metal oxides and oxides of metals belonging to Groups 4 to 8 of the periodic table. Specifically, molybdenum oxide is particularly preferable.

The light-emitting layer 113 is a layer containing a light-emitting substance. The light-emitting layer 313 may contain only a light-emitting substance; alternatively, an emission center substance (guest material) may be dispersed in a host material in the light-emitting layer 313. Note that in the case where a host material and a guest material are contained in the light-emitting layer 113, the host material preferably has triplet excitation energy higher than that of the guest material.

There is no particular limitation the material that can be used as the light-emitting substance and the emission center substance in the light-emitting layer 313, and light emitted from these substances may be either fluorescence or phosphorescence. Thus, the organic compound of one embodiment of the present invention can be used for the light-emitting layer 313. Besides, for example, substances given below that emit fluorescence or phosphorescence can be given as the light-emitting substance and the emission center substance.

Examples of the substance emitting fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9- anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amin e (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinit rile (abbreviation: DCM1), 2-{2-methyl-6-[2-(2,3,6,7-tetrahydro-1H,5H-benzo[ij]quinolizin-9-yl)ethenyl]-4H-pyra n-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-d iamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinoli zin-9-yl)ethenyl]-4H-pyran-4-ylidene}propanedinitrile (abbreviation: BisDCJTM).

Examples of the substance emitting phosphorescence include bis[2-(3',5'-bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato) (monophenanthroline) terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: [Ir(tppr)$_2$(dpm)], (acetylacetonato)bis(6-tert-butyl-4-phenylpyrimidinato)iridium (III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum(II) (abbreviation: PtOEP), tris(1,3-diphenyl-1,3-propanedionato) (monophenanthroline)europium(III) (abbreviation: Eu(DBM)$_3$(Phen)), and tris[1-(2-thenyl)-3,3,3-trifluoroacetonato] (monophenanthroline)europium(III) (abbreviation: Eu(TTA)$_3$(Phen)).

As the light-emitting substance, a thermally activated delayed fluorescence (TADF) material that converts triplet excitation energy into luminescence and exhibits thermally activated delayed fluorescence can also be used. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer. Specific examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ).

Preferable examples of the substance (i.e., host material) used for dispersing the organometallic iridium complex given above as the substance emitting phosphorescence include compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

The electron-transport layer 114 is a layer containing a substance having a high electron-transport property. For the electron-transport layer 114, a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. A heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $10^{-6}$ cm$^2$/Vs or higher. Note that any substance other than the substances listed here may be used for the electron-transport layer 114 as long as the electron-transport property is higher than the hole-transport property.

Furthermore, the electron-transport layer 114 is not limited to a single layer, and may be a stack of two or more layers each containing any of the substances given above.

The electron-injection layer 115 contains a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. The substances for forming the electron-transport layer 114, which are given above, can also be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specific examples are an alkali metal, an alkaline earth metal, and a rare earth metal are preferable, and lithium, cesium, magnesium, calcium, erbium, and ytterbium. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, electron-injection layer 115, and charge-generation layer (E) 116 can be formed by a method such as an evaporation method (e.g., a vacuum evaporation method), an ink-jet method, or a coating method.

In the above-described light-emitting element, current flows because of a potential difference generated between the first electrode 101 and the second electrode 103 and holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The organic compound of one embodiment of the present invention is used for part of the above-described light-emitting element, so that the light-emitting element can emit blue fluorescence with high color purity and have a long lifetime.

Note that the light-emitting element described in this embodiment is an example of a light-emitting element fabricated using the organic compound of one embodiment of the present invention. As a light-emitting device including the above-described light-emitting element, a passive matrix light-emitting device and an active matrix light-emitting device can be fabricated. It is also possible to fabricate a light-emitting device with a microcavity structure including a light-emitting element described in another embodiment, which is different from the above-described light-emitting element. Each of the light-emitting devices is included in the present invention.

Note that there is no particular limitation on the structure of the transistor (FET) in the case of fabricating the active matrix light-emitting device. For example, a staggered FET or an inverted staggered FET can be used as appropriate. A driver circuit formed over a FET substrate may be formed of both an n-type FET and a p-type FET or only either an n-type FET or a p-type FET. Furthermore, there is no particular limitation on the crystallinity of a semiconductor film used for the FET. For example, either an amorphous semiconductor film or a crystalline semiconductor film can be used. Examples of a semiconductor material include Group IV semiconductors (e.g., silicon and gallium), compound semiconductors (including oxide semiconductors), and organic semiconductors.

Note that the structure described in this embodiment can be combined as appropriate with any of the structures described in the other embodiments.

Embodiment 3

In this embodiment, as one embodiment of the present invention, a light-emitting element (hereinafter referred to as tandem light-emitting element) in which a charge-generation layer is provided between a plurality of EL layers is described.

Figure 2A:
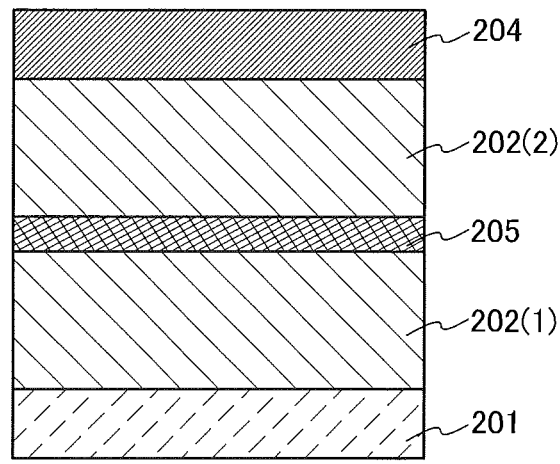
FIGS. 2A and 2B each illustrate a structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, all or any of the plurality of EL layers (the first EL layer 202(1) and the second EL layer 202(2)) may have structures similar to those described in Embodiment 2. In other words, the structures of the first EL layer 202(1) and the second EL layer 202(2) may be the same or different from each other and can be similar to those of the EL layers described in Embodiment 2.

In addition, a charge-generation layer (I) 205 is provided between the plurality of EL layers (the first EL layer 202(1) and the second EL layer 202(2)). The charge-generation layer (I) 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer (I) 205 injects electrons into the first EL layer 202(1) and injects holes into the second EL layer 202(2).

Note that in terms of light extraction efficiency, the charge-generation layer (I) 205 preferably has a property of transmitting visible light (specifically, the charge-generation layer (I) 205 has a visible light transmittance of 40% or more). The charge-generation layer (I) 205 functions even when it has lower conductivity than the first electrode 201 or the second electrode 204.

The charge-generation layer (I) 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances listed here are mainly ones that have a hole mobility of $10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetra-fluoroquinodimethane (abbreviation: F$_4$-TCNQ), chloranil, and the like can be given. Transition metal oxides can also be given. Oxide of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer (I) 205 by using any of the above materials can suppress a drive voltage increase caused by the stack of the EL layers.

Figure 2B:
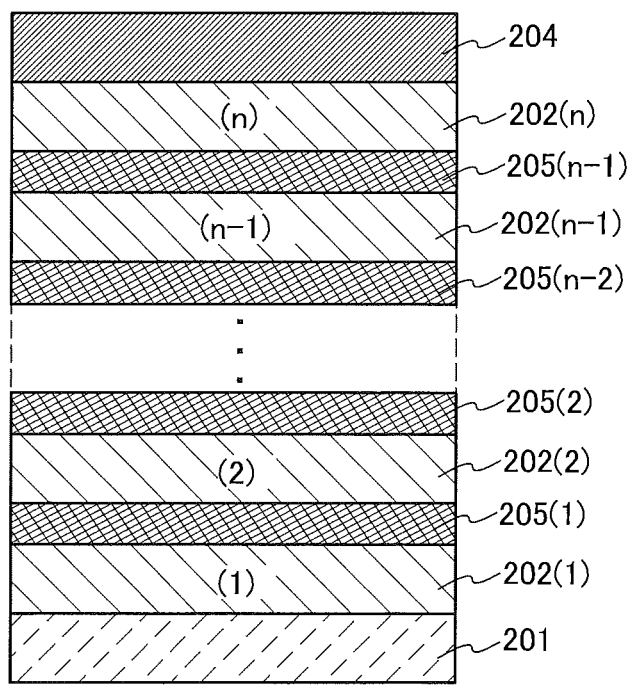

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (I) (205(1) to 205(n−1)) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, which results in homogeneous light emission in a large area. In addition, a low-power-consumption light-emitting device that can be driven at low voltage can be achieved.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary colors" refer to colors that can produce an achromatic color when mixed. In other words, emission of white light can be obtained by mixture of light emitted from substances whose emission colors are complementary colors.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

In this embodiment, a light-emitting device including a light-emitting element in which the organic compound of one embodiment of the present invention is used for a light-emitting layer is described.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Figure 3A:
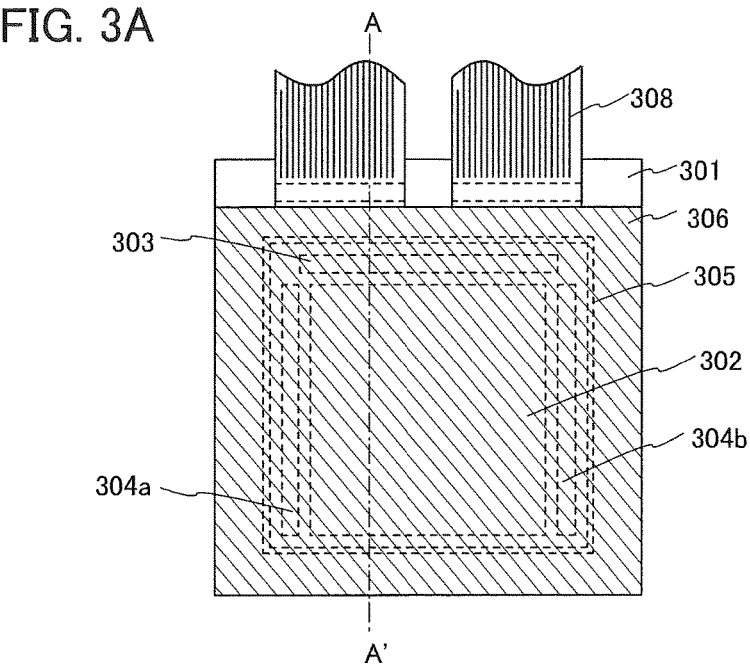
FIGS. 3A and 3B illustrate a light-emitting device.
Figure 3B:
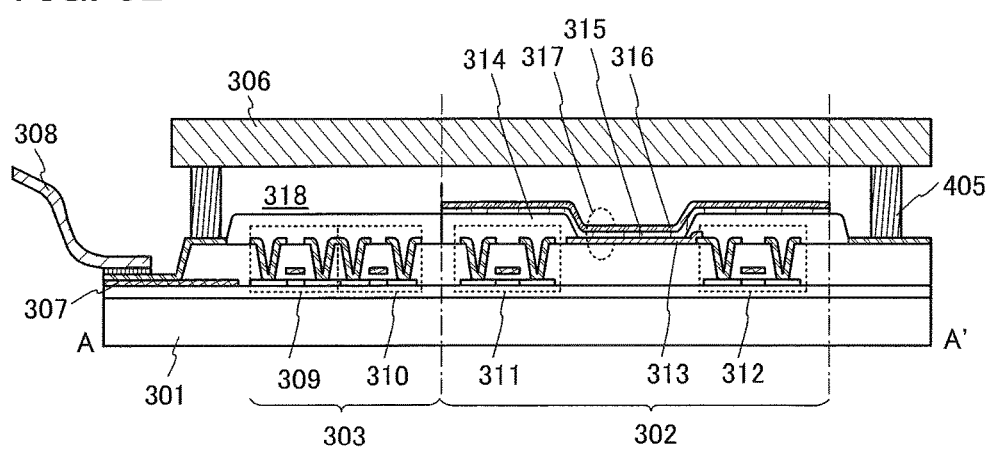

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example where a CMOS circuit is formed, which is a combination of an n-channel FET 309 and a p-channel FET 310. Note that any of various circuits such as a CMOS circuit, a PMOS circuit, or an NMOS circuit can be used as a circuit included in the driver circuit portion. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 that is electrically connected to a wiring (a source electrode or a drain electrode) of the current control FET 312. Note that an insulator 314 is formed to cover end portions of the first electrode (anode) 313. In this embodiment, the insulator 314 is formed using a positive photosensitive acrylic resin.

The insulator 314 preferably has a curved surface with curvature at an upper end portion or a lower end portion thereof in order to obtain favorable coverage by a film that is to be stacked over the insulator 314. Note that the insulator 514 can be formed using, for example, either a negative photosensitive resin or a positive photosensitive resin. The material of the insulator 314 is not limited to an organic compound and an inorganic compound such as silicon oxide or silicon oxynitride can also be used.

An EL layer 315 and a second electrode (cathode) 316 are stacked over the first electrode (anode) 313. In the EL layer 315, at least a light-emitting layer is provided, and the light-emitting layer contains the organic compound of one embodiment of the present invention. In the EL layer 315, a hole-injection layer, a hole-transport layer, an electron-transport layer, an electron-injection layer, a charge-generation layer, and the like can be provided as appropriate in addition to the light-emitting layer.

The stacked structure of the first electrode (anode) 313, the EL layer 315, and the second electrode (cathode) 316 forms a light-emitting element 317. For the first electrode (anode) 313, the EL layer 315, and the second electrode (cathode) 316, any of the materials listed in Embodiment 2 can be used. Although not illustrated, the second electrode (cathode) 316 is electrically connected to the FPC 308 that is an external input terminal.

Although the cross-sectional view of FIG. 3B illustrates only one light-emitting element 317, a plurality of light-emitting elements is arranged in matrix in the pixel portion 302. Light-emitting elements that emit light of three kinds of colors (R, G, and B) are selectively formed in the pixel portion 302, whereby a light-emitting device capable of full color display can be obtained. Alternatively, a light-emitting device that is capable of full color display may be fabricated by a combination with color filters.

Furthermore, the sealing substrate 306 is attached to the element substrate 301 with the sealant 305, so that the light-emitting element 317 is provided in a space 318 surrounded by the element substrate 301, the sealing substrate 306, and the sealant 305. The space 318 may be filled with an inert gas (e.g., nitrogen or argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber reinforced plastic (FRP), poly(vinyl fluoride) (PVF), polyester, acrylic, or the like can be used. In the case where glass frit is used as the sealant, the element substrate 301 and the sealing substrate 306 are preferably glass substrates in terms of adhesion.

As described above, the active matrix light-emitting device can be fabricated.

Note that the structure described in this embodiment can be combined as appropriate with any of the structures described in the other embodiments.

Embodiment 5

In this embodiment, examples of a variety of electronic appliances that are completed using a light-emitting device will be described with reference to FIGS. 4A to 4D. The light-emitting device is fabricated using the light-emitting element of one embodiment of the present invention.

Examples of electronic appliances that include the light-emitting device include television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, and large game machines such as pin-ball machines. Specific examples of the electronic appliances are shown in FIGS. 4A to 4D.

Figure 4A:
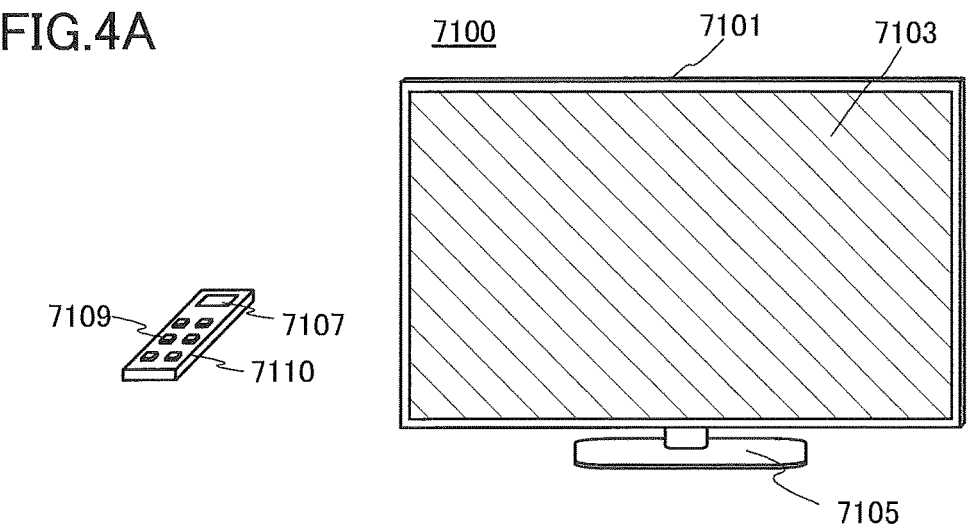
FIGS. 4A to 4D illustrate electronic appliances.

FIG. 4A illustrates an example of a television device. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
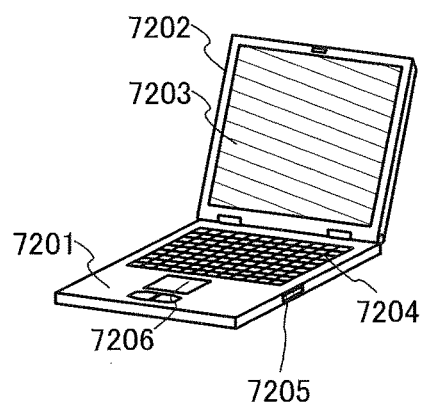

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device for the display portion 7203.

Figure 4C:
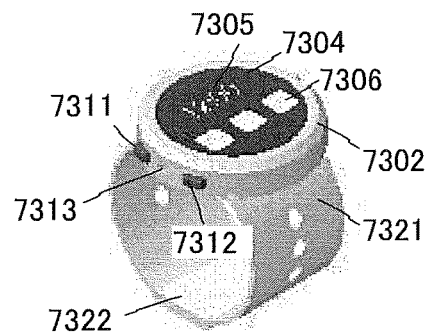

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region.

The display panel 7304 can display an icon 7305 indicating time, another icon 7306, and the like.

The smart watch in FIG. 4C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 4D:
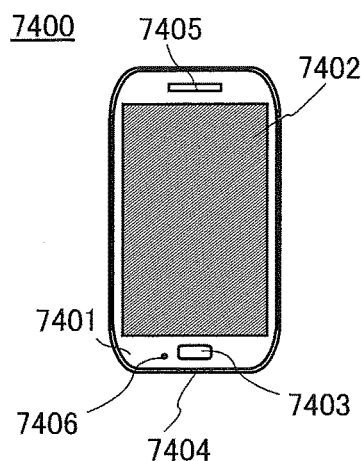

FIG. 4D illustrates an example of a mobile phone. A mobile phone 7400 includes a display portion 7402 incorporated in a housing 7401, an operation button 7403, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 4D is touched with a finger or the like, data can be input to the mobile phone 7400. In addition, operations such as making a call and composing an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, when a backlight or a sensing light source that emits near-infrared light is provided in the display portion, an image of a finger vein, a palm vein, or the like can be taken.

As described above, the electronic appliances can be obtained using the light-emitting device of one embodiment of the present invention. The light-emitting device has a remarkably wide application range, and thus can be used for electronic appliances in a variety of fields.

Note that the structure described in this embodiment can be combined as appropriate with any of the structures described in the other embodiments.

Embodiment 6

In this embodiment, examples of a lighting device in which a light-emitting device including the organic compound of one embodiment of the present invention is used are described with reference to FIG. 5.

Figure 5:
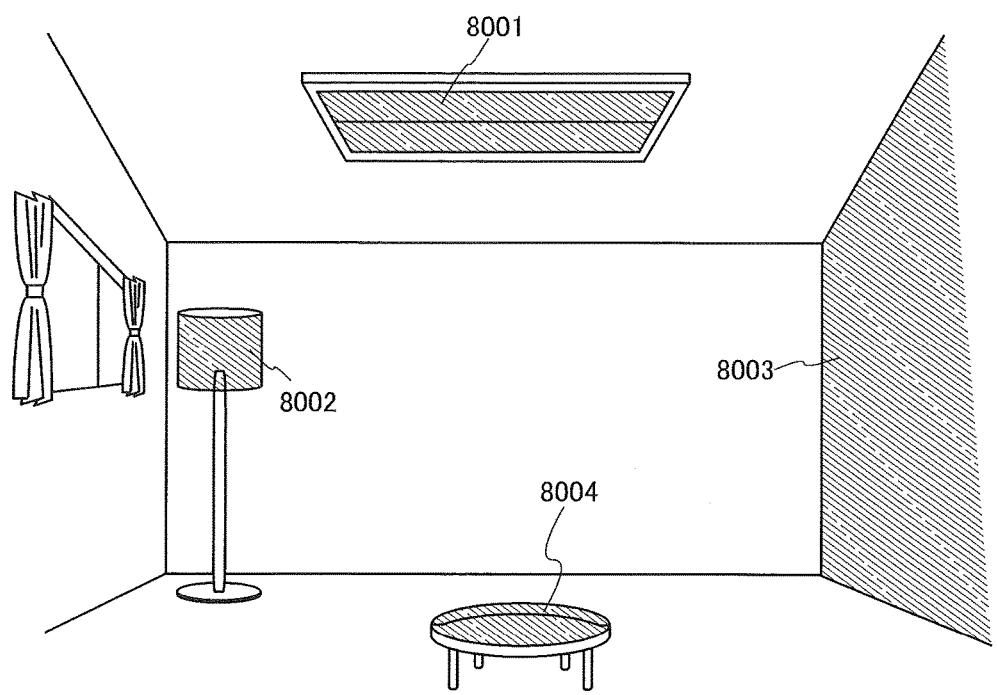
FIG. 5 illustrates lighting devices.

FIG. 5 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. In addition, a wall of the room may be provided with a large-sized lighting device 8003.

When the light-emitting device is used for a table by being used as a surface of a table, a lighting device 8004 that has a function as a table can be obtained. When the light-emitting device is used as part of other furniture, a lighting device that has a function as the furniture can be obtained.

As described above, a variety of lighting devices in which the light-emitting device is used can be obtained. Note that these lighting devices are also embodiments of the present invention.

Note that the structure described in this embodiment can be combined as appropriate with any of the structures described in the other embodiments.

Example 1

Synthesis Example 1

In this example, a method for synthesizing N,N'-(pyrene-1,6-diyl)bis[(N-phenylbenzo[b]naphtho[1,2-d]furan)-6-amine] (abbreviation: 1,6BnfAPrn), an organic compound of one embodiment of the present invention represented by Structural Formula (100) in Embodiment 1, is described. Note that a structure of 1,6BnfAPrn is shown below.

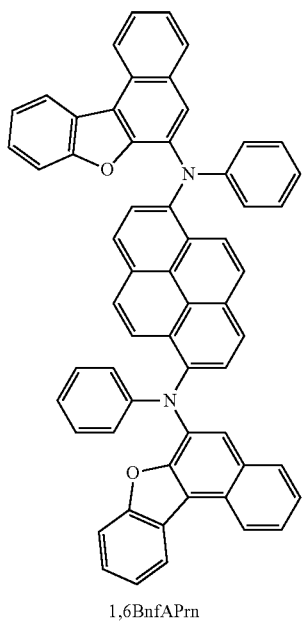

1,6BnfAPrn

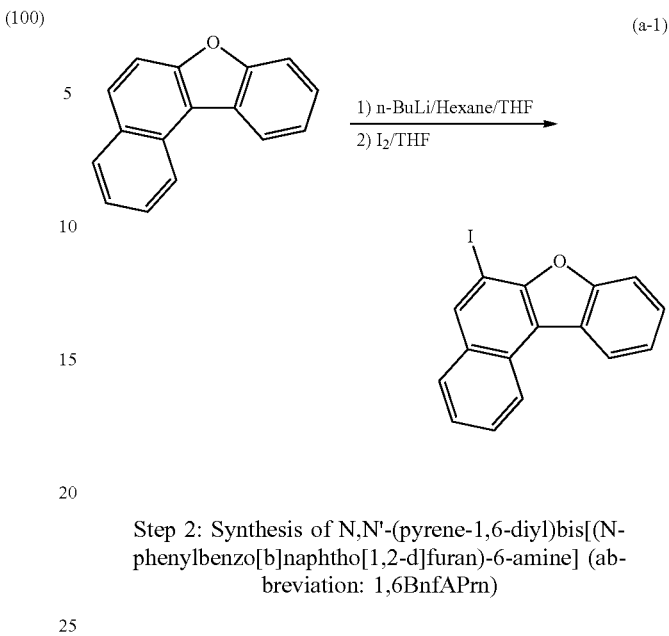

Step 2: Synthesis of N,N'-(pyrene-1,6-diyl)bis[(N-phenylbenzo[b]naphtho[1,2-d]furan)-6-amine] (abbreviation: 1,6BnfAPrn)

Into a 300 mL three-neck flask were put 1.2 g (3.3 mmol) of 1,6-dibromopyrene, 1.5 g (15 mmol) of sodium tert-butoxide, and 80 mg (0.14 mmol) of bis(dibenzylideneacetone)palladium(0), and the air in the flask was replaced with nitrogen. Then, 15 mL of toluene, 0.6 mL of aniline, and 0.5 mL of tri(tert-butyl)phosphine (10% hexane solution) were added to the mixture.

The resulting mixture was stirred at 80° C. for 5 hours, and then 2.3 g (6.6 mmol) of 6-iodobenzo[b]naphtho[1,2-d]furan, 0.50 g (5.1 mmol) of sodium tert-butoxide, 0.5 mL of tri(tert-butyl)phosphine (10% hexane solution), and 80 mg (0.14 mmol) of bis(dibenzylideneacetone)palladium(0) were added to the mixture. The resulting mixture was stirred at 80° C. for 17 hours. After a predetermined period of time, the resulting mixture was filtered through Celite (Catalog No. 531-16855 produced by Wako Pure Chemical Industries, Ltd.) to give a filtrate. The obtained filtrate was concentrated to give a solid. The solid was washed with ethanol and toluene to give 1.2 g (1.5 mmol) of a yellow solid of the target substance in 46% yield.

By a train sublimation method, 1.3 g of the obtained yellow solid was purified by sublimation. The purification by sublimation was conducted by heating the yellow solid at 340° C. under a pressure of $1.0 \times 10^{-2}$ Pa or lower. As a result of the purification by sublimation, 0.62 g of a yellow solid was recovered in 51% yield. A synthesis scheme of Step 2 is shown in (a-2).

Step 1: Synthesis of 6-iodobenzo[b]naphtho[1,2-d]furan

Into a 500 mL three-neck flask were put 12 g (55 mmol) of benzo[b]naphtho[1,2-d]furan and 220 mL of tetrahydrofuran, and the air in the flask was replaced with nitrogen. Then, this solution was cooled to +80° C. Then, 40 mL (64 mmol) of n-butyllithium (a 1.6 mol/L n-hexane solution) was dropped into this solution with a syringe at −80° C. After the drop, the resulting solution was stirred at room temperature for 1 hour.

After the stirring, this solution was cooled to −80° C. Then, a solution in which 17 g (66 mmol) of iodine had been dissolved in 60 mL of tetrahydrofuran was dropped into this solution with a dripping funnel at −80° C. After the drop, this solution was stirred for 17 hours while its temperature was returned to room temperature. After the stirring, an aqueous solution of sodium thiosulfate was added to the resulting mixture, and the mixture was stirred for 1 hour. After the stirring, an organic layer of this mixture was washed with water and a saturated aqueous solution of sodium hydrogen carbonate, and then magnesium sulfate was added to the organic layer. The mixture was gravity-filtered to give a filtrate, and then the filtrate was concentrated to give a solid.

The resulting solid was recrystallized from toluene/hexane to give a pale brown solid. Ethanol was added to the resulting solid, irradiation with ultrasonic waves was performed, and a solid was collected by suction filtration to give 11 g (31 mmol) of pale yellow powder of the target substance in 56% yield. A synthesis scheme of Step 1 is shown in (a-1).

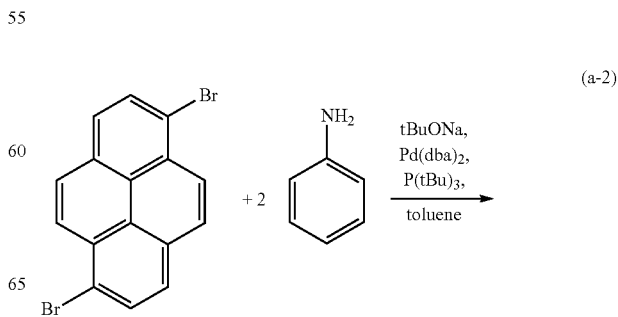

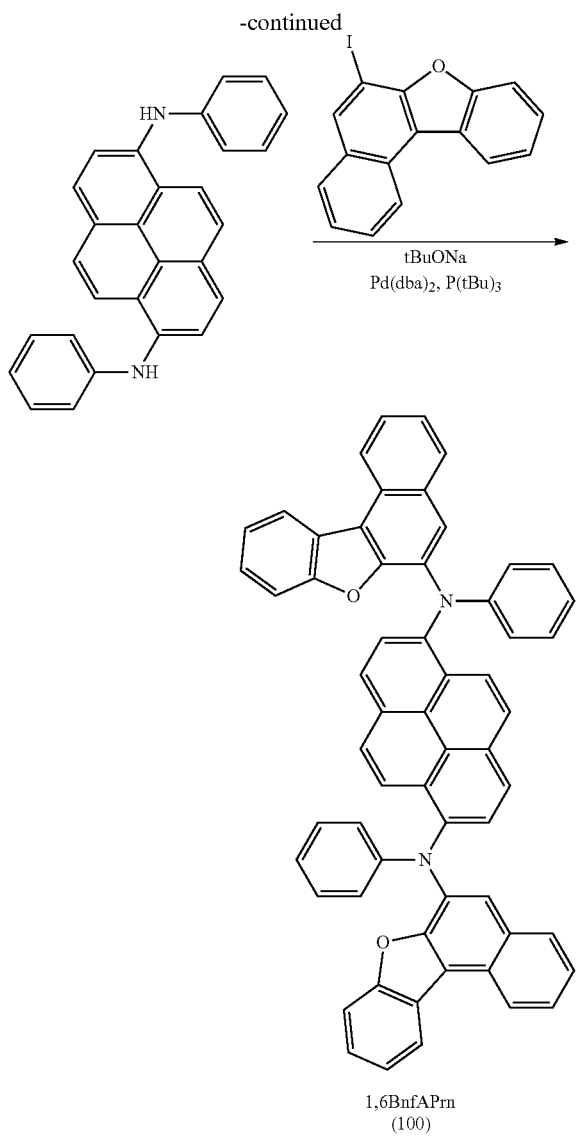

1,6BnfAPrn
(100)

Figure 6A:
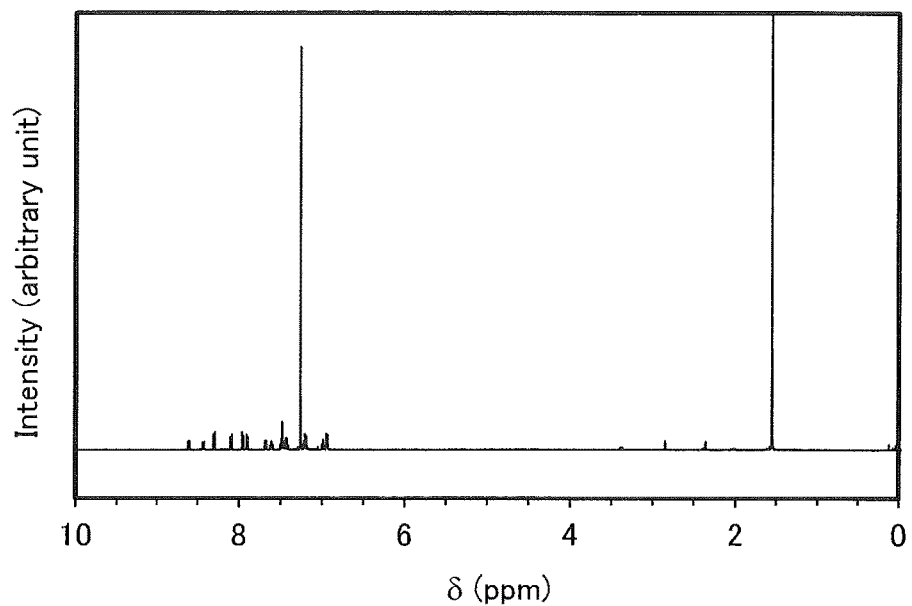
FIGS. 6A and 6B are $^1$H NMR charts of an organic compound represented by Structural Formula (100).
Figure 6B:
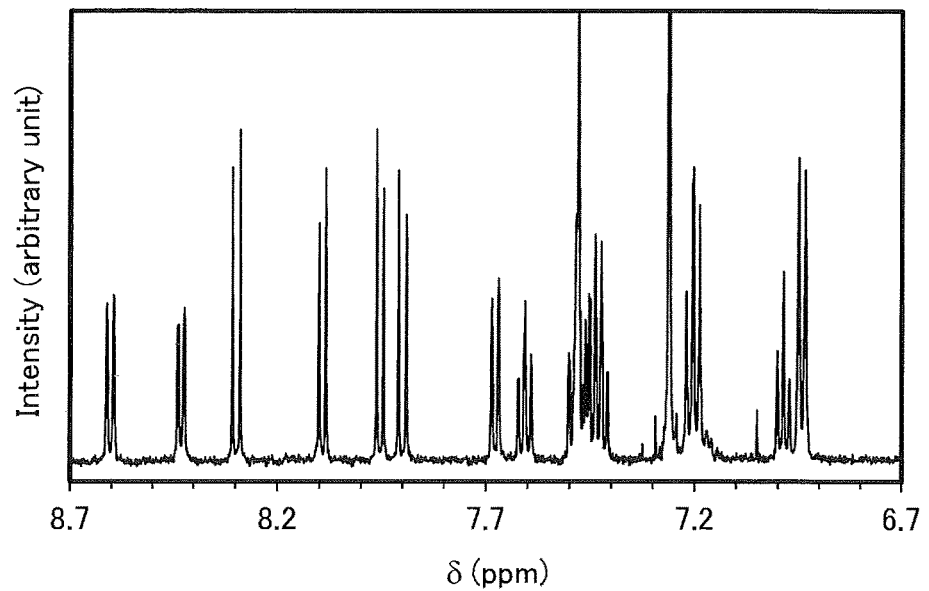

Analysis results by nuclear magnetic resonance ($^1$H-NMR) spectroscopy of the yellow solid obtained in Step 2 are described below. FIGS. 6A and 6B are $^1$H NMR charts. The $^1$H NMR charts revealed that 1,6BnfAPrn, the organic compound of one embodiment of the present invention represented by Structural Formula (100), was obtained in Synthesis Example 1.

$^1$H NMR (CDCl$_3$, 500 MHz): δ=6.94 (d, J=7.5 Hz, 4H), 6.99 (t, J=7.5 Hz, 2H), 7.20 (t, J=7.8 Hz, 4H), 7.41-7.50 (m, 10H), 7.61 (t, J=7.5 Hz, 2H), 7.68 (d, J=8.0 Hz, 2H), 7.90 (d, J=9.5 Hz, 2H), 7.95 (d, J=8.5 Hz, 2H), 8.09 (d, J=8.0 Hz, 2H), 8.30 (d, J=9.0 Hz, 2H), 8.43 (d, J=7.0 Hz, 2H), 8.60 (d, J=8.0 Hz, 2H).

Figure 7A:
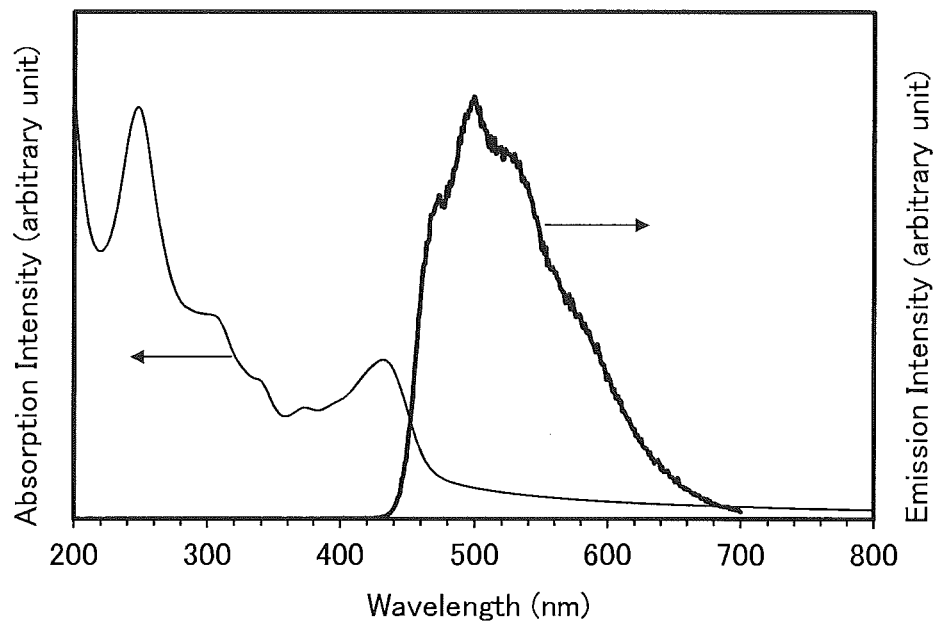
FIGS. 7A and 7B show ultraviolet-visible absorption spectra and emission spectra of the organic compound represented by Structural Formula (100).

Next, an ultraviolet-visible absorption spectrum (hereinafter, simply referred to as "absorption spectrum") and an emission spectrum of 1,6BnfAPrn in a toluene solution were measured. The absorption spectrum was measured at room temperature with an ultraviolet-visible light spectrophotometer (V-550, manufactured by JASCO Corporation) in a state where the toluene solution was put in a quartz cell. The emission spectrum was measured with a fluorescence spectrophotometer (FS920, manufactured by Hamamatsu Photonics Corporation) at room temperature in a state where the toluene solution was put in the quartz cell. FIG. 7A shows measurement results of the absorption spectrum and the emission spectrum. The horizontal axis represents wavelength (nm) and the vertical axis represents absorption intensity (arbitrary unit) and emission intensity (arbitrary unit). In FIG. 7A, two solid lines are shown: a thin line represents the absorption spectrum and a thick line represents the emission spectrum. The absorption spectrum shown in FIG. 7A is a result obtained by subtraction of an absorption spectrum of only toluene in a quartz cell from the measured absorption spectrum of the toluene solution in the quartz cell.

As shown in FIG. 7A, 1,6BnfAPrn that is the organic compound of one embodiment of the present invention has an emission peak at 459 nm, which means that blue light emission was observed in the toluene solution.

Figure 7B:
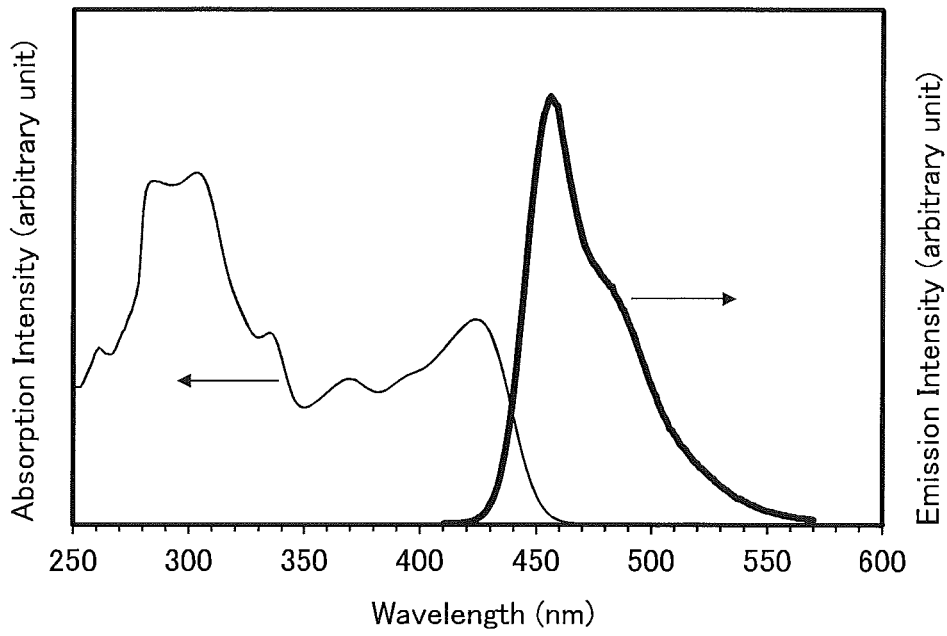

FIG. 7B shows an absorption spectrum and an emission spectrum of a thin film of 1,6BnfAPrn. The absorption spectrum was measured with an ultraviolet-visible spectrophotometer (V-550, produced by JASCO Corporation). The measurement was performed with samples each prepared in such a manner that the thin film was deposited on a quartz substrate. The absorption spectrum was obtained by subtraction of an absorption spectrum of only the quartz substrate from absorption spectra of the thin film on the quartz substrate. In FIG. 7B, the horizontal axis represents wavelength (nm) and the vertical axis represents absorption intensity (arbitrary unit).

Next, 1,6BnfAPrn obtained in this example was analyzed by liquid chromatography mass spectrometry (LC-MS).

In the analysis by LC-MS, liquid chromatography (LC) separation was carried out with UltiMate 3000 manufactured by Thermo Fisher Scientific K.K., and mass spectrometry (MS) analysis was carried out with Q Exactive manufactured by Thermo Fisher Scientific K.K. ACQUITY UPLC BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. A sample was prepared in such a manner that 1,6BnfAPrn was dissolved in toluene at a given concentration and the mixture was diluted with acetonitrile. The injection amount was 10.0 μL.

In the MS analysis, ionization was carried out by an electrospray ionization (ESI) method, and measurement was carried out by targeted-MS$^2$. Conditions of an ion source were set as follows: the flow rates of a sheath gas, an Aux gas, and a Sweep gas were 50, 10, and 0, respectively, the spray voltage was 3.5 kV, the capillary temperature was 350° C., the S lens voltage was 55.0, and the HESI heater temperature was 350° C. The resolution was 70000, the AGC target was 3e6, the mass range was m/z=112 to 1690, and the detection was performed in a positive mode.

Figure 24A:
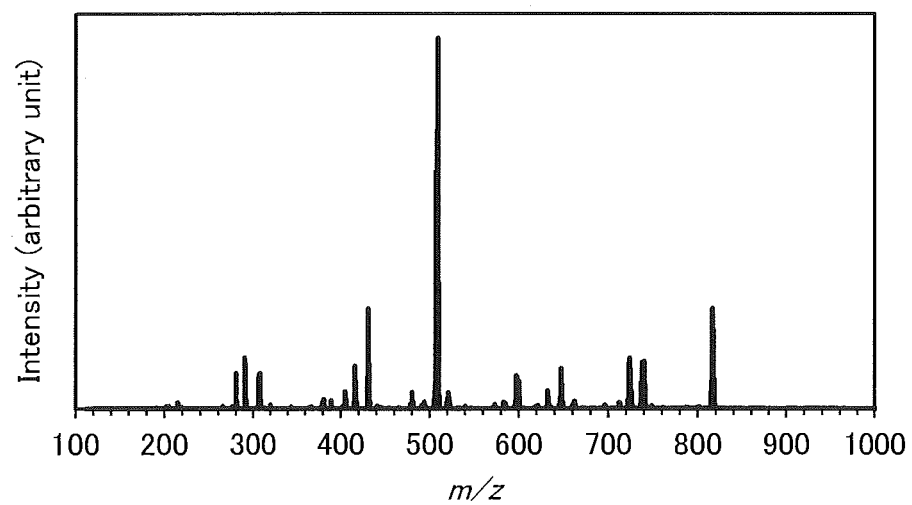
FIGS. 24A and 24B show results of LC-MS analysis of the organic compound represented by Structural Formula (100).
Figure 24B:
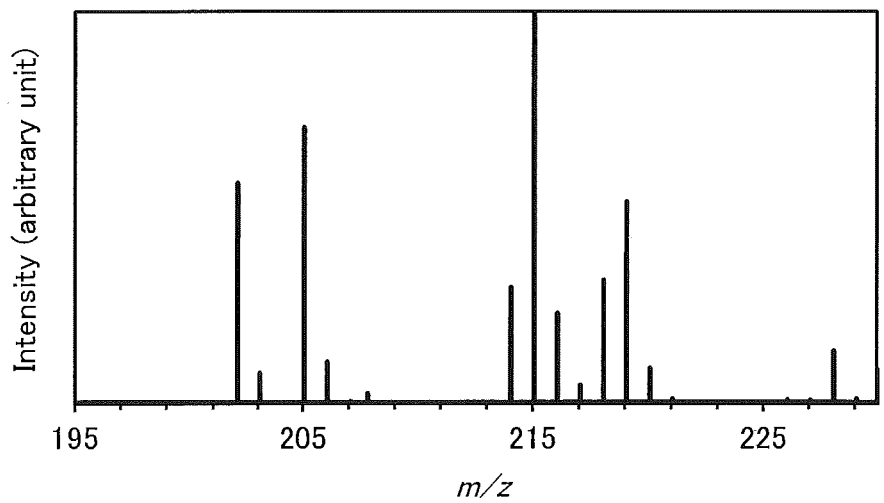

A component with m/z of 817.28250±10 ppm that underwent the ionization under the above-described conditions was collided with an argon gas in a collision cell to dissociate into product ions, and MSMS measurement was carried out. FIGS. 24A and 24B show detection results of ions, which were generated under a normalized collision energy (NCE) for the collision with argon of 50, with a Fourier transform mass spectrometer (FT MS).

The results in FIGS. 24A and 24B demonstrate that product ions of 1,6BnfAPrn, the organic compound of one embodiment of the present invention represented by Structural Formula (100), are detected at around m/z=218 and m/z=202. Note that the results in FIGS. 24A and 24B show characteristics derived from 1,6BnfAPrn and thus can be regarded as important data for identifying 1,6BnfAPrn contained in a mixture.

The product ion around m/z=218 is presumed to be a cation derived from benzo[b]naphtho[1,2-d]furan in the compound represented by Structural Formula (100), and this indicates a partial structure of 1,6BnfAPrn of one embodiment of the present invention. In addition, the product ion around m/z=202 is presumed to be a cation derived from pyrene, and this indicates a partial structure of 1,6BnfAPrn, the organic compound of one embodiment of the present invention.

Example 2

Synthesis Example 2

In this example, a method for synthesizing N,N'-(pyrene-1,6-diyl)bis[(N-phenylbenzo[b]naphtho[1,2-d]furan)-8-amine] (abbreviation: 1,6BnfAPrn-02), an organic compound of one embodiment of the present invention represented by Structural Formula (101) in Embodiment 1, is described. Note that a structure of 1,6BnfAPrn-02 is shown below.

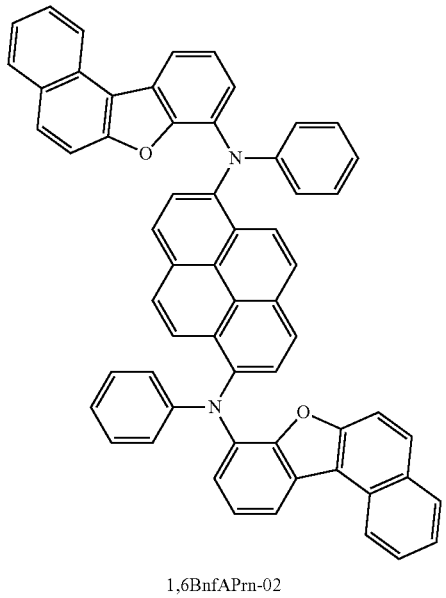

(101)

1,6BnfAPrn-02

Step 1: Synthesis of N,N'-(pyrene-1,6-diyl)bis[(N-phenylbenzo[b]naphtho[1,2-d]furan)-8-amine] (abbreviation: 1,6BnfAPrn-02)

Into a 50 mL three-neck flask were put 0.71 g (2.0 mmol) of 1,6-dibromopyrene, 1.0 g (0.10 mmol) of sodium tert-butoxide, and 50 mg (0.087 mmol) of bis(dibenzylideneacetone)palladium(0), and the air in the flask was replaced with nitrogen. Then, 10 mL of toluene, 0.4 mL of aniline, and 0.3 mL of tri(tert-butyl)phosphine (10% hexane solution) were added to the mixture. The resulting mixture was stirred at 80° C. for 3 hours.

After a predetermined period of time, 1.0 g (4.0 mmol) of 8-chlorobenzo[b]naphtho[1,2-d]furan, 0.18 g (0.44 mmol) of 2-dicyclohexylphosphino-2',6'-dimethoxybiphenyl (abbreviation: S-Phos), and 50 mg (0.087 mmol) of bis(dibenzylideneacetone)palladium(0) were added to the mixture. The resulting mixture was stirred at 80° C. for 10 hours. After a predetermined period of time, the resulting mixture was suction-filtered through Celite (Catalog No. 531-16855 produced by Wako Pure Chemical Industries, Ltd.) to give a filtrate. The obtained filtrate was concentrated to give a solid. The solid was recrystallized from toluene/ethanol to give a brown solid.

The obtained solid was purified by silica gel column chromatography. As a developing solvent, a mixed solvent of toluene and hexane in a ratio of 1:3 was used. An obtained fraction was concentrated to give a solid. The solid was recrystallized from toluene to give 1.3 g (1.6 mmol) of a yellow solid of the target substance in 82% yield.

By a train sublimation method, 1.3 g of the obtained yellow solid was purified by sublimation. The purification by sublimation was conducted by heating the yellow solid at 350° C. at an argon flow rate of 10 mL/min under a pressure of 2.6 Pa. As a result of the purification by sublimation, 0.78 g of a yellow solid was recovered in 58% yield. A synthesis scheme of Step 2 is shown in (b-1).

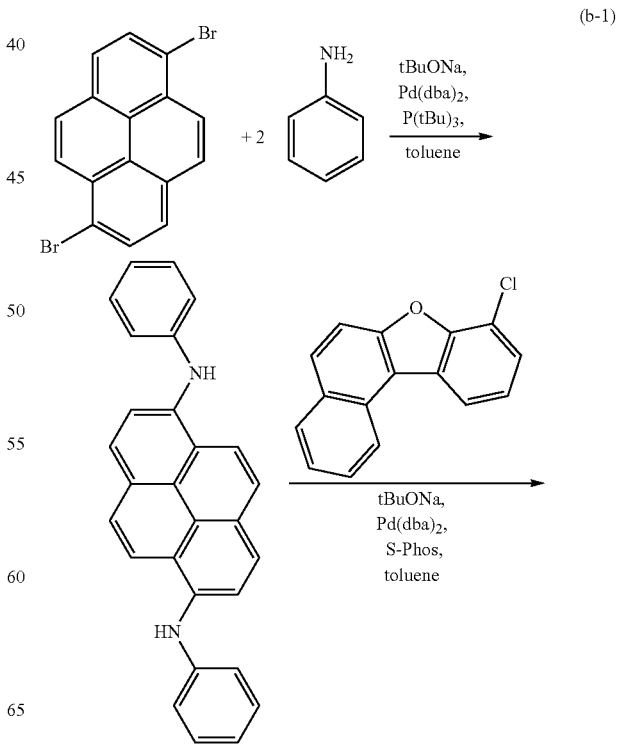

(b-1)

-continued

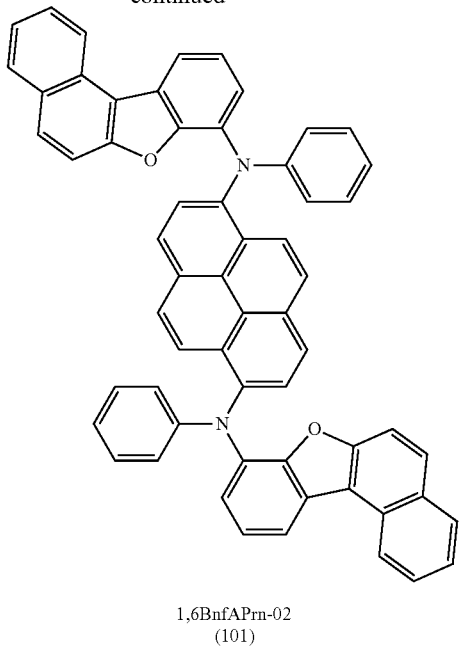

1,6BnfAPrn-02
(101)

Figure 8A:
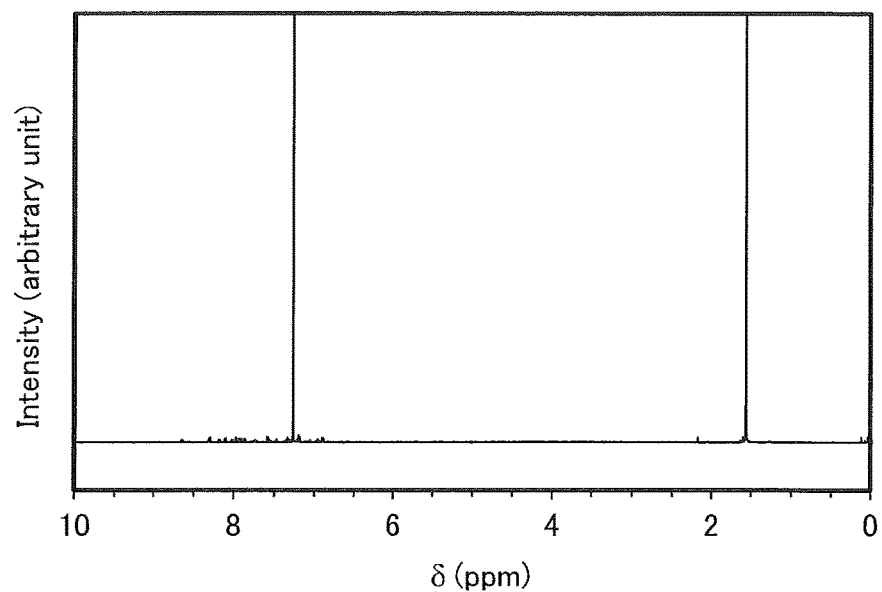
FIGS. 8A and 8B are $^1$H NMR charts of an organic compound represented by Structural Formula (101).
Figure 8B:
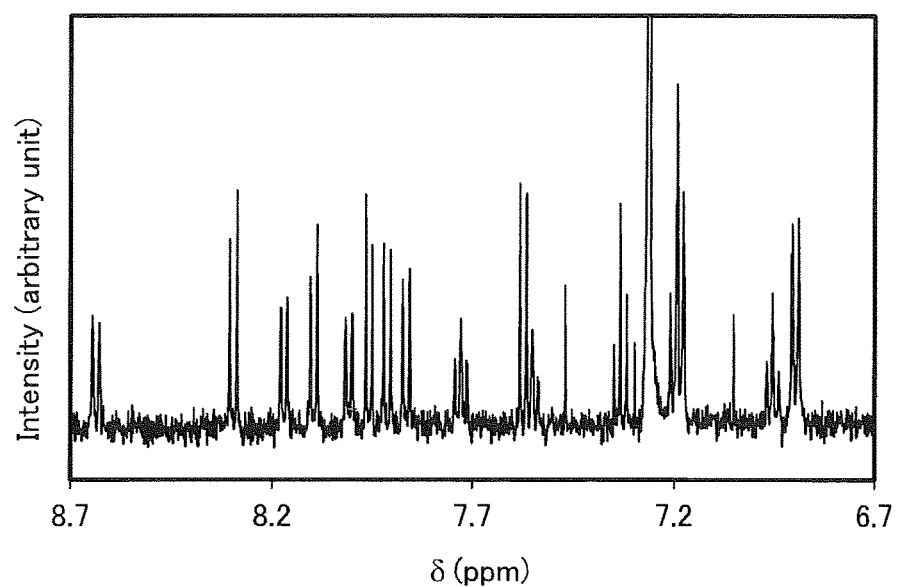

Analysis results by nuclear magnetic resonance ($^1$H-NMR) spectroscopy of the yellow solid obtained in Step 1 are described below. FIGS. 8A and 8B are $^1$H NMR charts. The $^1$H NMR charts revealed that 1,6BnfAPrn-02, which is the organic compound of one embodiment of the present invention represented by Structural Formula (101), was obtained in Synthesis Example 2.

$^1$H NMR(CDCl$_3$, 500 MHz): δ=6.90 (d, J=8.0 Hz, 4H), 6.95 (t, J=7.2 Hz, 2H), 7.19 (t, J=8.0 Hz, 6H), 7.33 (t, J=8.0 Hz, 2H), 7.54 (d, J=8.0 Hz, 2H), 7.57 (d, J=9.0 Hz, 2H), 7.73 (t, J=7.2 Hz, 2H), 7.86 (d, J=9.0 Hz, 2H), 7.91 (d, J=9.0 Hz, 2H), 7.96 (d, J=8.5 Hz, 2H), 8.01 (d, J=9.0 Hz, 2H), 8.10 (d, J=8.5 Hz, 2H), 8.17 (d, J=8.0 Hz, 2H), 8.29 (d, J=9.5 Hz, 2H), 8.64 (d, J=8.5 Hz, 2H).

Figure 9A:
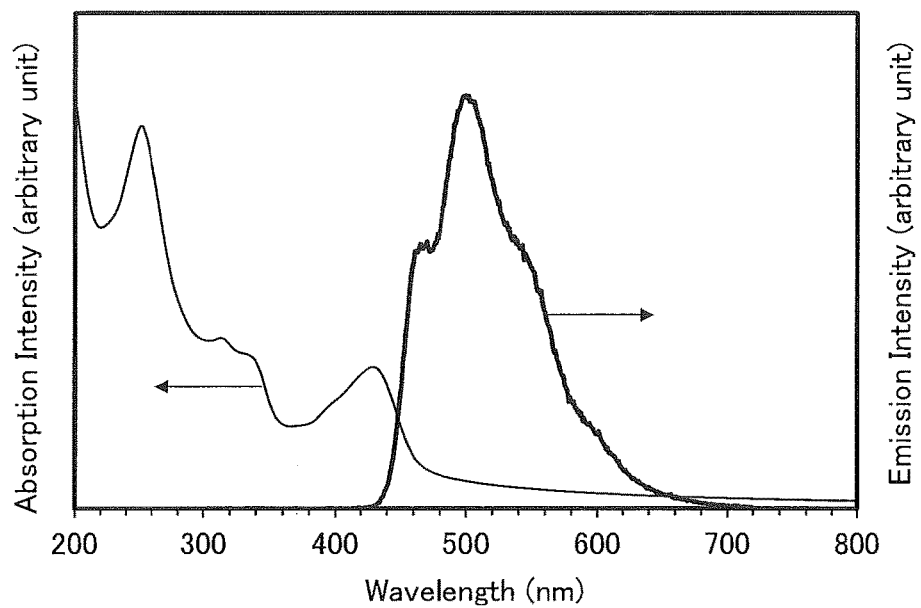
FIGS. 9A and 9B show ultraviolet-visible absorption spectra and emission spectra of the organic compound represented by Structural Formula (101).

Next, an ultraviolet-visible absorption spectrum (hereinafter, simply referred to as "absorption spectrum") and an emission spectrum of 1,6BnfAPrn-02 in a toluene solution were measured. The absorption spectrum was measured at room temperature with an ultraviolet-visible light spectrophotometer (V-550, manufactured by JASCO Corporation) in a state where the toluene solution was put in a quartz cell. The emission spectrum was measured with a fluorescence spectrophotometer (FS920, manufactured by Hamamatsu Photonics Corporation) at room temperature in a state where the toluene solution was put in the quartz cell. FIG. 9A shows measurement results of the absorption spectrum and the emission spectrum. The horizontal axis represents wavelength (nm) and the vertical axis represents absorption intensity and emission intensity. In FIG. 9A, two solid lines are shown: a thin line represents the absorption spectrum and a thick line represents the emission spectrum. The absorption spectrum shown in FIG. 9A is a result obtained by subtraction of an absorption spectrum of only toluene in a quartz cell from the measured absorption spectrum of the toluene solution in the quartz cell.

As shown in FIG. 9A, 1,6BnfAPrn-02 that is the organic compound of one embodiment of the present invention has an emission peak at 453 nm, which means that blue light emission was observed in the toluene solution.

Figure 9B:
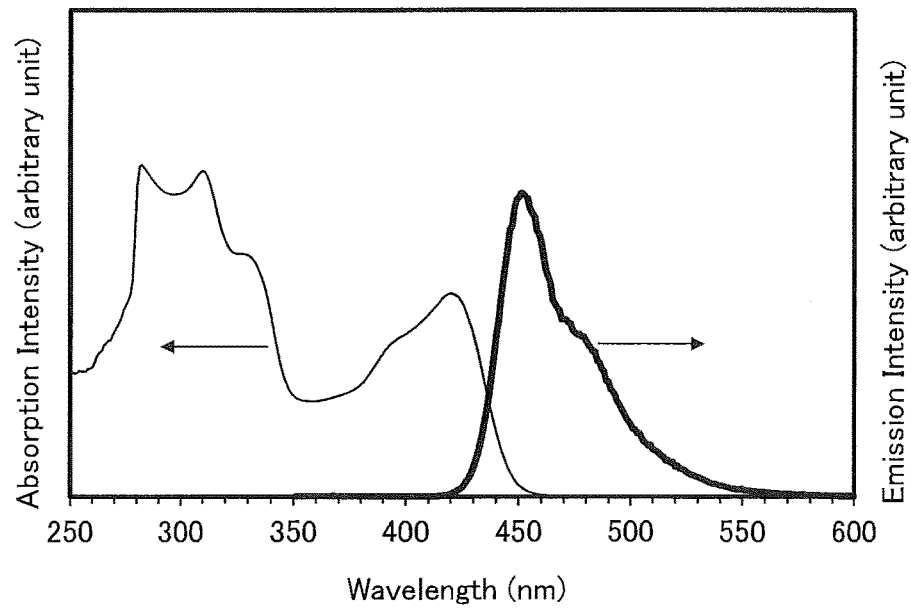

FIG. 9B shows an absorption spectrum and an emission spectrum of a thin film of 1,6BnfAPrn-02. The absorption spectrum was measured with an ultraviolet-visible spectrophotometer (V-550, produced by JASCO Corporation). The measurement was performed with samples each prepared in such a manner that the thin film was deposited on a quartz substrate. The absorption spectrum was obtained by subtraction of an absorption spectrum of only the quartz substrate from absorption spectra of the thin film on the quartz substrate. In FIG. 9B, the horizontal axis represents wavelength (nm) and the vertical axis represents absorption intensity (arbitrary unit).

Next, 1,6BnfAPrn-02 obtained in this example was analyzed by liquid chromatography mass spectrometry (LC-MS).

In the analysis by LC-MS, liquid chromatography (LC) separation was carried out with UltiMate 3000 manufactured by Thermo Fisher Scientific K.K., and mass spectrometry (MS) analysis was carried out with Q Exactive manufactured by Thermo Fisher Scientific K.K. ACQUITY UPLC BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. A sample was prepared in such a manner that 1,6BnfAPrn-02 was dissolved in toluene at a given concentration and the mixture was diluted with acetonitrile. The injection amount was 10.0 μL.

In the MS analysis, ionization was carried out by an electrospray ionization (ESI) method, and measurement was carried out by targeted-MS$^2$. Conditions of an ion source were set as follows: the flow rates of a sheath gas, an Aux gas, and a Sweep gas were 50, 10, and 0, respectively, the spray voltage was 3.5 kV, the capillary temperature was 350° C., the S lens voltage was 55.0, and the HEST heater temperature was 350° C. The resolution was 70000, the AGC target was 3e6, the mass range was m/z=112 to 1690, and the detection was performed in a positive mode.

Figure 25A:
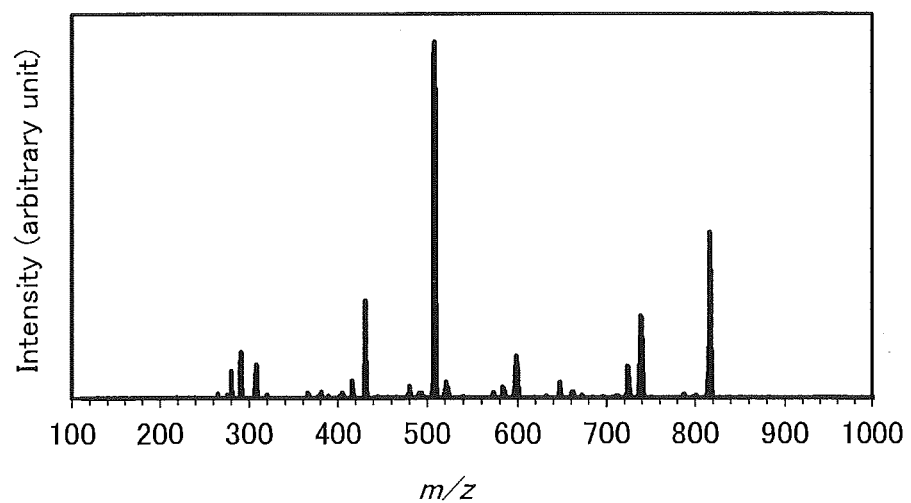
FIGS. 25A and 25B show results of LC-MS analysis of the organic compound represented by Structural Formula (101).
Figure 25B:
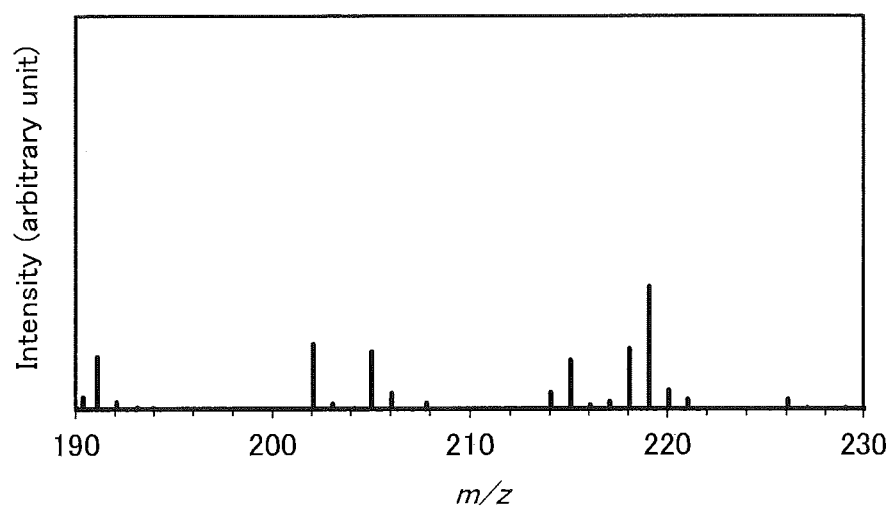

A component with m/z of 817.28250±10 ppm that underwent the ionization under the above-described conditions was collided with an argon gas in a collision cell to dissociate into product ions, and MSMS measurement was carried out. FIGS. 25A and 25B show detection results of ions, which were generated under a normalized collision energy (NCE) for the collision with argon of 50, with a Fourier transform mass spectrometer (FT MS).

The results in FIGS. 25A and 25B demonstrate that product ions of 1,6BnfAPrn-02, the organic compound of one embodiment of the present invention represented by Structural Formula (101), are detected at around m/z=218 and m/z=202. Note that the results in FIGS. 25A and 25B show characteristics derived from 1,6BnfAPrn-02 and thus can be regarded as important data for identifying 1,6BnfAPrn-02 contained in a mixture.

The product ion around m/z=218 is presumed to be a cation derived from benzo[b]naphtho[1,2-d]furan in the compound represented by Structural Formula (101), and this indicates a partial structure of 1,6BnfAPrn-02 of one embodiment of the present invention. In addition, the product ion around m/z=202 is presumed to be a cation derived from pyrene, and this indicates a partial structure of 1,6BnfAPrn-02, the organic compound of one embodiment of the present invention.

Example 3

Synthesis Example 3

In this example, a method for synthesizing 8-chlorobenzo[b]naphtho[1,2-d]furan (abbreviation: 8-ClBnf), which is the organic compound used in Example 2, is described. Note that a structure of 8-chlorobenzo[b]naphtho[1,2-d]furan is shown below.

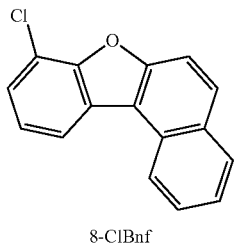 [SMILES: Clc1cccc2c1oc1ccc3ccccc3c12]

8-ClBnf

Step 1: Synthesis of 3-chloro-2-fluorobenzeneboronic acid

Into a 500 mL three-neck flask was put 16 g (72 mmol) of 1-bromo-3-chloro-2-fluorobenzene, and the air in the flask was replaced with nitrogen. After that, 200 mL of tetrahydrofuran was added to the solution, and this mixture solution was cooled down to −80° C. To this mixture solution, 48 mL (76 mmol) of n-BuLi (a 1.6 mol/L hexane solution) was dropped with a syringe, and then the resulting mixture was stirred at −80° C. for 1.5 hours.

After stirring, 9.0 mL (80 mmol) of trimethyl borate was added to this mixture. The mixture was stirred for approximately 19 hours while the temperature of the mixture was being returned to room temperature. After the stirring, approximately 100 mL of a 1 mol/L hydrochloric acid was added to the obtained solution, and the mixture was stirred. An organic layer of this mixture was washed with water and an aqueous layer was subjected to extraction with toluene twice. The extracted solution and the organic layer were combined and washed with saturated saline. The obtained organic layer was dried with magnesium sulfate, and this mixture was gravity-filtered. The obtained filtrate was concentrated to give 4.5 g of a pale yellow solid of the target substance in 35% yield. A synthesis scheme of Step 1 is shown in (c-1).

(c-1)

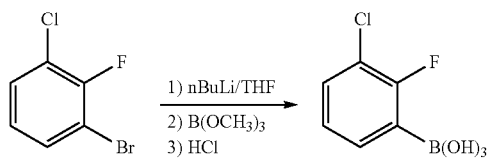

Step 2: Synthesis of 1-(3-chloro-2-fluorophenyl)-2-naphthol

Into a 200 mL three-neck flask were put 5.8 g (26 mmol) of 1-bromo-2-naphthol, 4.5 g (26 mmol) of 3-chloro-2-fluorobenzeneboronic acid, and 0.40 g (1.3 mol) of tri(orthotolyl)phosphine, and the air in the flask was replaced with nitrogen. To this mixture were added 150 mL of toluene, 50 mL of ethanol, and 21 mL of an aqueous solution of potassium carbonate (2.0 mol/L). The mixture was degassed by being stirred while the pressure in the flask was reduced, and then the air in the flask was replaced with nitrogen. To this mixture was added 58 mg (0.26 mmol) of palladium(II) acetate, and the resulting mixture was stirred at 90° C. under a nitrogen stream for 7 hours.

After the stirring, an organic layer of the mixture was washed with water, and then an aqueous layer was subjected to extraction with toluene. The extracted solution combined with the organic layer was washed with a saturated aqueous solution of sodium chloride, and the organic layer was dried with magnesium sulfate. The resulting mixture was gravity-filtered to give a filtrate. The obtained filtrate was concentrated to give a brown liquid. The liquid was purified by silica gel column chromatography using a mixed solvent (toluene:hexane=9:1) as a developing solvent to give 3.1 g of a brown liquid of the target substance in 44% yield. A synthesis scheme of Step 2 is shown in (c-2).

(c-2)

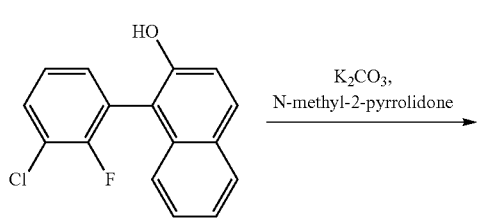

Step 3: Synthesis of 8-Chlorobenzo[b]naphtho[1,2-d]furan

Into a 300 mL recovery flask were put 3.1 g (11 mmol) of 1-(3-chloro-2-fluorophenyl)-2-naphthol, 70 mL of N-methyl-2-pyrrolidone, and 4.2 g (31 mmol) of potassium carbonate, and this mixture was stirred at 150° C. in the air for 7 hours. After the stirring, approximately 50 mL of water and approximately 50 mL of hydrochloric acid (1.0 mol/L) were added to the resulting mixture.

To the resulting solution was added approximately 100 mL of ethyl acetate, and then an aqueous layer was subjected to extraction with ethyl acetate three times. The extracted solution and an organic layer were combined and washed with a saturated aqueous solution of sodium hydrogen carbonate and a saturated aqueous solution of sodium chloride, and magnesium sulfate was then added. This mixture was gravity-filtered to give a filtrate. The resulting filtrate was concentrated to give 2.9 g of a pale brown solid of the target substance in 99% yield or higher. A synthetic scheme of Step 3 is shown in (c-3).

(c-3)

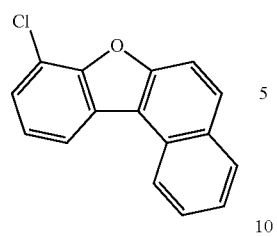

Figure 10A:
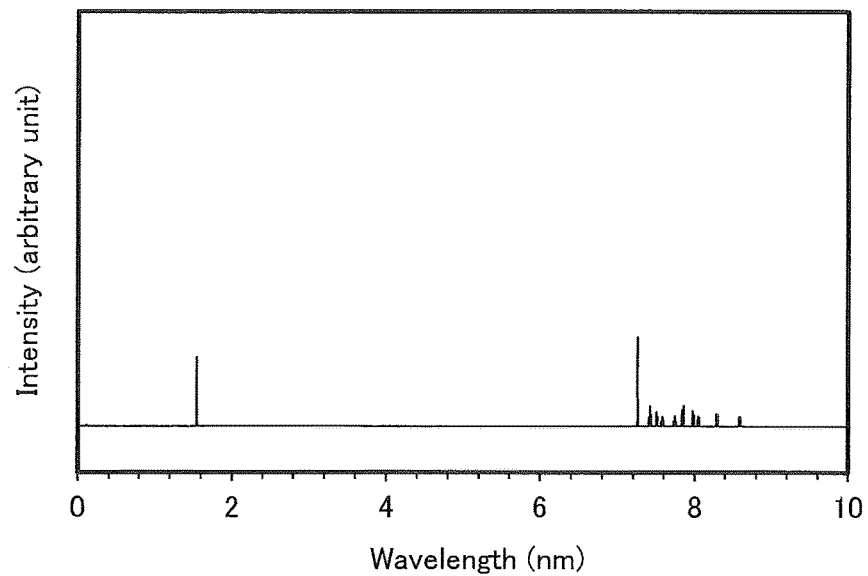
FIGS. 10A and 10B are $^1$H NMR charts of 8-halogenated benzo naphtho[1,2-d]furan.
Figure 10B:
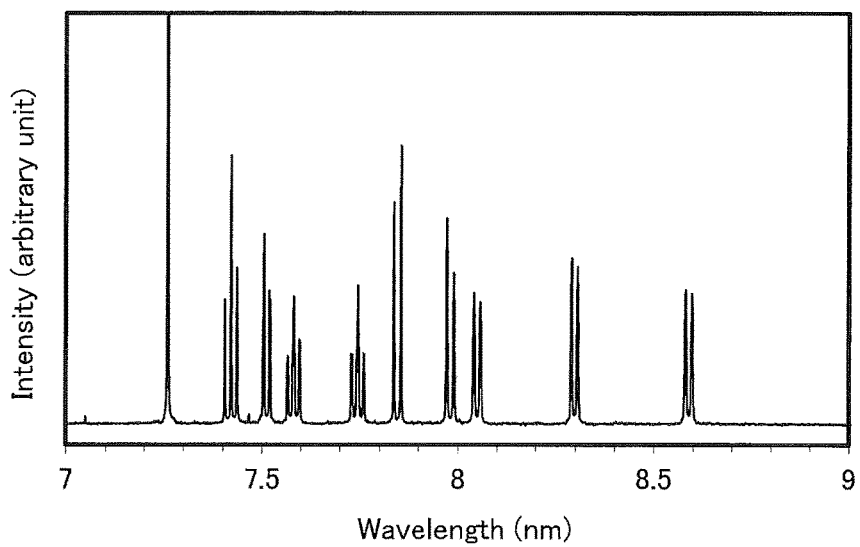

Analysis results by nuclear magnetic resonance ($^1$H-NMR) spectroscopy of the pale brown solid obtained in Step 3 are described below. FIGS. 10A and 10B are $^1$H NMR charts. The results revealed that 8-chlorobenzo[b]naphtho[1,2-d]furan, which is the organic compound synthesized by the method described in Synthesis Example 3, was obtained.

$^1$H NMR (CDCl$_3$, 500 MHz): δ=7.42 (t, J=4.7 Hz, 1H), 7.51 (d, J=4.5 Hz, 1H), 7.58 (t, J=4.5 Hz, 1H), 7.75 (t, J=4.5 Hz, 1H), 7.85 (d, J=5.4 Hz, 1H), 7.98 (d, J=5.1 Hz, 1H), 8.05 (d, J=4.8 Hz, 1H), 8.30 (d, J=4.2 Hz, 1H), 8.59 (d, J=4.8 Hz, 1H).

Example 4

Figure 11:
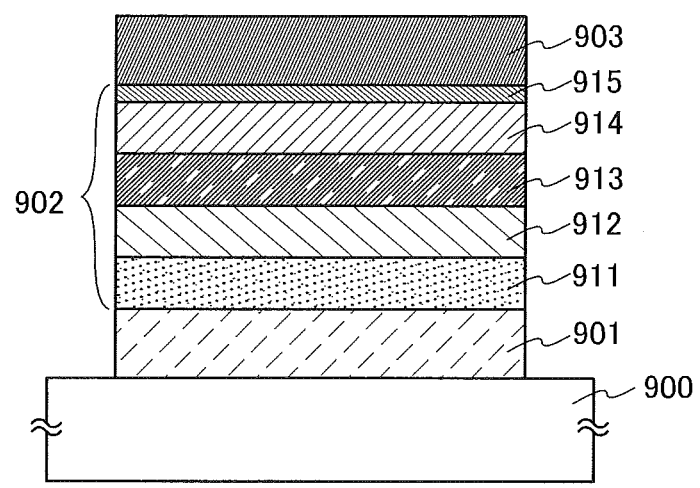
FIG. 11 illustrates a light-emitting element.

In this example, a light-emitting element 1 was fabricated. In the light-emitting element 1, 1,6BnfAPrn (Structural Formula (100)), the organic compound of one embodiment of the present invention, was used for a light-emitting layer. An emission spectrum of the light-emitting element 1 was measured. Note that the fabrication of the light-emitting element 1 is described with reference to FIG. 11. Chemical formulae of materials used in this example are shown below.

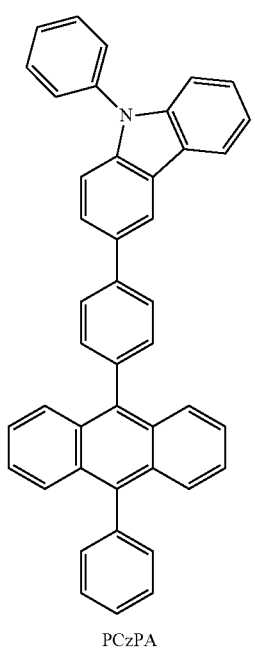

PCzPA

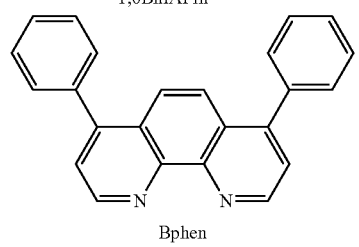

CzPA (100)

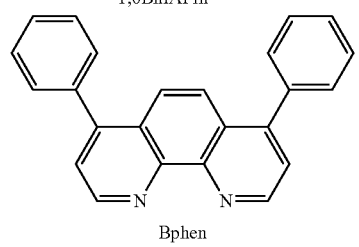

1,6BnfAPrn

Bphen

<<Fabrication of Light-Emitting Element 1>>

First, indium tin oxide containing silicon oxide (ITSO) was deposited over a glass substrate 900 by a sputtering method to form a first electrode 901 that functions as an anode. The thickness of the first electrode 901 was 110 nm. The electrode area was 2 mm×2 mm.

Next, as pretreatment for fabricating the light-emitting element 1 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 900 was cooled down for approximately 30 minutes.

Next, the substrate 900 was fixed to a holder provided in the vacuum evaporation apparatus so that a surface of the substrate 900 over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, are sequentially formed by a vacuum evaporation method.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) and molybdenum oxide were deposited by co-evaporation with a mass ratio of PCzPA to molybdenum oxide of 4:2 to form the hole-injection layer 911 on the first electrode 901. The thickness of the hole-injection layer 911 was 50 nm. Note that co-evaporation is an evaporation method in which a plurality of different substances are concurrently vaporized from different evaporation sources.

Next, 9-phenyl-3-[4-(10-phenyl-9-anthryl)phenyl]-9H-carbazole (abbreviation: PCzPA) was deposited to a thickness of 10 nm by evaporation to form the hole-transport layer 912.

Next, the light-emitting layer 913 was formed on the hole-transport layer 912. CzPA and 1,6BnfAPrn were deposited by co-evaporation with a mass ratio of CzPA to 1,6BnfAPrn of 1:0.01. The thickness of the light-emitting layer 913 was 25 nm.

Next, on the light-emitting layer 913, CzPA was deposited by evaporation to a thickness of 10 nm and then bathophenanthroline (abbreviation: Bphen) was deposited by evaporation to a thickness of 15 nm to form the electron-transport layer 914. Furthermore, lithium fluoride was deposited by evaporation to a thickness of 1 nm on the electron-transport layer 914 to form the electron-injection layer 915.

Finally, aluminum was deposited by evaporation to a thickness of 200 nm on the electron-injection layer 915 to form a second electrode 903 serving as a cathode. Thus, the light-emitting element 1 was obtained. Note that, in all the above evaporation steps, evaporation was performed by a resistance-heating method.

Table 1 shows an element structure of the light-emitting element 1 obtained in the above-described manner.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (110 nm) | PCzPA:MoOx (4:2 50 nm) | PCzPA (10 nm) | CzPA:1,6BnfAPrn (1:0.01 25 nm) | CzPA (10 nm) | Bphen (15 nm) | LiF (1 nm) | Al (200 nm) |

The fabricated light-emitting element 1 was sealed in a glove box containing a nitrogen atmosphere so as not to be exposed to the air (specifically, a sealant was applied onto outer edges of the elements, and at the time of sealing, UV treatment was performed first and then heat treatment was performed at 80° C. for 1 hour).

<<Operation Characteristics of Light-Emitting Element 1>>

Operation characteristics of the fabricated light-emitting element 1 were measured. Note that the measurement was carried out at room temperature (in an atmosphere kept at 25° C.).

Figure 12:
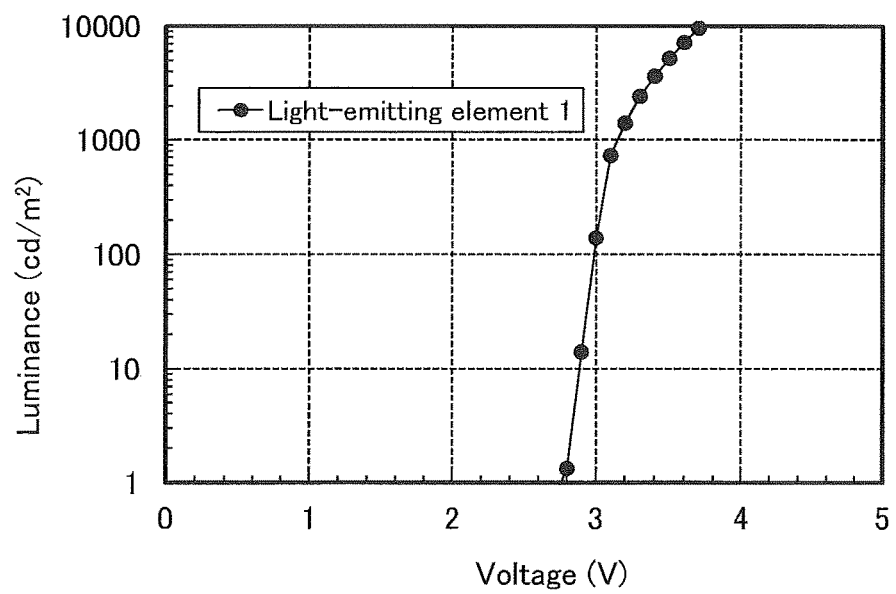
FIG. 12 shows voltage-luminance characteristics of a light-emitting element 1.
Figure 13:
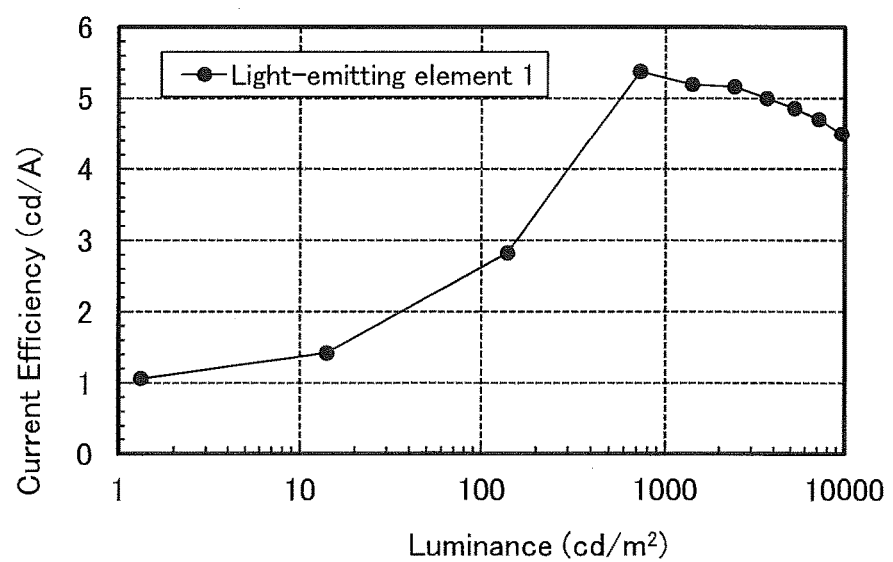
FIG. 13 shows luminance-current efficiency characteristics of the light-emitting element 1.
Figure 14:
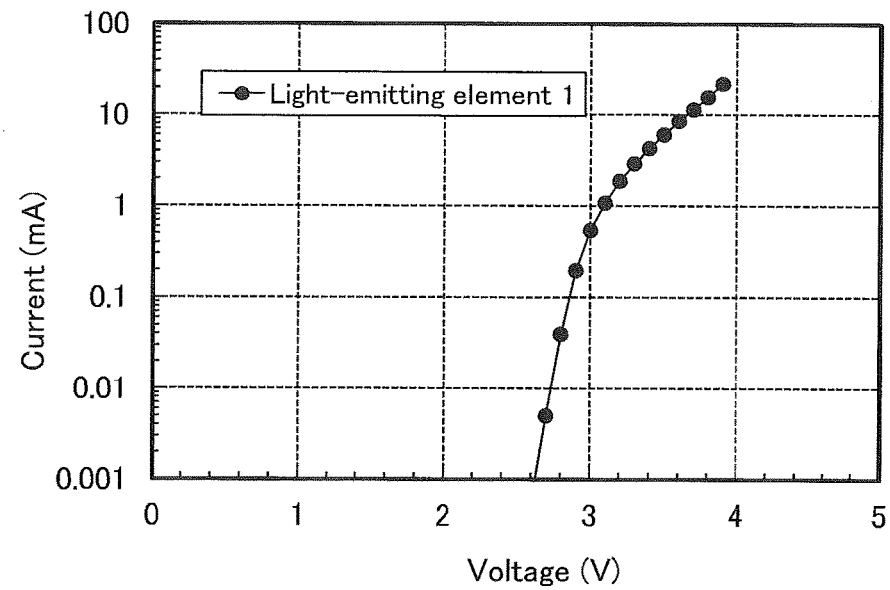
FIG. 14 shows voltage-current characteristics of the light-emitting element 1.
Figure 15:
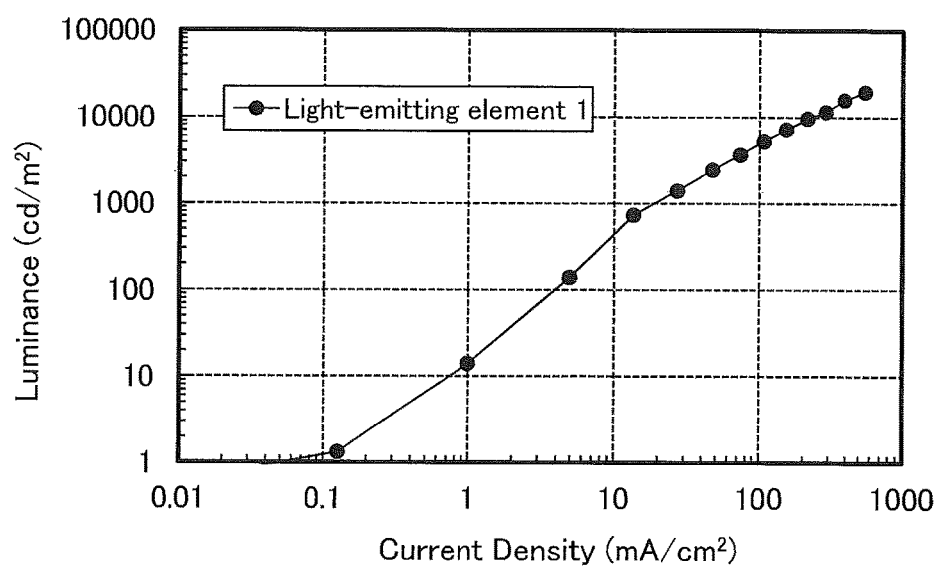
FIG. 15 shows current density-luminance characteristics of the light-emitting element 1.

FIG. 12 shows voltage-luminance characteristics of the light-emitting element 1. In FIG. 12, the vertical axis represents luminance (cd/m$^2$) and the horizontal axis represents voltage (V). FIG. 13 shows luminance-current efficiency characteristics of the light-emitting element 1. In FIG. 13, the vertical axis represents current efficiency (cd/A) and the horizontal axis represents luminance (cd/m$^2$). FIG. 14 shows voltage-current characteristics of the light-emitting element 1. In FIG. 14, the vertical axis represents current (mA) and the horizontal axis represents voltage (V). FIG. 15 shows current density-luminance characteristics of the light-emitting element 1. In FIG. 15, the vertical axis represents luminance (cd/m$^2$) and the horizontal axis represents current density (mA/cm$^2$).

According to FIG. 13, the light-emitting element 1 including 1,6BnfAPrn, the organic compound of one embodiment of the present invention, is a highly efficient element. Table 2 shows initial values of main characteristics of the light-emitting element 1 at a luminance of approximately 730 cd/m$^2$.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.1 | 0.54 | 14.0 | (0.14, 0.13) | 730 | 5 | 5 | 5.2 |

The above results revealed that the light-emitting element 1 fabricated in this example emitted blue light with high color purity. In addition, the light-emitting element 1 had high current efficiency.

Figure 16:
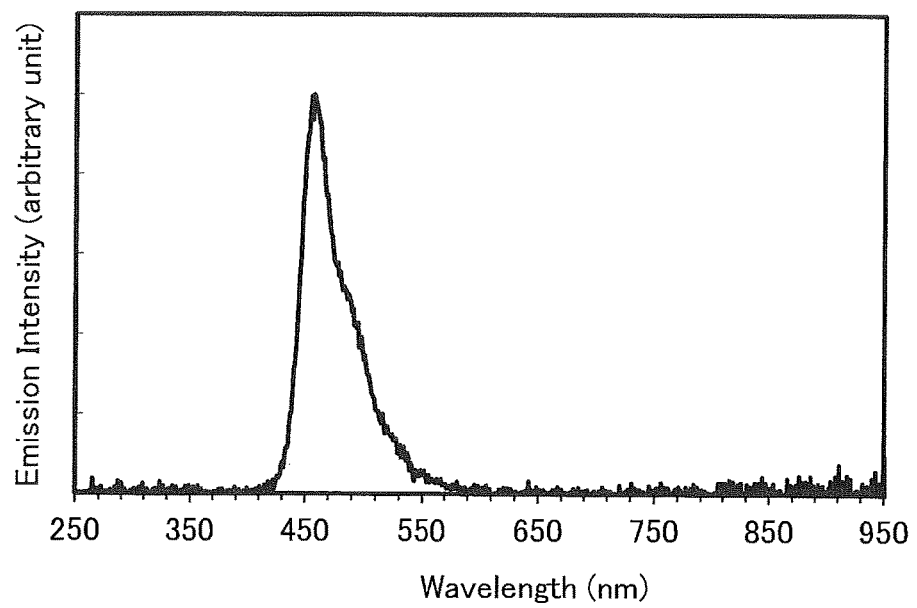
FIG. 16 shows an emission spectrum of the light-emitting element 1.

FIG. 16 shows an emission spectrum of the light-emitting element 1 that was obtained when current was applied to the light-emitting element 1 at a current density of 25 mA/cm$^2$. As shown in FIG. 16, the emission spectrum of the light-emitting element 1 had a peak at around 457 nm, which indicates that the peak was derived from emission of 1,6Bn-fAPrn that is the organic compound of one embodiment of the present invention.

Figure 17:
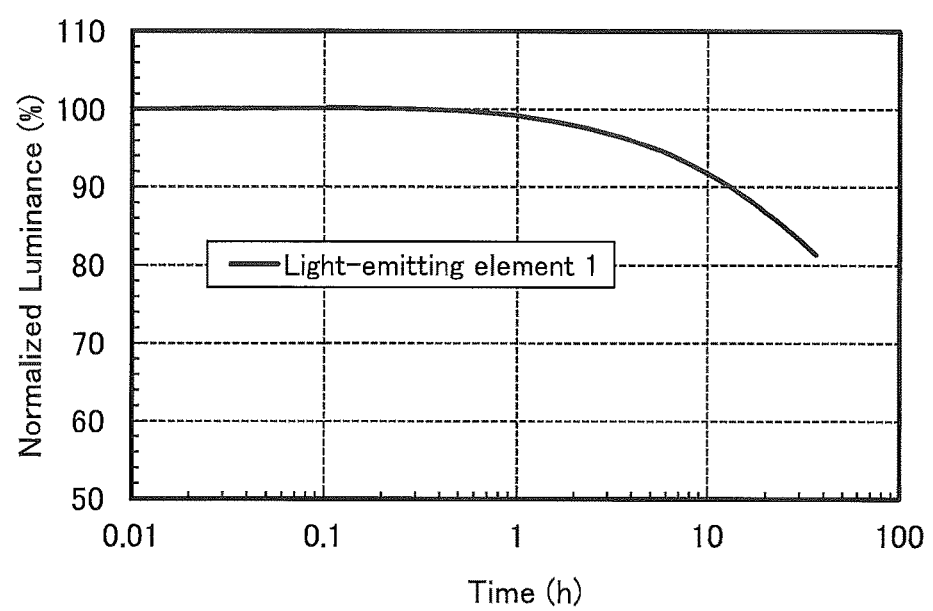
FIG. 17 shows reliability of the light-emitting element 1.

The light-emitting element 1 was subjected to a reliability test. Results of the reliability test are shown in FIG. 17. In FIG. 17, the vertical axis represents normalized luminance (%) with an initial luminance of 100% and the horizontal axis represents driving time (h) of the element. Note that in the reliability test, the light-emitting element 1 was driven under the conditions where the initial luminance was set to 5000 cd/m$^2$ and the current density was constant. The results revealed that the luminance of the light-emitting element 1 after 39-hour driving was approximately 81% of the initial luminance. This means that the light-emitting element 1 had a long lifetime.

Thus, the use of the organic compound of one embodiment of the present invention enables a light-emitting element with a long lifetime to be obtained.

Example 5

In this example, a light-emitting element 2 was fabricated. In the light-emitting element 2, 1,6BnfAPrn-02 (Structural Formula (101)), the organic compound of one embodiment of the present invention, was used for a light-emitting layer. In addition, a comparative light-emitting element 3 containing N,N'-(pyrene-1,6-diyl)bis[(N-phenyldibenzofuran)-4-amine] (abbreviation: 1,6FrAPrn-II) instead of 1,6BnfAPrn-02 of the light-emitting element 2 was fabricated in a similar method. The light-emitting element 2 and the comparative light-emitting element 3 were compared. Note that the fabrication of the light-emitting element 2 and the comparative light-emitting element 3 is described with reference to FIG. 11. Chemical formulae of materials used in this example are shown below.

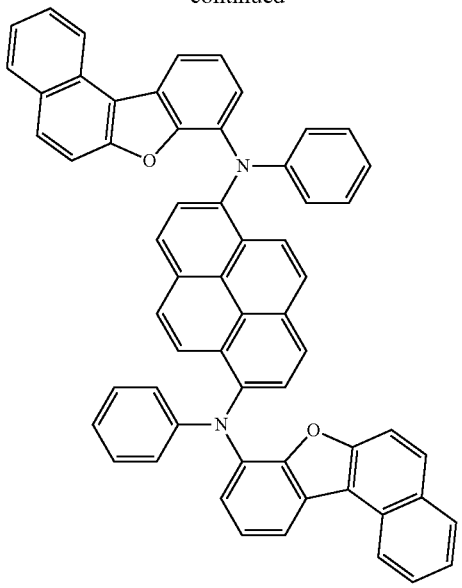

1,6BnfAPrn-02
(101)

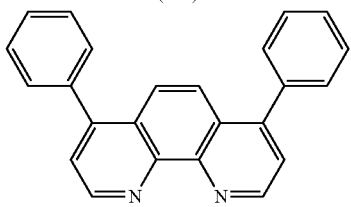

Bphen

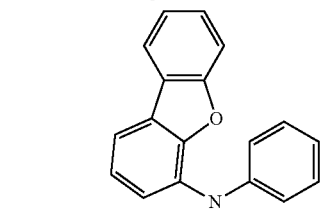

1,6FrAprn-II

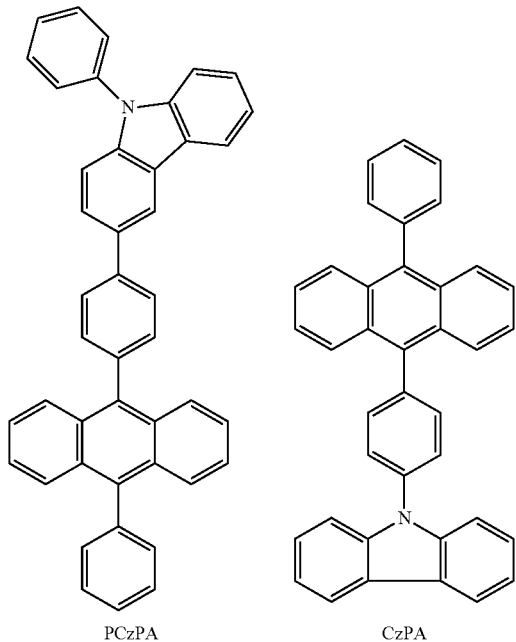

PCzPA        CzPA

<<Fabrication of Light-Emitting Element 2 and Comparative Light-Emitting element 3>>

First, indium tin oxide containing silicon oxide (ITSO) was deposited over a glass substrate 900 by a sputtering method to form a first electrode 901 that functions as an anode. The thickness of the first electrode 901 was 110 nm. The electrode area was 2 mm×2 mm.

Next, as pretreatment for fabricating the light-emitting element 2 and the comparative light-emitting element 3 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 900 was cooled down for approximately 30 minutes.

Next, the substrate 900 was fixed to a holder provided in the vacuum evaporation apparatus so that a surface of the substrate 900 over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, are sequentially formed by a vacuum evaporation method.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) and molybdenum oxide were deposited by co-evaporation with a mass ratio of PCzPA to molybdenum oxide of 4:2 to form the hole-injection layer 911 on the first electrode 901. The thickness of the hole-injection layer 911 was 50 nm. Note that co-evaporation is an evaporation method in which a plurality of different substances are concurrently vaporized from different evaporation sources.

Next, 9-phenyl-3-[4-(10-phenyl-9-anthryl)phenyl]-9H-carbazole (abbreviation: PCzPA) was deposited to a thickness of 10 nm by evaporation to form the hole-transport layer 912.

Next, the light-emitting layer 913 was formed on the hole-transport layer 912. In the case of the light-emitting element 2, CzPA and 1,6BnfAPrn-02 were deposited by co-evaporation with a mass ratio of CzPA to 1,6BnfAPrn-02 of 1:0.01. The thickness of the light-emitting layer 913 of the light-emitting element 2 was 25 nm. In the case of the comparative light-emitting element 3, CzPA and 1,6FrAPrn-II were deposited by co-evaporation with a mass ratio of CzPA to 1,6FrAPrn-II of 1:0.03. The thickness of the light-emitting layer 913 of the comparative light-emitting element 3 was 25 nm.

Next, on the light-emitting layer 913, CzPA was deposited by evaporation to a thickness of 10 nm and then bathophenanthroline (abbreviation: Bphen) was deposited by evaporation to a thickness of 15 nm to form the electron-transport layer 914. Furthermore, lithium fluoride was deposited by evaporation to a thickness of 1 nm on the electron-transport layer 914 to form the electron-injection layer 915.

Finally, aluminum was deposited by evaporation to a thickness of 200 nm on the electron-injection layer 915 to form a second electrode 903 serving as a cathode. Thus, the light-emitting element 2 and the comparative light-emitting element 3 were obtained. Note that, in all the above evaporation steps, evaporation was performed by a resistance-heating method.

Table 3 shows an element structure of the light-emitting element 2 and the comparative light-emitting element 3 obtained in the above-described manner.

TABLE 3

|  | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 2 | ITSO (110 nm) | PCzPA:MoOx (4:2 50 nm) | PCzPA (10 nm) | CzPA:1, 6BnfAPrn-02 (1:0.01 25 nm) | CzPA (10 nm) | Bphen (15 nm) | LiF (1 nm) | Al (200 nm) |
| Comparative light-emitting element 3 | ITSO (110 nm) | PCzPA:MoOx (4:2 50 nm) | PCzPA (10 nm) | CzPA:1, 6FrAPrn-II (1:0.03 25 nm) | CzPA (10 nm) | Bphen (15 nm) | LiF (1 nm) | Al (200 nm) |

The fabricated light-emitting element 2 and the comparative light-emitting element 3 were each sealed in a glove box containing a nitrogen atmosphere so as not to be exposed to the air (specifically, a sealant was applied onto outer edges of the elements, and at the time of sealing, IN treatment was performed first and then heat treatment was performed at 80° C. for 1 hour).

<<Operation Characteristics of Light-Emitting Element 2 and Comparative Light-Emitting Element 3>>

Operation characteristics of the fabricated light-emitting element 2 and the comparative light-emitting element 3 were measured. Note that the measurement was carried out at room temperature (in an atmosphere kept at 25° C.).

Figure 18:
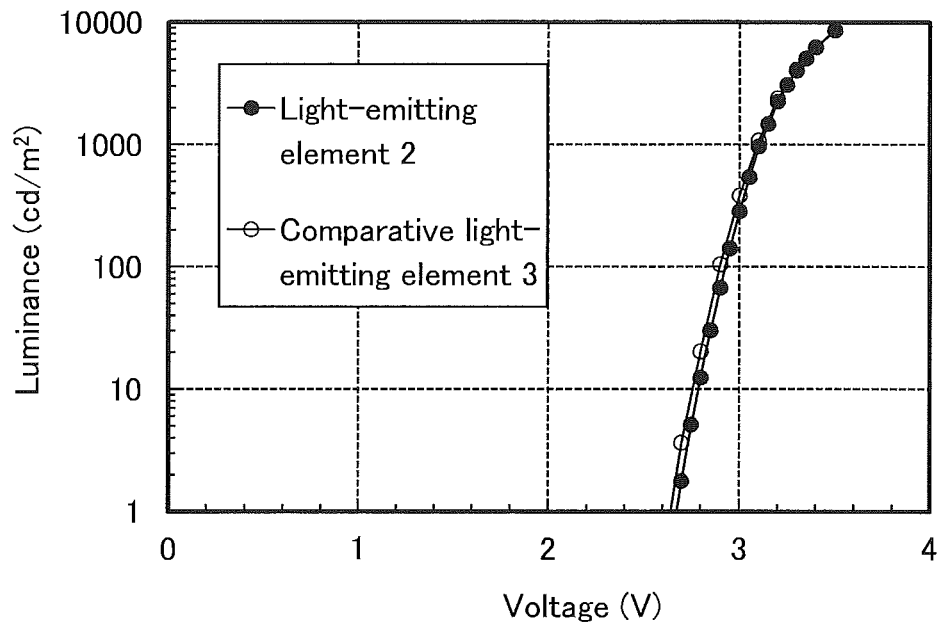
FIG. 18 shows voltage-luminance characteristics of a light-emitting element 2 and a comparative light-emitting element 3.
Figure 19:
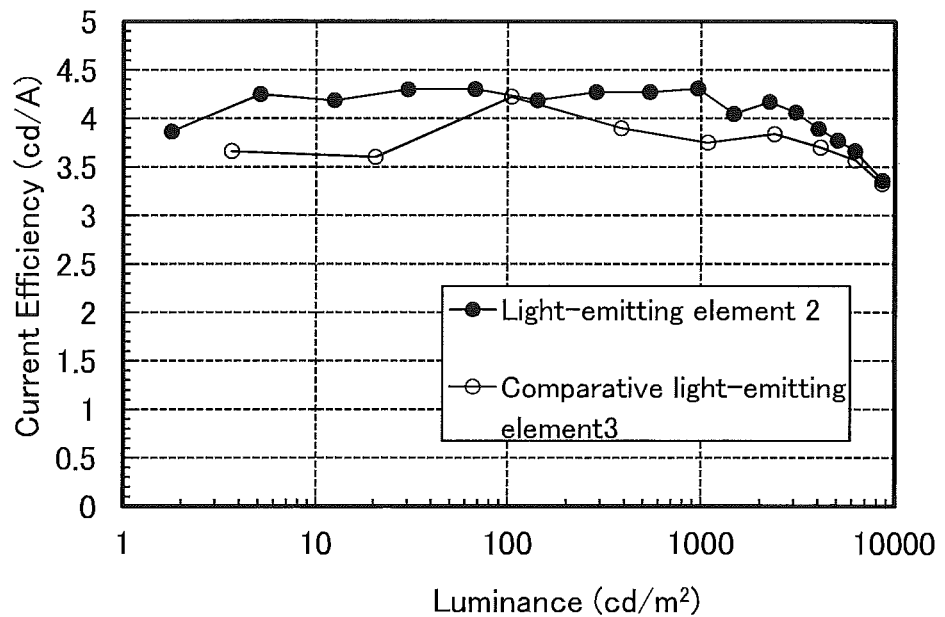
FIG. 19 shows luminance-current efficiency characteristics of the light-emitting element 2 and the comparative light-emitting element 3.
Figure 20:
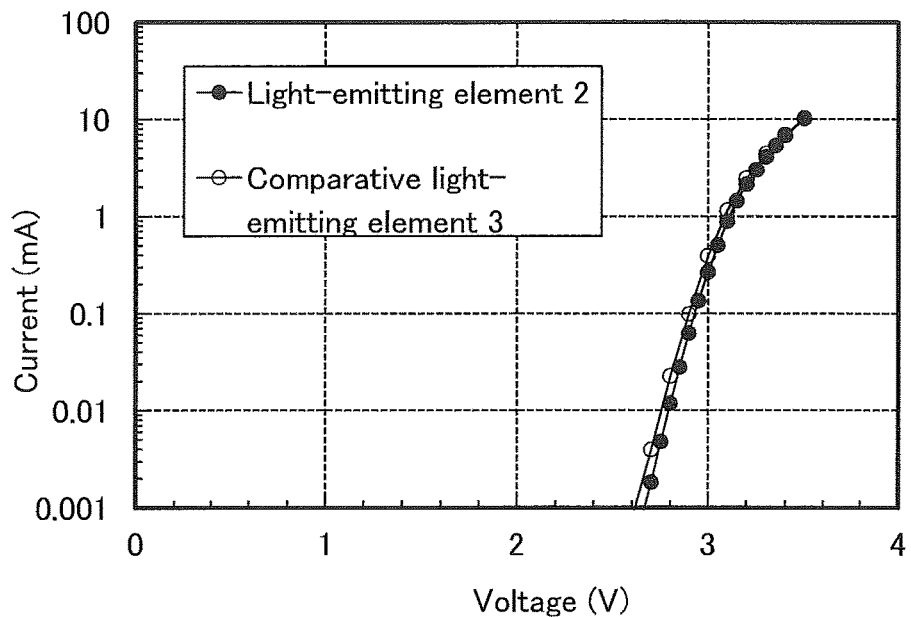
FIG. 20 shows voltage-current characteristics of the light-emitting element 2 and the comparative light-emitting element 3.
Figure 21:
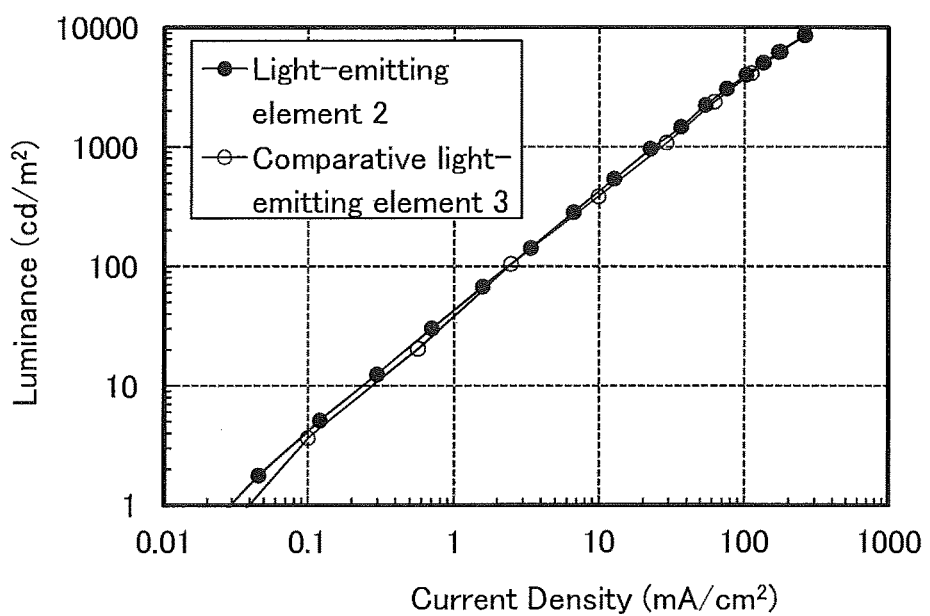
FIG. 21 shows current density-luminance characteristics of the light-emitting element 2 and the comparative light-emitting element 3.

FIG. 18 shows voltage-luminance characteristics of the light-emitting element 2 and the comparative light-emitting element 3. In FIG. 18, the vertical axis represents luminance ($cd/m^2$) and the horizontal axis represents voltage (V). FIG. 19 shows luminance-current efficiency characteristics of the light-emitting element 2 and the comparative light-emitting element 3. In FIG. 19, the vertical axis represents current efficiency (cd/A) and the horizontal axis represents luminance ($cd/m^2$). FIG. 20 shows voltage-current characteristics of the light-emitting element 2 and the comparative light-emitting element 3. In FIG. 20, the vertical axis represents current (mA) and the horizontal axis represents voltage (V). FIG. 21 shows current density-luminance characteristics of the light-emitting element 2 and the comparative light-emitting element 3. In FIG. 21, the vertical axis represents luminance ($cd/m^2$) and the horizontal axis represents current density ($mA/cm^2$).

FIG. 19 revealed that the light-emitting element 2 including 1,6BnfAPrn-02 that is the organic compound of one embodiment of the present invention has efficiency higher than the comparative light-emitting element 3 at around 1000 $cd/m^2$. Table 4 shows initial values of main characteristics of the light-emitting element 2 and the comparative light-emitting element 3.

TABLE 4

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 2 | 3.1 | 0.84 | 21 | (0.14, 0.10) | 920 | 4.4 | 4.5 | 5.2 |
| Comparative light-emitting element 3 | 3.1 | 1.16 | 28.9 | (0.14, 0.10) | 1080 | 3.8 | 3.8 | 4.4 |

The above results revealed that the light-emitting element 2 fabricated in this example had higher current efficiency than the comparative light-emitting element 3 though the light-emitting element 2 emits blue light with color purity as high as that of the comparative light-emitting element 3.

Figure 22:
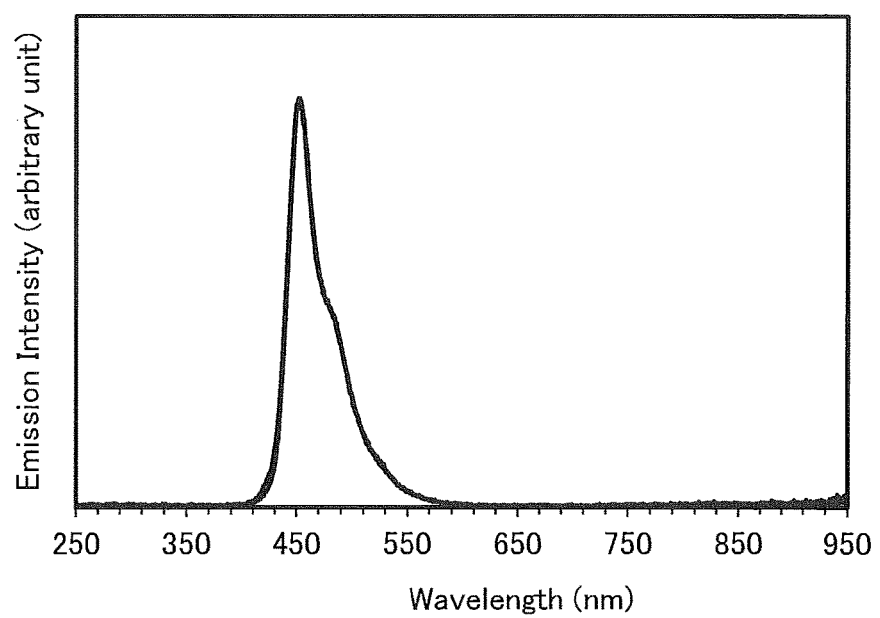
FIG. 22 shows emission spectra of the light-emitting element 2 and the comparative light-emitting element 3.

FIG. 22 shows emission spectra of the light-emitting element 2 and the comparative light-emitting element 3 that were obtained when current was applied to the light-emitting elements at a current density of 25 mA/cm$^2$. As shown in FIG. 22, the emission spectra of the light-emitting element 2 and the comparative light-emitting element 3 both had peaks at around 452 nm, which indicates that the peaks were derived from emission of 1,6BnfAPrn-02, the organic compound of one embodiment of the present invention, and from emission of 1,6FrAPrn-II, the organic compound used for comparison.

Figure 23:
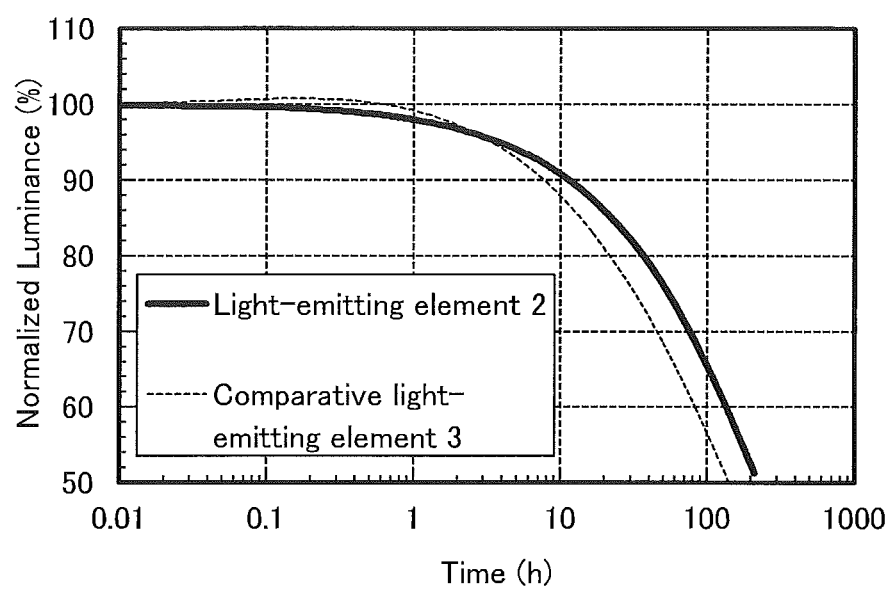
FIG. 23 shows reliability of each of the light-emitting element 2 and the comparative light-emitting element 3.

The light-emitting element 2 and the comparative light-emitting element 3 were subjected to reliability tests. Results of the reliability tests are shown in FIG. 23. In FIG. 23, the vertical axis represents normalized luminance (%) with an initial luminance of 100% and the horizontal axis represents driving time (h) of the elements. Note that in the reliability tests, the light-emitting element 2 and the comparative light-emitting element 3 were driven under the conditions where the initial luminance was set to 5000 cd/m$^2$ and the current density was constant. The results demonstrated that the luminance of the light-emitting element 2 after 100-hour driving was approximately 65% of the initial luminance. In other words, the light-emitting element 2 had a longer lifetime than the comparative light-emitting element 3 whose luminance after 100-hour driving was 56% of the initial luminance. Thus, the light-emitting element 2 including the organic compound of one embodiment of the present invention had not only high color purity but also a longer lifetime than the comparative light-emitting element 3. The above results indicate that the use of 1,6BnfAPrn-02, the organic compound that is one embodiment of the present invention and has a structure in which benzo[b]naphtho[1,2-d]furan is bonded to 1,6-diaminopyrene, makes it possible to provide a light-emitting element that emits blue light with high color purity and has a longer lifetime than the case of using 1,6FrAPrn-II, the organic compound that is used for comparison and has a structure in which dibenzofuran is bonded to 1,6-diaminopyrene.

Thus, the use of the organic compound of one embodiment of the present invention enables a light-emitting element that has high efficiency and a long lifetime to be obtained.

Example 6

Synthesis Example 4

In this example, a method for synthesizing N,N'-(pyrene-1,6-diyl)bis[(6,N-diphenylbenzo[b]naphtho[1,2-d]furan)-8-amine] (abbreviation: 1,6BnfAPrn-03), an organic compound of one embodiment of the present invention represented by Structural Formula (138) in Embodiment 1, is described. Note that a structure of 1,6BnfAPrn-03 is shown below.

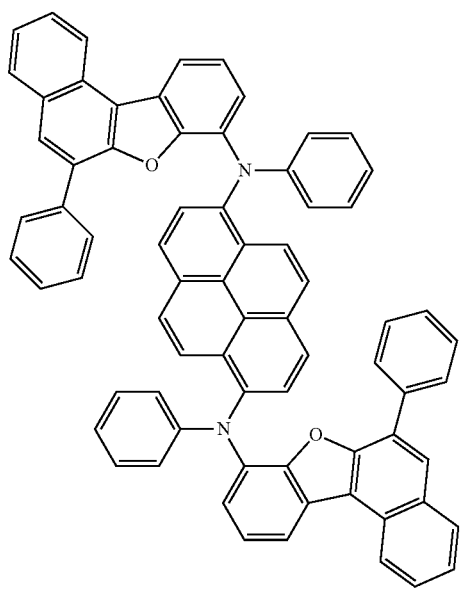

(138)

Step 1: Synthesis of 6-iodobenzo[b]naphtho[1,2-d]furan

Into a 500 mL three-neck flask were put 8.5 g (39 mmol) of benzo[b]naphtho[1,2-d]furan, and the air in the flask was replaced with nitrogen. Then, 195 mL of tetrahydrofuran was added thereto. This solution was cooled to −75° C. Then, 25 mL (40 mmol) of n-butyllithium (a 1.59 mol/L n-hexane solution) was dropped into this solution. After the drop, the resulting solution was stirred at room temperature for 1 hour.

After a predetermined period of time, the resulting solution was cooled to −75° C. Then, a solution in which 10 g (40 mmol) of iodine had been dissolved in 40 mL of THF was dropped into this solution. After the drop, the resulting solution was stirred for 17 hours while the temperature of the solution was returned to room temperature. After a predetermined period of time, an aqueous solution of sodium thiosulfate was added to the mixture, and the resulting mixture was stirred for 1 hour. Then, an organic layer of the mixture was washed with water and dried with magnesium sulfate. After the drying, the mixture was gravity-filtered to give a solution. The resulting solution was suction-filtered through Celite (Catalog No. 531-16855 produced by Wako Pure Chemical Industries, Ltd.) and Florisil (Catalog No. 540-00135 produced by Wako Pure Chemical Industries, Ltd.) to give a filtrate. The resulting filtrate was concentrated to give a solid. The resulting solid was recrystallized from toluene to give 6.0 g (18 mmol) of white powder of the target substance in 45% yield. A synthesis scheme of Step 1 is shown in (d-1).

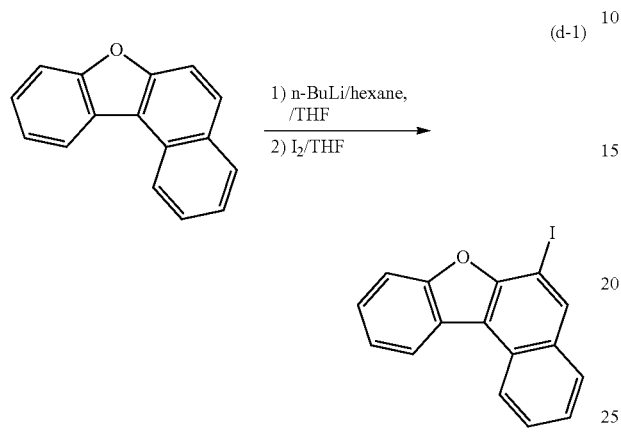

(d-1)

Step 2: Synthesis of 6-phenylbenzo[b]naphtho[1,2-d]furan

Into a 200 mL three-neck flask were put 6.0 g (18 mmol) of 6-iodobenzo[b]naphtho[1,2-d]furan, 2.4 g (19 mmol) of phenylboronic acid, 70 mL of toluene, 20 mL of ethanol, and 22 mL of an aqueous solution of potassium carbonate (2.0 mol/L). This mixture was degassed by being stirred while the pressure was reduced. After the degassing, the air in the flask was replaced with nitrogen, and then 480 mg (0.42 mmol) of tetrakis(triphenylphosphine)palladium(0) was added to the mixture. The resulting mixture was stirred at 90° C. under a nitrogen stream for 12 hours.

After a predetermined period of time, water was added to the mixture, and an aqueous layer was extracted with toluene. The extracted solution and an organic layer were combined, and the mixture was washed with water and then dried with magnesium sulfate. The mixture was gravity-filtered to give a filtrate. The resulting filtrate was concentrated to give a solid, and the resulting solid was dissolved in toluene. The resulting solution was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give a 4.9 g (17 mmol) of a white solid of the target substance in 93% yield. A synthesis scheme of Step 2 is shown in (d-2).

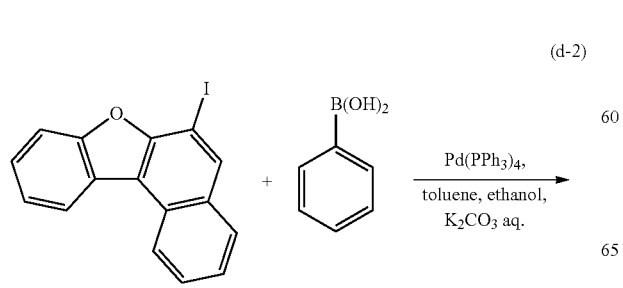

(d-2)

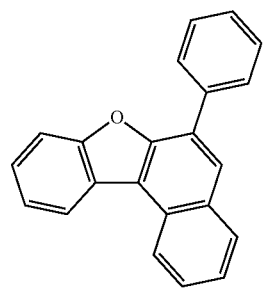

Step 3: Synthesis of 8-iodo-6-phenylbenzo[b]naphtho[1,2,d]furan

Into a 300 mL three-neck flask was put 4.9 g (17 mmol) of 6-phenylbenzo[b]naphtho[1,2-d]furan, and the air in the flask was replaced with nitrogen. Then, 87 mL of tetrahydrofuran (THF) was added thereto. The resulting solution was cooled to −75° C. Then, 11 mL (18 mmol) of n-butyllithium (a 1.59 mol/L n-hexane solution) was dropped into the solution. After the drop, the resulting solution was stirred at room temperature for 1 hour. After a predetermined period of time, the resulting solution was cooled to −75° C. Then, a solution in which 4.6 g (18 mmol) of iodine had been dissolved in 18 mL of THF was dropped into the resulting solution.

The resulting solution was stirred for 17 hours while the temperature of the solution was returned to room temperature. After a predetermined period of time, an aqueous solution of sodium thiosulfate was added to the mixture, and the resulting mixture was stirred for 1 hour. Then, an organic layer of the mixture was washed with water and dried with magnesium sulfate. The mixture was gravity-filtered to give a filtrate. The resulting filtrate was suction-filtered through Celite (Catalog No. 531-16855 produced by Wako Pure Chemical Industries, Ltd.), Florisil (Catalog No. 540-00135 produced by Wako Pure Chemical Industries, Ltd.), and alumina to give a filtrate. The resulting filtrate was concentrated to give a solid. The resulting solid was recrystallized from toluene to give 3.7 g (8.8 mmol) of a target white solid in 53% yield. A synthesis scheme of Step 3 is shown in (d-3).

(d-3)

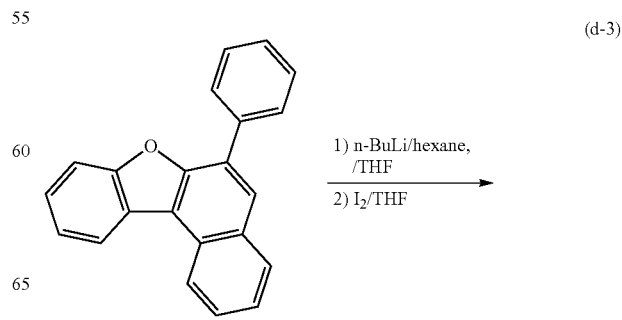

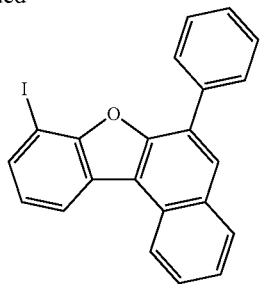

Step 4: Synthesis of 1,6BnfAPrn-03

Into a 100 mL three-neck flask were put 0.71 g (2.0 mmol) of 1,6-dibromopyrene, 1.0 g (10.4 mmol) of sodium-tert-butoxide, 10 mL of toluene, 0.36 mL (4.0 mmol) of aniline, and 0.3 mL of tri(tert-butyl)phosphine (a 10 wt % hexane solution), and the air in the flask was replaced with nitrogen. To this mixture was added 50 mg (85 µmol) of bis(dibenzylideneacetone)palladium(0), and the resulting mixture was stirred at 80° C. for 2 hours.

After a predetermined period of time, to the resulting mixture were added 1.7 g (4.0 mmol) of 8-iodo-6-phenyl-benzo[b]naphtho[1,2,d]furan, 180 mg (0.44 mmol) of 2-dicyclohexylphosphino-2',6'-dimethoxybiphenyl (abbreviation: S-Phos), and 50 mg (85 µmol) of bis(dibenzylideneacetone)palladium(0), and the resulting mixture was stirred at 100° C. for 15 hours. After a predetermined period of time, the resulting mixture was filtered through Celite (Catalog No. 531-16855 produced by Wako Pure Chemical Industries, Ltd.) to give a filtrate. The resulting filtrate was concentrated to give a solid. The resulting solid was washed with ethanol and recrystallized from toluene to give 1.38 g (1.4 mmol) of a yellow solid of the target substance in 71% yield.

By a train sublimation method, 1.37 mg (1.4 mmol) of the resulting yellow solid was purified by sublimation. The purification by sublimation was conducted by heating the yellow solid at 370° C. at an argon flow rate of 10 mL/min under a pressure of under a pressure of 2.3 Pa. As a result of the purification by sublimation, 0.68 g (0.70 mmol) of the yellow solid was recovered in 50% yield. A synthesis scheme of Step 4 is shown in (d-4).

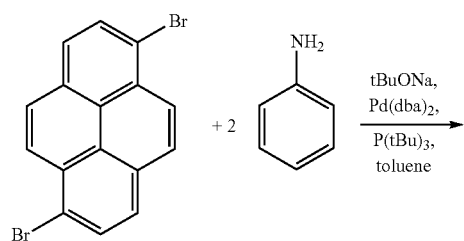

(d-4)

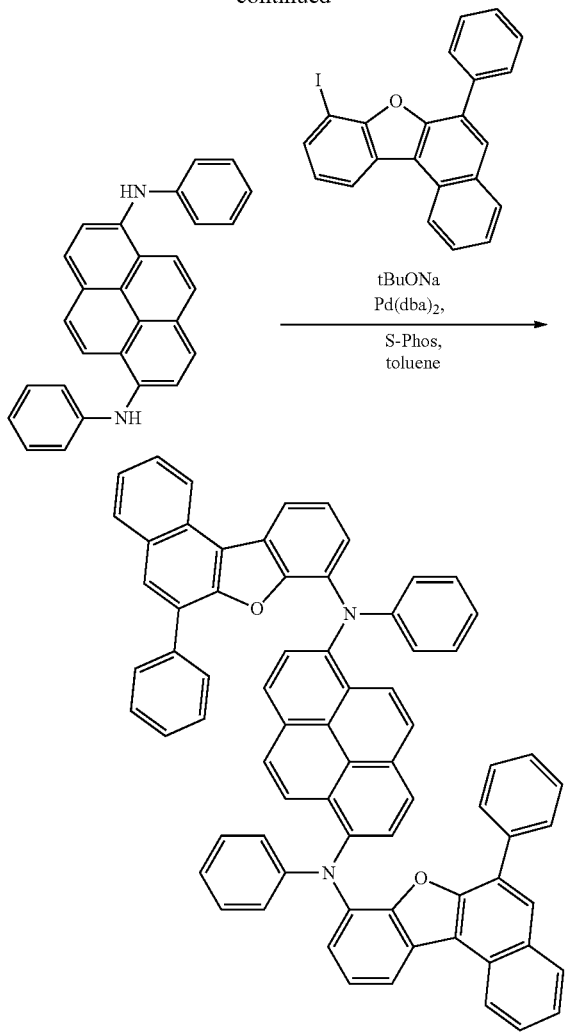

Figure 26A:
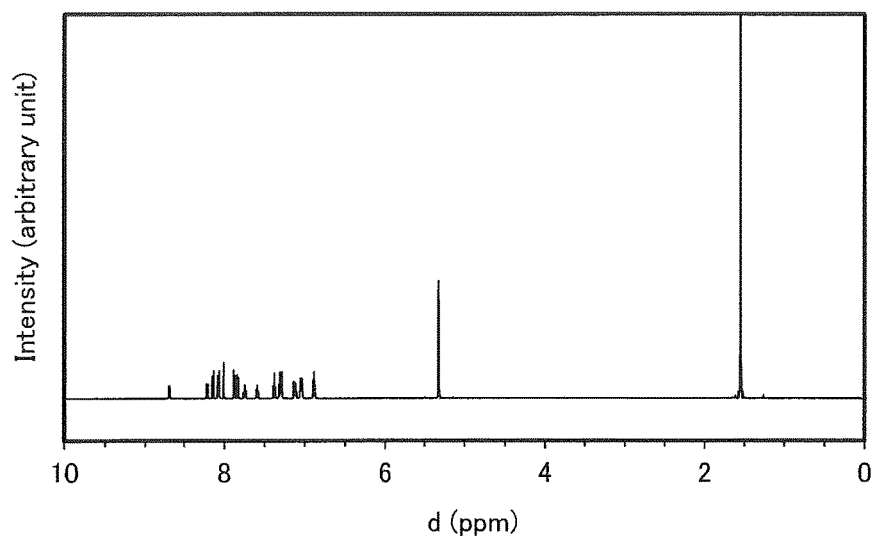
FIGS. 26A and 26B are $^1$H NMR charts of an organic compound represented by Structural Formula (138).
Figure 26B:
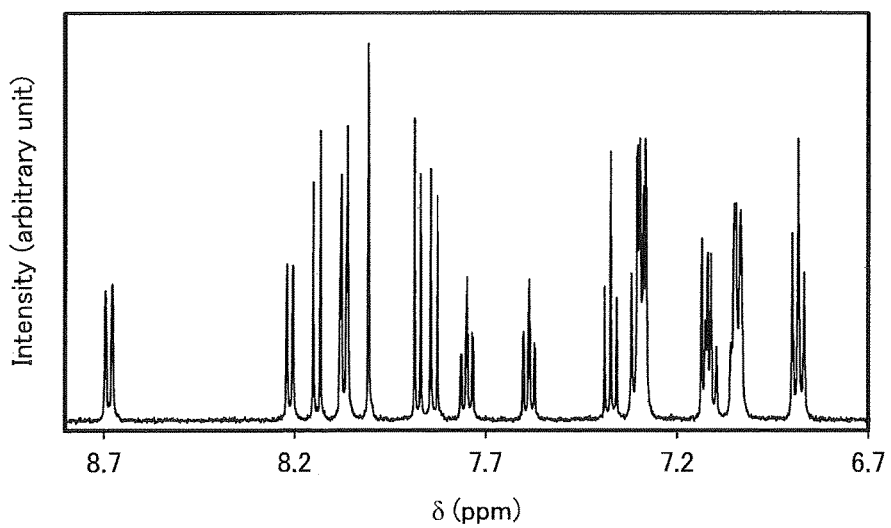

Analysis results by nuclear magnetic resonance ($^1$H-NMR) spectroscopy of the yellow solid obtained in Step 4 are described below. FIGS. 26A and 26B are $^1$H NMR charts. FIG. 26B is a chart where the range from 6.7 (ppm) to 8.8 (ppm) on the horizontal axis (δ) in FIG. 26A is enlarged. The results revealed that 1,6BnfAPrn-03, the organic compound synthesized by the method described in Synthesis Example 4, was obtained.

$^1$H NMR (dichloromethane-d2, 500 MHz): δ=6.88 (t, J=7.7 Hz, 4H), 7.03-7.06 (m, 6H), 7.11 (t, J=7.5 Hz, 2H), 7.13 (d, J=8.0 Hz, 2H), 7.28-7.32 (m, 8H), 7.37 (t, J=8.0 Hz, 2H), 7.59 (t, J=7.2 Hz, 2H), 7.75 (t, J=7.7 Hz, 2H), 7.84 (d, J=9.0 Hz, 2H), 7.88 (d, J=8.0 Hz, 2H), 8.01 (s, 2H), 8.07 (d, J=8.0 Hz, 4H), 8.14 (d, J=9.0 Hz, 2H), 8.21 (d, J=8.0 Hz, 2H), 8.69 (d, J=8.5 Hz, 2H).

Figure 27A:
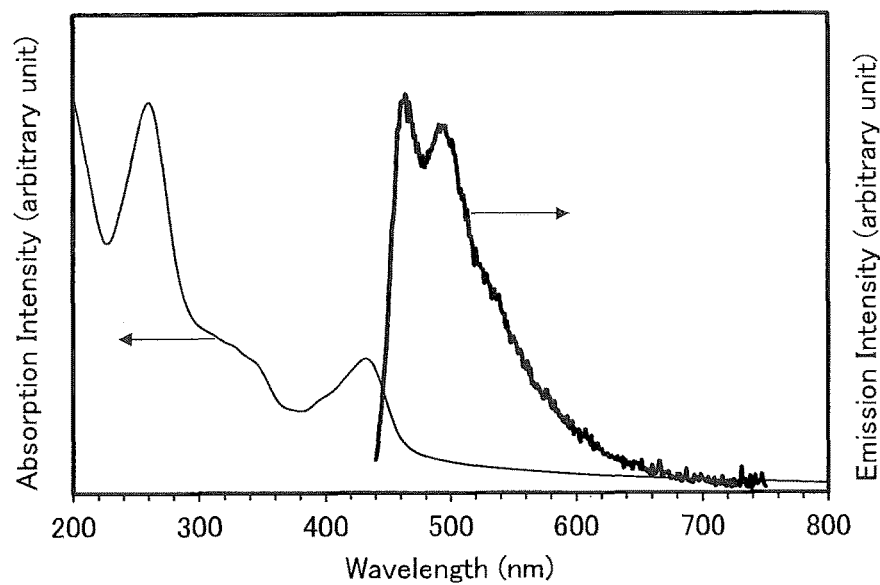
FIGS. 27A and 27B show ultraviolet-visible absorption spectra and emission spectra of the organic compound represented by Structural Formula (138).

Next, an ultraviolet-visible absorption spectrum (hereinafter, simply referred to as "absorption spectrum") and an emission spectrum of 1,6BnfAPrn-03 in a toluene solution were measured. The absorption spectrum was measured at room temperature with an ultraviolet-visible light spectrophotometer (V-550, manufactured by JASCO Corporation) in a state where the toluene solution was put in a quartz cell. The emission spectrum was measured with a fluorescence spectrophotometer (FS920, manufactured by Hamamatsu Photonics Corporation) at room temperature in a state where the toluene solution was put in the quartz cell. FIG. 27A shows measurement results of the absorption spectrum and the emission spectrum. The horizontal axis represents wavelength (nm) and the vertical axis represents absorption intensity (arbitrary unit) and emission intensity (arbitrary unit). In FIG. 27A, two solid lines are shown: a thin line represents the absorption spectrum and a thick line represents the emission spectrum. The absorption spectrum shown in FIG. 27A is a result obtained by subtraction of an absorption spectrum of only toluene in a quartz cell from the measured absorption spectrum of the toluene solution in the quartz cell.

As shown in FIG. 27A, 1,6BnfAPrn-03 that is the organic compound of one embodiment of the present invention has an emission peak at 464 nm, which means that blue light emission was observed in the toluene solution.

Figure 27B:
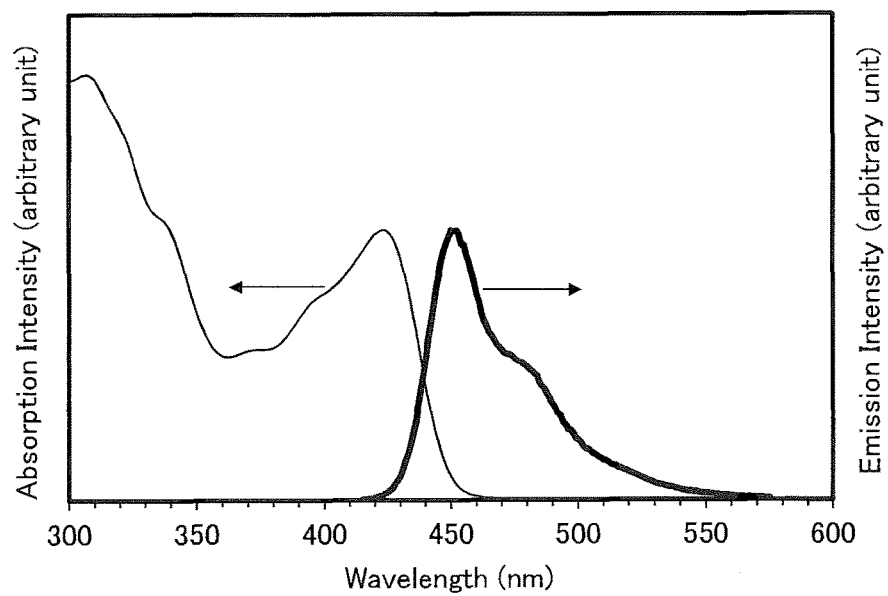

FIG. 27B shows an absorption spectrum and an emission spectrum of a thin film of 1,6BnfAPrn-03. The absorption spectrum was measured with an ultraviolet-visible spectrophotometer (V-550, produced by JASCO Corporation). The measurement was performed with samples each prepared in such a manner that the thin film was deposited on a quartz substrate. The absorption spectrum was obtained by subtraction of an absorption spectrum of only the quartz substrate from absorption spectra of the thin film on the quartz substrate. In FIG. 27B, the horizontal axis represents wavelength (nm) and the vertical axis represents absorption intensity (arbitrary unit).

Example 7

In this example, a light-emitting element 4 was fabricated. In the light-emitting element 4, 1,6BnfAPrn-03 (Structural Formula (138)), the organic compound of one embodiment of the present invention, was used for a light-emitting layer. An emission spectrum of the light-emitting element 1 was measured. Note that the fabrication of the light-emitting element 4 is described with reference to FIG. 11. Chemical formulae of materials used in this example are shown below.

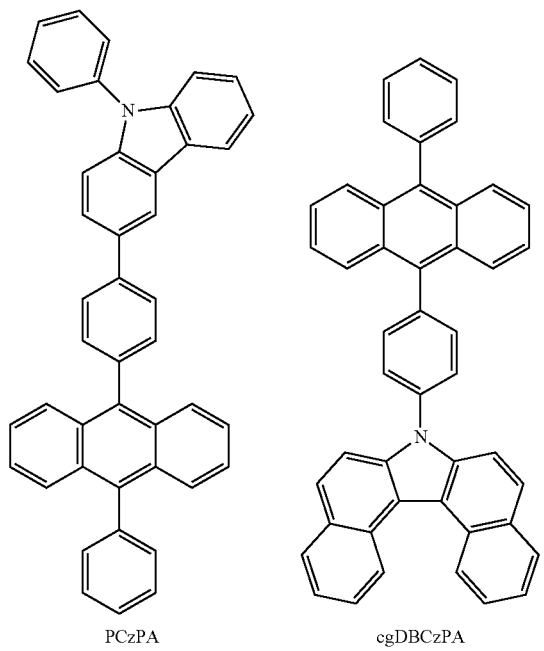

PCzPA          cgDBCzPA

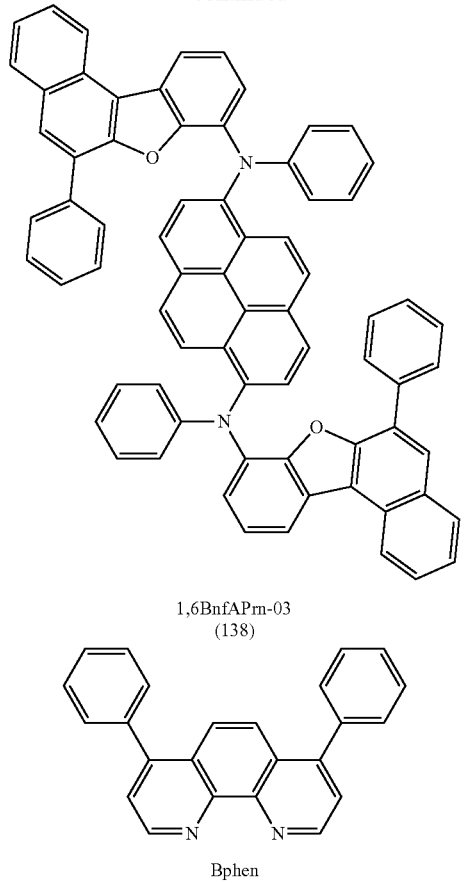

1,6BnfAPrn-03
(138)

Bphen

<<Fabrication of Light-Emitting Element 4>>

First, indium tin oxide containing silicon oxide (ITSO) was deposited over a glass substrate 900 by a sputtering method to form a first electrode 901 that functions as an anode. The thickness of the first electrode 901 was 110 nm. The electrode area was 2 mm×2 mm.

Next, as pretreatment for fabricating the light-emitting element 4 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 900 was cooled down for approximately 30 minutes.

Next, the substrate 900 was fixed to a holder provided in the vacuum evaporation apparatus so that a surface of the substrate 900 over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, are sequentially formed by a vacuum evaporation method.

After the pressure in the vacuum evaporation apparatus was reduced to $10^{-4}$ Pa, 9-phenyl-3-[4-(10-phenyl-9-anthryl)phenyl]-9H-carbazole (abbreviation: PCzPA) and molybdenum oxide were deposited by co-evaporation with a mass ratio of PCzPA to molybdenum oxide of 4:2 to form the hole-injection layer 911 on the first electrode 901. The thickness of the hole-injection layer 911 was 50 nm. Note that co-evaporation is an evaporation method in which a plurality of different substances are concurrently vaporized from different evaporation sources.

Next, PCzPA was deposited to a thickness of 10 nm by evaporation to form the hole-transport layer 912.

Next, the light-emitting layer 913 was formed on the hole-transport layer 912. In the case of the light-emitting element 4, 7-[4-(10-phenyl-9-anthryl)phenyl]-7H-dibenzo[c,g]carbazole (abbreviation: cgDBCzPA) and 1,6BnfAPrn-03 were deposited by co-evaporation with a mass ratio of cgDBCzPA to 1,6BnfAPrn-03 of 1:0.01. The thickness of the light-emitting layer 913 was 25 nm.

Next, on the light-emitting layer 913, cgDBCzPA was deposited by evaporation to a thickness of 10 nm and then bathophenanthroline (abbreviation: Bphen) was deposited by evaporation to a thickness of 15 nm to form the electron-transport layer 914. Furthermore, lithium fluoride was deposited by evaporation to a thickness of 1 nm on the electron-transport layer 914 to form the electron-injection layer 915.

Finally, aluminum was deposited by evaporation to a thickness of 200 nm on the electron-injection layer 915 to form a second electrode 903 serving as a cathode. Thus, the light-emitting element 4 was obtained. Note that, in all the above evaporation steps, evaporation was performed by a resistance-heating method.

Figure 30:
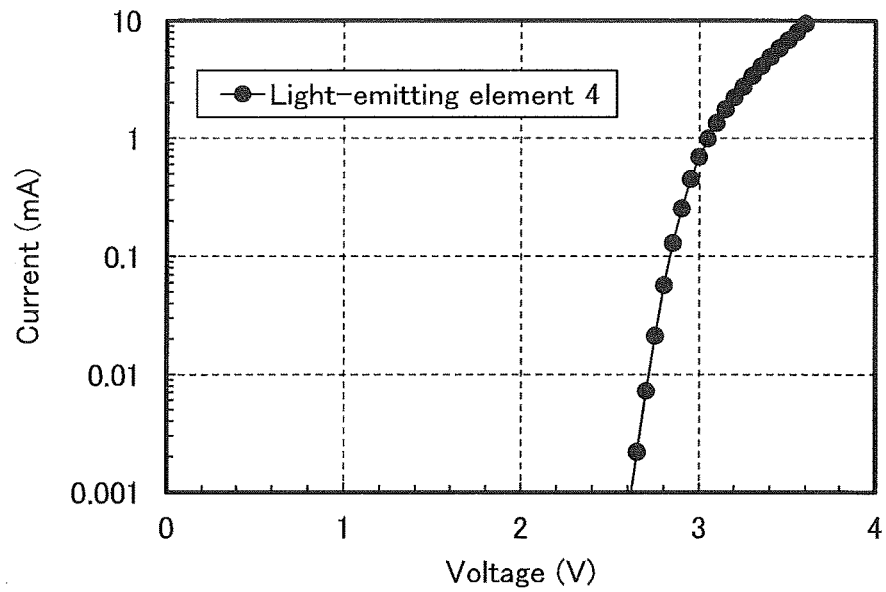
FIG. 30 shows voltage-current characteristics of the light-emitting element 4.
Figure 31:
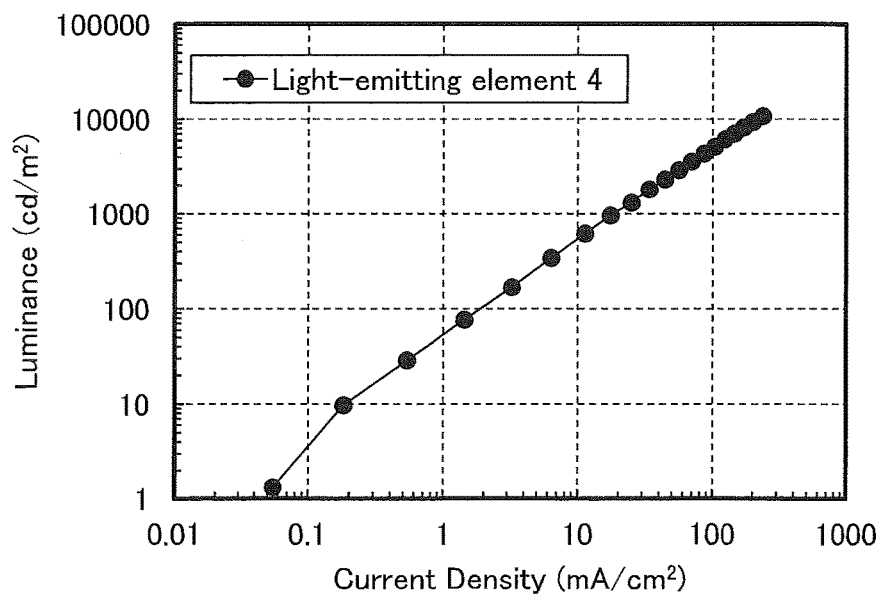
FIG. 31 shows current density-luminance characteristics of the light-emitting element 4.

Table 5 shows an element structure of the light-emitting element 4 obtained in the above-described manner.

the vertical axis represents current efficiency (cd/A) and the horizontal axis represents luminance ($cd/m^2$). FIG. 30 shows voltage-current characteristics of the light-emitting element 4. In FIG. 30, the vertical axis represents current (mA) and the horizontal axis represents voltage (V). FIG. 31 shows current density-luminance characteristics of the light-emitting element 4. In FIG. 31 the vertical axis represents luminance ($cd/m^2$) and the horizontal axis represents current density ($mA/cm^2$).

Figure 29:
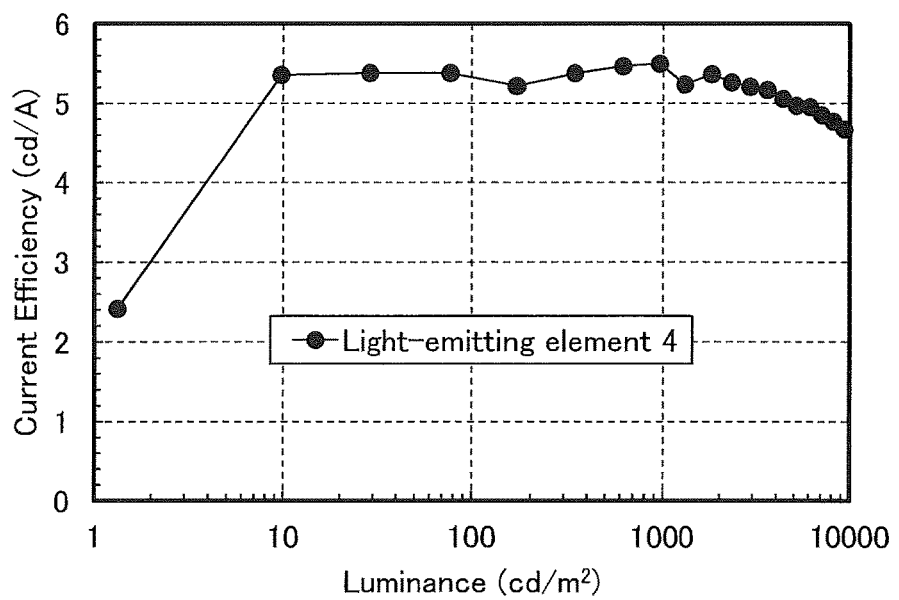
FIG. 29 shows luminance-current efficiency characteristics of the light-emitting element 4.

FIG. 29 revealed that the light-emitting element 4 including 1,6BnfAPrn-03 that is the organic compound of one embodiment of the present invention was a highly efficient element. Table 6 shows initial values of main characteristics of the light-emitting element 4.

TABLE 6

|  | Voltage (V) | Current (mA) | Current density ($mA/cm^2$) | Chromaticity (x, y) | Luminance ($cd/m^2$) | Current efficiency (cd/A) | Power efficiency (lm/W) | External quantum efficiency (%) |
|---|---|---|---|---|---|---|---|---|
| Light-emitting element 4 | 3.0 | 0.7 | 17 | (0.14, 0.09) | 960 | 5.5 | 5.8 | 6.9 |

The above results revealed that the light-emitting element 4 fabricated in this example had high current efficiency.

Figure 32:
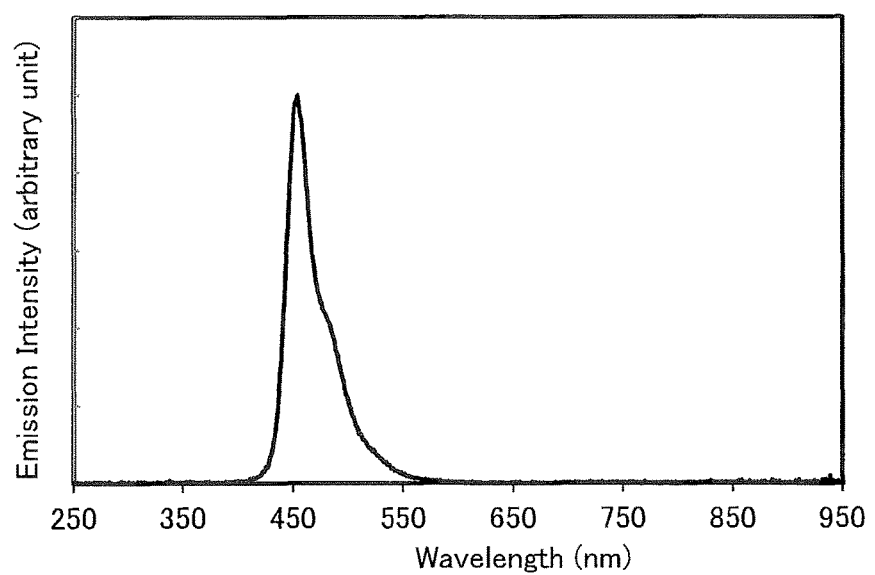
FIG. 32 shows an emission spectrum of the light-emitting element 4.

FIG. 32 shows an emission spectrum of the light-emitting element 4 that was obtained when current was applied to the light-emitting element 1 at a current density of 25 $mA/cm^2$. As shown in FIG. 32, the emission spectrum of the light-emitting element 4 had a peak at around 454 nm, which indicates that the peak was derived from emission of 1,6BnfAPrn-03 that is the organic compound of one embodiment of the present invention.

Figure 33:
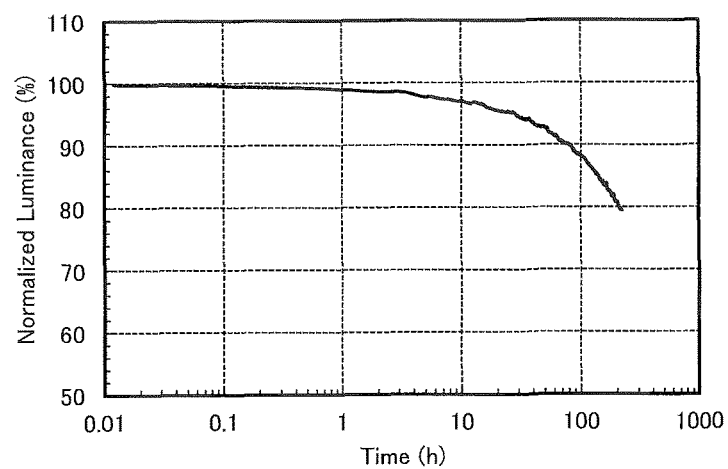
FIG. 33 shows reliability of the light-emitting element 4.

The light-emitting element 4 was subjected to a reliability test. Results of the reliability tests are shown in FIG. 33. In FIG. 33, the vertical axis represents normalized luminance (%) with an initial luminance of 100% and the horizontal axis represents driving time (h) of the element. Note that in the reliability test, the light-emitting element 4 was driven

TABLE 5

|  | First electrode | Hole-injection layer | Hole-transport layer | Light-emitting layer | Electron-transport layer | Electron-injection layer | Second electrode |
|---|---|---|---|---|---|---|---|
| Light-emitting element 4 | ITSO (110 nm) | PCzPA:MoOx (4:2 50 nm) | PCzPA (10 nm) | cgDBCzPA:1, 6BnfAPrn-03 (1:0.01 25 nm) | cgDBCzPA (10 nm) | Bphen (15 nm) | LiF (1 nm) | Al (200 nm) |

The fabricated light-emitting element 1 was sealed in a glove box containing a nitrogen atmosphere so as not to be exposed to the air (specifically, a sealant was applied onto outer edges of the elements, and at the time of sealing, UV treatment was performed first and then heat treatment was performed at 80° C. for 1 hour).

<<Operation Characteristics of Light-Emitting Element 4>>

Operation characteristics of the fabricated light-emitting element 4 were measured. Note that the measurement was carried out at room temperature (in an atmosphere kept at 25° C.).

Figure 28:
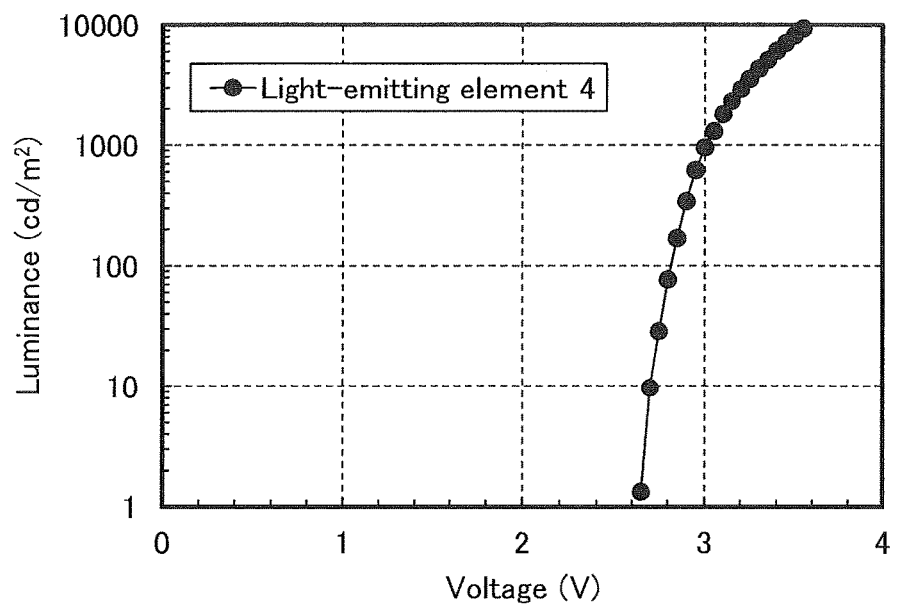
FIG. 28 shows voltage-luminance characteristics of a light-emitting element 4.

FIG. 28 shows voltage-luminance characteristics of the light-emitting element 4. In FIG. 28, the vertical axis represents luminance ($cd/m^2$) and the horizontal axis represents voltage (V). FIG. 29 shows luminance-current efficiency characteristics of the light-emitting element 4. In FIG. 29, under the conditions where the initial luminance was set to 5000 $cd/m^2$ and the current density was constant. The results demonstrated that the luminance of the light-emitting element 4 after 100-hour driving was approximately 88% of the initial luminance. Thus, the comparative light-emitting element 3 including the organic compound of one embodiment of the present invention had not only high color purity but also a long lifetime. The above results indicate that the use of 1,6BnfAPrn-03, the organic compound that is one embodiment of the present invention and has a structure in which benzo[b]naphtho[1,2-d]furan is bonded to 1,6-diaminopyrene, enables a light-emitting element that emits blue light with high color purity and has a long lifetime to be provided.

Thus, the use of the organic compound of one embodiment of the present invention enables a light-emitting element that has high efficiency and a long lifetime to be obtained. In addition, 1,6BnfAPrn-03 has a structure in which a phenyl group is bonded to the 6-position of benzo[b]naphtho[1,2-d]furan; thus, an element that had very high color purity, high efficiency, and high reliability was obtained. This revealed that among the compounds in the present invention, the compound having the structure in which a substituted or unsubstituted phenyl group, particularly, an unsubstituted phenyl group is bonded to the 6-position of benzo[b]naphtho[1,2-d]furan is preferable.

REFERENCE NUMERALS

101: first electrode, 102: EL layer, 103: second electrode, 111: hole-injection layer, 112: hole-transport layer, 113: light-emitting layer, 114: electron-transport layer, 115: electron-injection layer, 116: charge-generation layer, 201: first electrode, 202(1): first EL layer, 202(2): second EL layer, 202(n−1): (n−1)th EL layer, 202(n): n-th EL layer, 204: second electrode, 205: charge-generation layer (I), 205(1): first charge-generation layer (I), 205(2): second charge-generation layer (I), 205(n−2): (n−2)th charge-generation layer (I), 205(n−1): (n−1)th charge-generation layer (I), 301: element substrate, 302: pixel portion, 303: driver circuit portion (source line driver circuit), 304a, 304b: driver circuit portion (gate line driver circuit), 305: sealant, 306: sealing substrate, 307: wiring, 308: flexible printed circuit (FPC), 309: n-channel FET, 310: p-channel FET, 311: switching FET, 312: current control FET, 313: first electrode (anode), 314: insulator, 315: EL layer, 316: second electrode (cathode), 317: light-emitting element, 318: space, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7302: housing, 7304: display panel, 7305: icon, 7306: icon, 7311: operation button, 7312: operation button, 7313: connection terminal, 7321: band, 7322: clasp, 7400: mobile phone, 7401: housing, 7402: display portion, 7403: operation button, 7404: external connection port, 7405: speaker, 7406: microphone, 900: substrate, 901: first substrate, 902: EL layer, 903: second electrode, 911: hole-injection layer, 912: hole-transport layer, 913: light-emitting layer, 914: electron-transport layer, 915: electron-injection layer, 8001: lighting device, 8002: lighting device, 8003: lighting device, and 8004: lighting device.

This application is based on Japanese Patent Application serial no. 2013-155318 filed with the Japan Patent Office on Jul. 26, 2013, the entire contents of which are hereby incorporated by reference.

What is claimed is:

1. A method for synthesizing an organic compound represented by formula (G1):

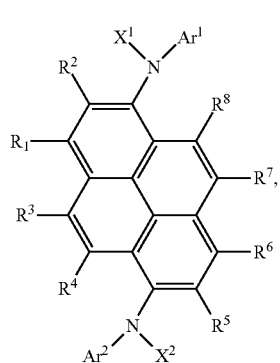

(G1)

the method comprising:
reacting a pyrene compound having halogen or a trifluoromethanesulfonyl group at 1- and 6-positions of a pyrene unit with an arylamine to form a 1,6-bis(N-aryl)aminopyrene compound; and
reacting the 1,6-bis(N-aryl)aminopyrene compound with a halogenated benzo[b]naphtho[1,2-d]furan, wherein:

$Ar^1$ and $Ar^2$ are separately represent a substituted or unsubstituted aryl group having 6 to 13 carbon atoms;

$R^1$ to $R^8$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms; and $X^1$ and $X^2$ are separately represent a substituted or unsubstituted benzo[b]naphtho[1,2-d]furanyl group.

2. The method according to claim 1, wherein nitrogen atoms in formula (G1) are separately bonded to a 6- or 8-position of the benzo[b]naphtho[1,2-d]furanyl group.

3. The method according to claim 1, wherein:

the organic compound is represented by formula (G2):

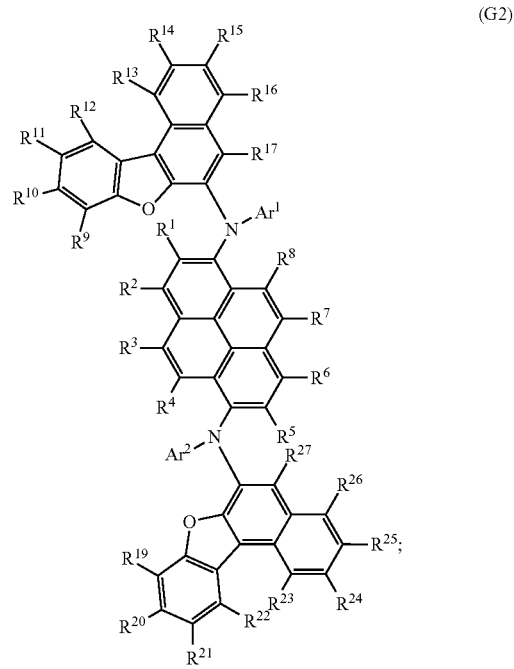

(G2)

and $R^9$ to $R^{17}$ and $R^{19}$ to $R^{27}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

4. The method according to claim 1,
wherein:
the organic compound is represented by formula (G3):

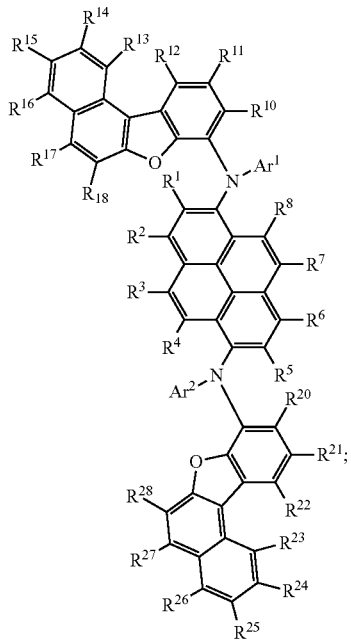

(G3)

and

R$^{10}$ to R$^{18}$ and R$^{20}$ to R$^{28}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

5. The method according to claim 1,
wherein:
the organic compound is represented by formula (G4):

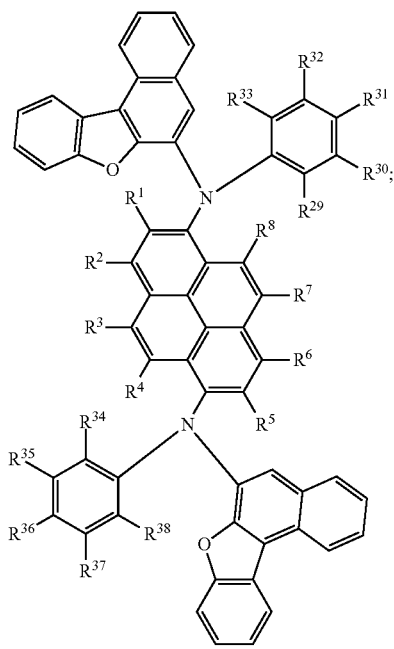

(G4)

and

R$^{29}$ to R$^{33}$ and R$^{34}$ to R$^{38}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

6. The method according to claim 1,
wherein:
the organic compound is represented by formula (G5):

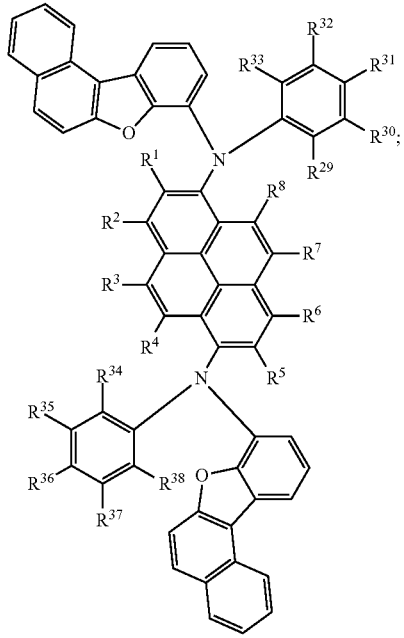

(G5)

and

R$^{29}$ to R$^{33}$ and R$^{34}$ to R$^{38}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

7. The method according to claim 1,
wherein the organic compound is represented by any of formulae (100) and (101):

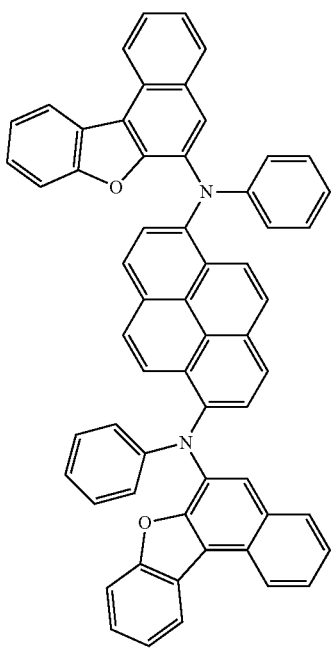

(100)

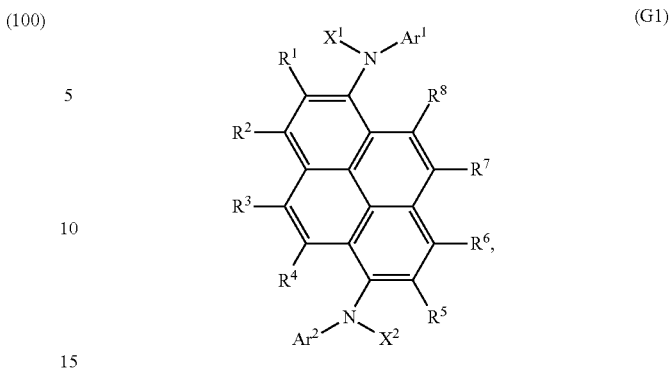

(G1)

the method comprising reacting a pyrene compound having halogen or a trifluoromethanesulfonyl group at 1- and 6-positions of a pyrene unit with an amine body of a benzo[b]naphtho[1,2-d]furan compound, wherein:

$Ar^1$ and $Ar^2$ are separately represent a substituted or unsubstituted aryl group having 6 to 13 carbon atoms;

$R^1$ to $R^8$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms; and $X^1$ and $X^2$ are separately represent a substituted or unsubstituted benzo[b]naphtho[1,2-d]furanyl group.

9. The method according to claim 8, wherein nitrogen atoms in formula (G1) are separately bonded to a 6- or 8-position of the benzo[b]naphtho[1,2-d]furanyl group.

10. The method according to claim 8, wherein:

the organic compound is represented by formula (G2):

(101)

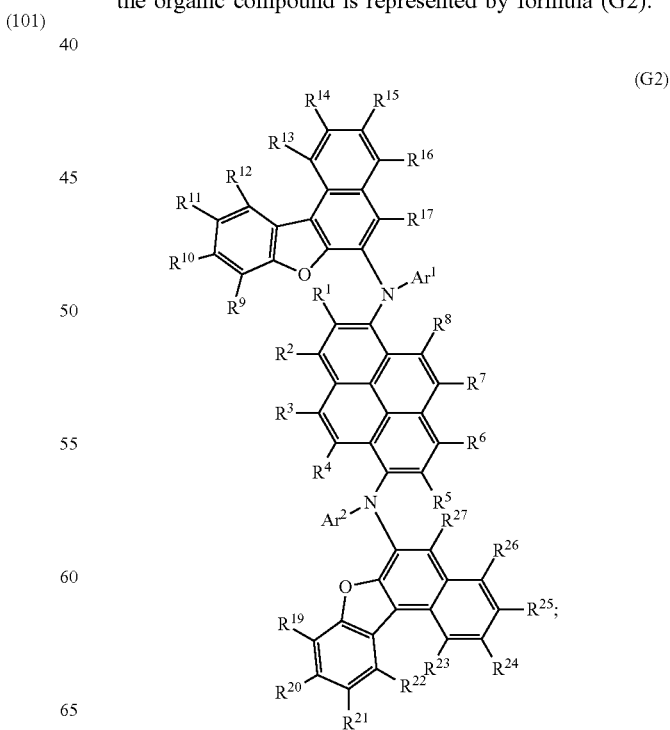

8. A method for synthesizing an organic compound represented by formula (G1):

and $R^9$ to $R^{17}$ and $R^{19}$ to $R^{27}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

11. The method according to claim 8, wherein:

the organic compound is represented by formula (G3):

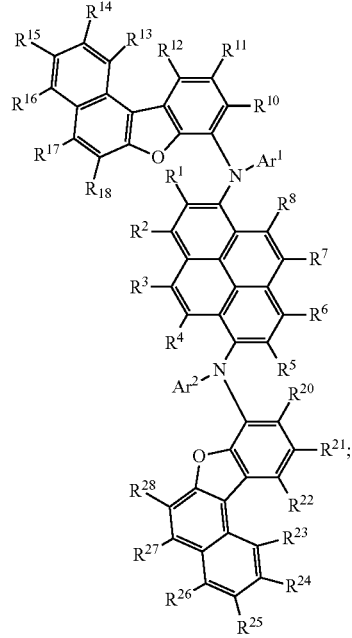

(G3)

and $R^{10}$ to $R^{18}$ and $R^{20}$ to $R^{28}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

12. The method according to claim 8, wherein:

the organic compound is represented by formula (G4):

(G4)

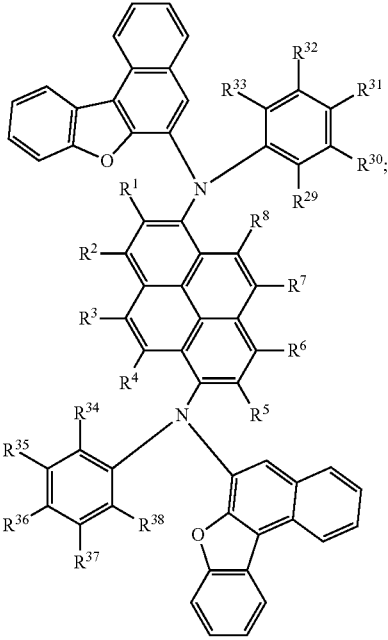

and $R^{29}$ to $R^{33}$ and $R^{34}$ to $R^{38}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

13. The method according to claim 8, wherein:

the organic compound is represented by formula (G5):

(G5)

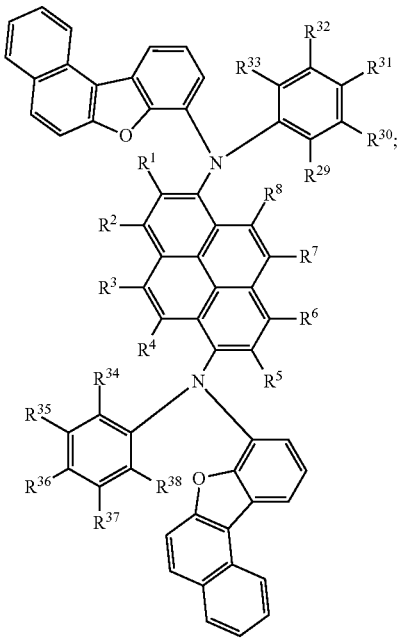

and $R^{29}$ to $R^{33}$ and $R^{34}$ to $R^{38}$ separately represent any one of hydrogen, a substituted or unsubstituted alkyl group having 1 to 6 carbon atoms, a substituted or unsubstituted alkoxy group having 1 to 6 carbon atoms, a cyano group, halogen, a substituted or unsubstituted haloalkyl group having 1 to 6 carbon atoms, and a substituted or unsubstituted aryl group having 6 to 10 carbon atoms.

14. The method according to claim 8, wherein the organic compound is represented by any of formulae (100) and (101):

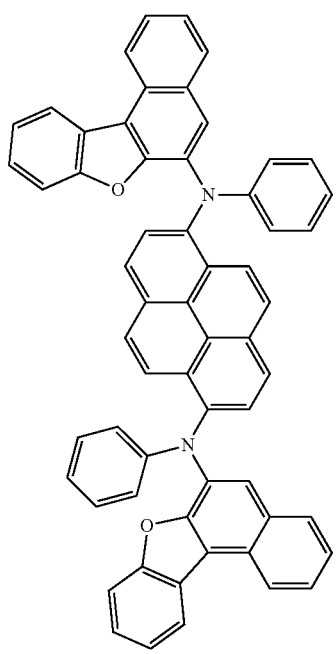

(100)

-continued

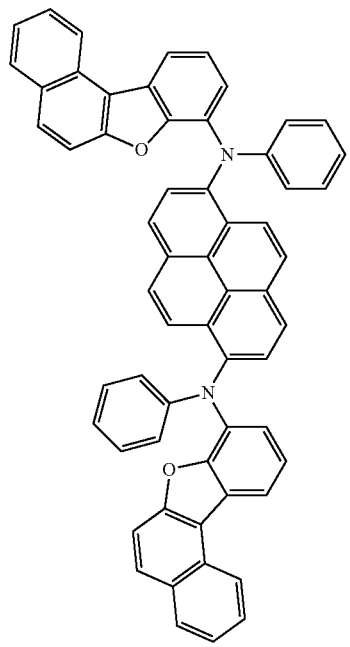

(101)

* * * * *